United States Patent [19]
Matsumoto et al.

[11] Patent Number: 5,523,460
[45] Date of Patent: Jun. 4, 1996

[54] 4-FLUOROBIPHENYL DERIVATIVES

[75] Inventors: Masakatsu Matsumoto, Sagamihara; Nobuko Watanabe, Tokyo; Eiko Mori, Tokyo; Miwa Ishihara, Tokyo; Tetsuaki Yamaura, Tokyo; Misao Aoyama, Tokyo; Hiroshi Ikawa, Tokyo; Hisako Kobayashi, Tokyo, all of Japan

[73] Assignee: Fujirebio Inc., Tokyo, Japan

[21] Appl. No.: 218,186

[22] Filed: Mar. 28, 1994

[30]    Foreign Application Priority Data

Mar. 26, 1993  [JP]  Japan .................................. 5-090557

[51] Int. Cl.$^6$ ............................. C07C 69/76; A01N 43/16
[52] U.S. Cl. .............................. 560/60; 560/53; 562/463; 562/470; 549/292
[58] Field of Search ..................... 560/60, 53; 562/470, 562/463; 549/292; 514/570, 532, 545, 460

[56]    References Cited

FOREIGN PATENT DOCUMENTS 0388732  9/1990   European Pat. Off. .
3918364  12/1990  Germany .

Primary Examiner—Paul J. Killos
Attorney, Agent, or Firm—Oblon, Spivak, McClelland, Maier & Neustadt

[57]    ABSTRACT

A 4-fluorobiphenyl derivative of formula (I), which is useful as a cholesterol lowering agent or a lipid lowering agent because of its strong inhibitory effect on HMG-CoA reductase), and which is also useful as an intermediate for producing the above-mentioned cholesterol lowering agent or lipid lowering agent:

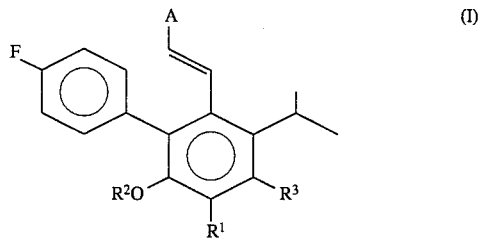

wherein A is a ω-oxycarbonyldihydroxybutyl group, a tetrahydropyranyl group, a ω-oxycarbonyl-3-oxobutyl group, a formyl group, or a cyano group; $R^1$ is a halogen atom, an alkyl group, or a group represented by $R^5O-$, wherein $R^5$ is a hydrogen atom, or an alkyl group; $R^2$ is a hydrogen atom, an alkyl group; $R^3$ is a hydrogen atom, or an alkyl group; $R^5$ and $R^2$ may form a five-membered ring or a six-membered ring in combination with the oxygen atoms to which $R^5$ and $R^2$ are respectively bonded, and $R^5$ and $R^3$ may form a five-membered ring or a six-membered ring in combination with the oxygen atom to which $R^5$ is bonded.

36 Claims, No Drawings

4-FLUOROBIPHENYL DERIVATIVES

BACKGROUND OF THE INVENTION

Field of the Invention

The present invention relates to a 4-fluorobiphenyl derivative of formula (I), which is useful as a cholesterol lowering agent or a lipid lowering agent because of its strong inhibitory effect on a 3-hydroxy-3-methylglutaryl-coenzyme A reductase (hereinafter referred to as HMG-CoA reductase) thereof, and which is also useful as an intermediate for producing the above-mentioned cholesterol lowering agent or lipid lowering agent:

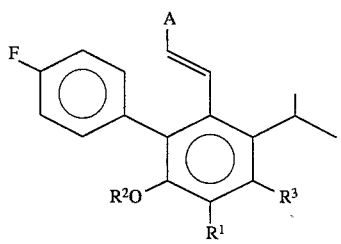

wherein A is a ω-oxycarbonyldihydroxybutyl group of formula (II):

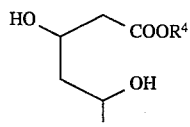

wherein $R^4$ is a hydrogen atom, an alkyl group having 1 to 6 carbon atoms, which may have a substituent, an alkaline metal or an alkaline earth metal;

a tetrahydropyranyl group of formula (III):

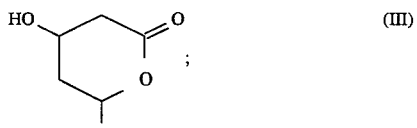

a ω-oxycarbonyl-3-oxobutyl group of formula (IV):

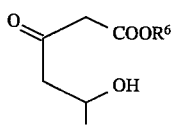

wherein $R^6$ is an alkyl group having 1 to 6 carbon atoms, which may have a substituent;

a formyl group; or a cyano group, $R^1$ is a halogen atom, an alkyl group having 1 to 6, which may have a substituent or a group represented by $R^5O$—, wherein $R^5$ is a hydrogen atom, an alkyl group having 1 to 6 carbon atoms, which may have a substituent; $R^2$ is a hydrogen atom, an alkyl group having 1 to 6 carbon atoms, which may have a substituent; $R^3$ is a hydrogen atom, or an alkyl group having 1 to 6 carbon atoms, which may have a substituent; $R^5$ and $R^2$ may form a five-membered ring or a six-membered ring in combination with the oxygen atoms to which $R^5$ and $R^2$ are respectively bonded, and $R^5$ and $R^3$ may form a five-membered ring or a six-membered ring in combination with the oxygen atom to which $R^5$ is bonded.

DISCUSSION OF BACKGROUND

ML-236B (Mevastatin) has been discovered as a compound which is capable of decreasing the concentration of cholesterol in the blood, which is considered to be a prominent factor for causing arteriosclerosis (refer to Japanese Laid-Open Patent Application 50-155690). ML- 236B inhibits the biosynthesis of cholesterol by its competitive inhibition against HMG-CoA reductase which serves as a rate-determining enzyme for the biosynthesis of cholesterol.

Furthermore, as the results of research of compounds which exhibit the effect of lowering the concentration of cholesterol in the blood, pravastatin which is a natural material or a derivative thereof (as disclosed in Japanese Laid-Open Patent Application 57-2240), simvastatin (U.S. Pat. No. 4,231,938) and lovastatin (U.S. Pat. 4,444,784) have been discovered and are used clinically in practice.

Furthermore, varieties of compounds have been synthesized in an attempt to obtain compounds having higher HMG-CoA reductase inhibition effect than those of drugs such as pravastatin, simvastatin, and lovastatin, for instance, as disclosed in Japanese Laid-Open Patent Application 56-45470, U.S. Pat. No. 4,375,475, Japanese Laid-Open Patent Application 58-8076, U.S. Pat. No. 4,459,422, U.S. Pat. No. 4,710,513, U.S. Pat. No. 4,567,289, U.S. Pat. No. 4,812,583, and German Laid-Open Patent 3909378.

The above-mentioned pravastatin, simvastatin, and lovastatin and other compounds disclosed in these references have HMG-CoA reductase inhibition effect and exhibit the effect of lowering the concentrations of cholesterol and lipids in the blood, but the effect is not satisfactory for use in practice, a drug which exhibits a much stronger effect of lowering the concentrations of cholesterol and lipids in the blood is desired.

SUMMARY OF THE INVENTION

It is therefore an object of the present invention to provide a compound which is useful as a drug which exhibits an unconventionally stronger effect of lowering the concentrations of cholesterol and lipids in the blood, and a compound which is also useful as an intermediate for producing the above-mentioned compound.

This object of the present invention is achieved by a 4-fluorobiphenyl derivative of the following formula (I):

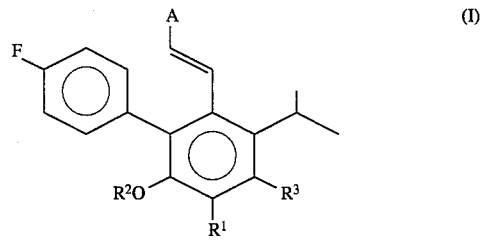

wherein A is a ω-oxycarbonyldihydroxybutyl group of formula (II):

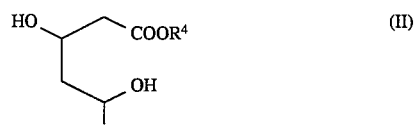

wherein $R^4$ is a hydrogen atom, an alkyl group having 1 to 6 carbon atoms, which may have a substituent, an alkaline metal or an alkaline earth metal;

a tetrahydropyranyl group of formula (III):

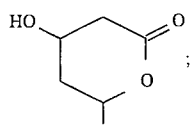

a ω-oxycarbonyl-3-oxobutyl group of formula (IV)

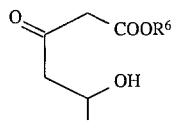

wherein $R^6$ is an alkyl group having 1 to 6 carbon atoms, which may have a substituent;

a formyl group; or a cyano group, $R^1$ is a halogen atom, an alkyl group having 1 to 6 carbon atoms, which may have a substituent, or a group represented by $R^5O—$, wherein $R^5$ is a hydrogen atom, an alkyl group having 1 to 6 carbon atoms, which may have a substituent; $R^2$ is a hydrogen atom, an alkyl group having 1 to 6 carbon atom, which may have a substituent; $R^3$ is a hydrogen atom, or an alkyl group having 1 to 6 carbon atoms, which may have a substituent; $R^5$ and $R^2$ may form a five-membered ring or a six-membered ring in combination with the oxygen atoms to which $R^5$ and $R^2$ are respectively bonded, and $R^5$ and $R^3$ may form a five-membered ring or a six-membered ring in combination with the oxygen atom to which $R^5$ is bonded.

DESCRIPTION OF THE PREFERRED EMBODIMENTS

In a 4-fluorobiphenyl derivative of formula (I) of the present invention, A is a ω-oxycarbonyldihydroxybutyl group of formula (II):

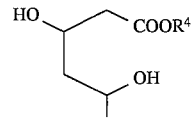

wherein $R^4$ is a hydrogen atom, an alkyl group having 1 to 6 carbon atoms, which may have a substituent, an alkaline, metal or an alkaline earth metal.

The alkyl group represented by $R^4$ is a straight or branched alkyl group having 1 to 6 carbon atoms, preferably an alkyl group having 1 to 4 carbon atoms, such as methyl group, ethyl group, n-propyl group, isopropyl group, n-butyl group, sec-butyl group, and t-butyl group.

Specific examples of the alkaline metal represented by $R^4$ include potassium, and sodium, and specific examples of the alkaline earth metal represented by $R^4$ include calcium and barium. These alkaline metals and alkaline earth metals can usually form salts in combination with carboxyl group.

In the ω-oxycarbonyl-3-oxobutyl group of formula (IV), $R^6$ is an alkyl group, which is the same alkyl group as represented by $R^4$ mentioned above.

$R^1$ is a halogen atom, an alkyl group having 1 to 6 carbon atoms, which may have a substituent, or a group represented by $R^5O—$, wherein $R^5$ is a hydrogen atom, an alkyl group having 1 to 6 carbon atoms, which may have a substituent.

Examples of a halogen atom represented by $R^1$ are fluorine, chlorine, bromine, and iodine.

The alkyl group represented by $R^1$ is the same as represented by $R^4$.

The alkyl group represented by $R^5$ is also the same as represented by $R^4$.

Examples of a substituent of the alkyl group having 1 to 6 carbon atoms, which may have a substituent, represented by $R^5$ include an alkoxyl group, a hydroxyl group, and an aralkyl group.

Specific examples of the alkyl group having 1 to 6 carbon atoms, substituted with an alkoxyl group, represented by $R^5$ include methoxymethyl group, methoxyethyl group, methoxypropyl group, ethoxyethyl group, ethoxypropyl group, methoxymethoxyethyl group, methoxyethoxyethyl group, and ethoxyethoxymethyl group.

Specific examples of the lower alkyl group having 1 to 6 carbon atoms, substituted with a hydroxyl group, represented by $R^5$ include hydroxyethyl group and hydroxypropyl group.

Specific examples of the aralkyl group represented by $R^5$ include an alkyl group having 1 to 6 carbon atoms to which an aromatic hydrocarbon group or a heteroaromatic ring is bonded, such as benzyl group, phenethyl group, 2-pyridylmethyl group, 3-pyridylmethyl group, 4-pyridylmethyl group, 2-pyridylethyl group, 3-pyridylethyl group, 4-pyridylethyl group, 2-pyridylpropyl group, furfuryl group, and 3-furylmethyl group.

$R^2$ is a hydrogen atom, an alkyl group having 1 to 6 carbon atoms, which may have a substituent, which is exactly the same as $R^5$.

$R^3$ is a hydrogen atom, or an alkyl group which is the same alkyl group as represented by $R^4$.

$R^5$ and $R^2$ may form a five-membered ring or a six-membered ring in combination with the oxygen atoms to which $R^5$ and $R^2$ are respectively bonded, such as a dioxolan ring, a dioxolan ring which is substituted with methyl group or ethyl group, a dioxane ring, or a dioxane ring which is substituted with methyl group or ethyl group.

$R^5$ and $R^3$ may form a five-membered ring or a six-membered ring in combination with the oxygen atom to which $R^5$ is bonded. Specific examples of such rings formed by $R^5$ and $R^3$ are a dihydrofuran ring, a dihydropyran ring, a methyl dihydrofuran ring, a dimethyl dihydrofuran ring, and a dimethyl dihydropyran ring.

As mentioned previously, according to the present invention, the above-mentioned 4-fluorobiphenyl derivative of formula (I) is useful as a cholesterol lowering agent or a lipid lowering agent, and also as an intermediate for producing such a cholesterol or lipid lowering agent.

More specifically, of various 4-fluorobiphenyl derivatives represented by the previously given formula (I), the following derivatives are particularly useful:

(1) A 4-fluorobiphenyl derivative of formula (I), in which A is a ω-oxycarbonyldihydroxybutyl group of formula (II):

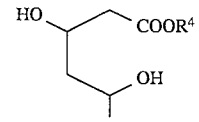

wherein $R^4$ is a hydrogen atom, an alkyl group having 1 to 6 carbon atoms, which may have a substituent, an alkaline metal or an alkaline earth metal.

(2) A 4-fluorobiphenyl derivative of formula (I), in which $R^1$ is a group represented by $R^5O—$, wherein $R^5$ is a hydrogen atom, or an alkyl group having 1 to 6 carbon atoms, which may have a substituent.

(3) A 4-fluorobiphenyl derivative of formula (I), in which $R^1$ is a halogen atom.

(4) A 4-fluorobiphenyl derivative of formula (I), in which $R^1$ is an alkyl group having 1 to 6 carbon atoms, which may have a substituent.

(5) A 4-fluorobiphenyl derivative of formula (I), in which $R^2$ is a hydrogen atom or an alkyl group having 1 to 6 carbon atoms, which may have a substituent.

(6) A 4-fluorobiphenyl derivative of formula (I), in which $R^1$ is a group represented by $R^5O$—, wherein $R^5$ is an alkyl group having 1 to 6 carbon atoms, which may have a substituent, and $R^5$ and $R^2$ form a five-membered ring or a six-membered ring in combination with the oxygen atoms to which $R^5$ and $R^2$ are respectively bonded.

(7) A 4-fluorobiphenyl derivative of formula (I), in which $R^1$ is a group represented by $R^5O$—, wherein $R^5$ is an alkyl group having 1 to 6 carbon atoms, which may have a substituent, and $R^5$ and $R^3$ may form a five-membered ring or a six-membered ring in combination with the oxygen atom to which $R^5$ is bonded.

(8) A 4-fluorobiphenyl derivative of formula (I), in which $R^3$ is a hydrogen atom.

(9) A 4-fluorobiphenyl derivative of formula (I), in which A is a ω-oxycarbonyldihydroxybutyl group of formula (II), and $R^4$ is an alkaline metal.

(10) A 4-fluorobiphenyl derivative of formula (I), in which $R^1$ is a group represented by $R^5O$—, wherein $R^5$ is an alkyl group having 1 to 6 carbon atoms, which may have a substituent.

(11) A 4-fluorobiphenyl derivative of formula (I), in which $R^1$ is a group represented by $R^5O$—, wherein $R^5$ is a hydrogen atom, an alkyl group having 1 to 6 carbon atoms, which may have a substituent; $R^2$ is an alkyl group having 1 to 6 carbon atom, which may have a substituent, and $R^4$ is an alkaline metal.

(12) A 4-fluorobiphenyl derivative of formula (I), in which $R^1$ is a group represented by $R^5O$—, wherein $R^5$ is an alkyl group having 1 to 6 carbon atoms, which may have a substituent; $R^2$ is an alkyl group having 1 to 6 carbon atom, which may have a substituent, and $R^4$ is an alkaline metal.

(13) A 4-fluorobiphenyl derivative of formula (I), in which $R^1$ is a group represented by $R^5O$—, wherein $R^5$ is a hydrogen atom, an alkyl group having 1 to 6 carbon atoms, which may have a substituent; $R^2$ is an alkyl group having 1 to 6 carbon atom, which may have a substituent, $R^3$ is a hydrogen atom, and $R^4$ is an alkaline metal.

(14) A 4-fluorobiphenyl derivative of formula (Ia):

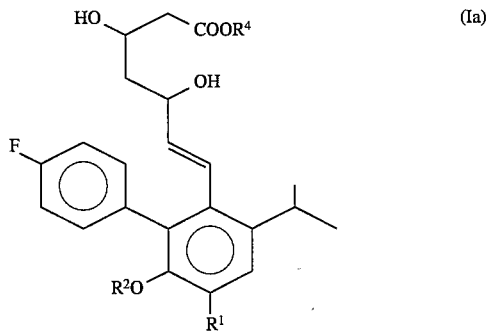

in which $R^1$ is a halogen atom, an alkyl group having 1 to 6 carbon atoms, which may have a substituent, or a group represented by $R^5O$—, wherein $R^5$ is an alkyl group having 1 to 6 carbon atoms, which may have a substituent; $R^2$ is an alkyl group having 1 to 6 carbon atom, which may have a substituent; $R^5$ and $R^2$ may form a five-membered ring or a six-membered ring in combination with the oxygen atoms to which $R^5$ and $R^2$ are respectively bonded; and $R^4$ is an alkyl group having 1 to 6 carbon atoms, which may have a substituent, or an alkaline metal.

(15) A 4-fluorobiphenyl derivative of formula (Ia), in which $R^1$ is a group represented by $R^5O$— wherein $R^5$ is an alkyl group having 1 to 6 carbon atoms, which may have a substituent; $R^2$ is an alkyl group having 1 to 6 carbon atom, which may have a substituent; and $R^4$ is an alkaline metal.

A 4-fluorobiphenyl derivative of the following formula (Ib) is also useful as an intermediate for producing the above-mentioned cholesterol or lipid lowering agent:

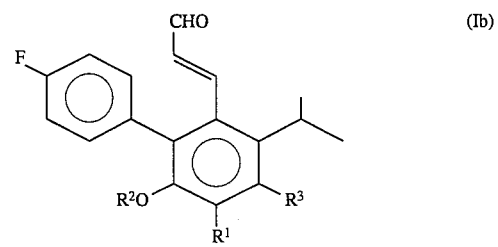

wherein $R^1$ is a halogen atom, an alkyl group having 1 to 6 carbon atoms, which may have a substituent, or a group re-presented by $R^5O$—, wherein $R^5$ is a hydrogen atom, an alkyl group having 1 to 6 carbon atoms, which may have a substituent; $R^2$ is a hydrogen atom, an alkyl group having 1 to 6 carbon atom, which may have a substituent; $R^3$ is a hydrogen atom, or an alkyl group having 1 to 6 carbon atoms, which may have a substituent; $R^5$ and $R^2$ may form a five-membered ring or a six-membered ring in combination with the oxygen atoms to which $R^5$ and $R^2$ are respectively bonded, $R^5$ and $R^3$ may form a five-membered ring or a six-membered ring in combination with the oxygen atom to which $R^5$ is bonded.

More specifically, of various 4-fluorobiphenyl derivatives represented by the above formula (Ib), the following 4-fluorobiphenyl derivatives are particularly useful as the intermediates:

(1) A 4-fluorobiphenyl derivative of formula (Ib), in which $R^1$ is a halogen atom, an alkyl group having 1 to 6 carbon atoms, which may have a substituent, or a group re-presented by $R^5O$—, wherein $R^5$ is a hydrogen atom, an alkyl group having 1 to 6 carbon atoms, which may have a substituent; $R^2$ is an alkyl group having 1 to 6 carbon atom, which may have a substituent; $R^3$ is a hydrogen atom.

(2) A 4-fluorobiphenyl derivative of formula (Ib), in which $R^1$ is a group represented by $R^5O$—, wherein $R^5$ is an alkyl group having 1 to 6 carbon atoms, which may have a substituent; $R^2$ is an alkyl group having 1 to 6 carbon atom, which may have a substituent.

A 4-fluorobiphenyl derivative of the following formula (Ic) is also useful as an intermediate for producing the above-mentioned cholesterol or lipid lowering agent:

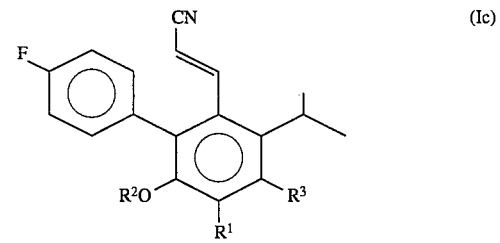

wherein $R^1$ is a halogen atom, an alkyl group having 1 to 6 carbon atoms, which may have a substituent, or a group re-presented by $R^5O$—, wherein $R^5$ is a hydrogen atom, an alkyl group having 1 to 6 carbon atoms, which may have a substituent; $R^2$ is a hydrogen atom, an alkyl group having 1 to 6 carbon atom which may have a substituent; $R^3$ is a hydrogen atom, or an alkyl group having 1 to 6 carbon atoms which may have a substituent; $R^5$ and $R^2$ may form a five-membered ring or a six-membered ring in combination with the oxygen atoms to which $R^5$ and $R^2$ are respectively bonded, $R^5$ and $R^3$ may form a five-membered ring or a six-membered ring in combination with the oxygen atom to which $R^5$ is bonded.

More specifically, of various 4-fluorobiphenyl derivatives represented by the above formula (Ib), the following 4-fluorobiphenyl derivatives are particularly useful as the intermediates:

(1) A 4-fluorobiphenyl derivative of formula (Ib), in which $R^1$ is a halogen atom, an alkyl group having 1 to 6 carbon atoms, which may have a substituent, or a group re-presented by $R^5O$—, wherein $R^5$ is a hydrogen atom, an alkyl group having 1 to 6 carbon atoms, which may have a substituent; $R^2$ is an alkyl group having 1 to 6 carbon atom which may have a substituent; $R^3$ is a hydrogen atom.

(2) A 4-fluorobiphenyl derivative of formula (Ib), in which $R^1$ is a group represented by $R^5O$—, wherein $R^5$ is an alkyl group having 1 to 6 carbon atoms, which may have a substituent; $R^2$ is an alkyl group having 1 to 6 carbon atom, which may have a substituent.

In particular, a 4-fluorobiphenyl derivative of the following formula (Id) is useful as a cholesterol lowering agent or a lipid lowering agent or an effective component thereof:

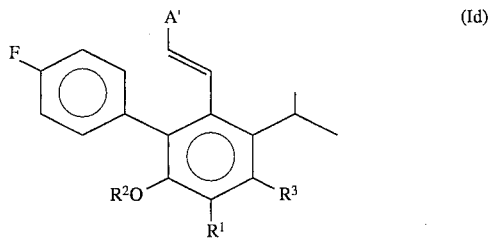

wherein A' is a ω-oxycarbonyldihydroxybutyl group of formula (II):

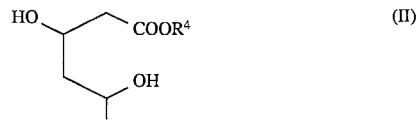

wherein $R^4$ is a hydrogen atom, an alkyl group having 1 to 6 carbon atoms, which may have a substituent, an alkaline metal or an alkaline earth metal; or a tetrahydropyranyl group of formula (III):

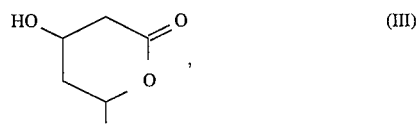

$R^1$ is a halogen atom, an alkyl group having 1 to 6 carbon atoms, which may have a substituent, or a group represented by $R^5O$—, wherein $R^5$ is a hydrogen atom, an alkyl group having 1 to 6 carbon atoms, which may have a substituent; $R^2$ is a hydrogen atom, an alkyl group having 1 to 6 carbon atom, which may have a substituent; $R^3$ is a hydrogen atom, or an alkyl group having 1 to 6 carbon atoms, which may have a substituent; $R^5$ and $R^2$ may form a five-membered ring or a six-membered ring in combination with the oxygen atoms to which $R^5$ and $R^2$ are respectively bonded, and $R^5$ and $R^3$ may form a five-membered ring or a six-membered ring in combination with the oxygen atom to which $R^5$ is bonded.

Of various 4-fluorobiphenyl derivatives represented by the formula (id), the following 4-fluorobiphenyl derivatives are particularly effective as an effective component for a cholesterol or lipid lowering agent:

(1) The cholesterol or lipid lowering agent comprising a 4-fluorobiphenyl derivative of formula (Id), in which A' is a ω-oxycarbonyl-dihydroxybutyl group of formula (II).

(2) The cholesterol or lipid lowering agent comprising a 4-fluorobiphenyl derivative of formula (Id), in which $R^1$ is a group represented by $R^5O$—, wherein $R^5$ is a hydrogen atom, or an alkyl group having 1 to 6 carbon atoms, which may have a substituent.

(3) The cholesterol or lipid lowering agent comprising a 4-fluorobiphenyl derivative of formula (Id), in which $R^1$ is a halogen atom.

(4) The cholesterol or lipid lowering agent comprising a 4-fluorobiphenyl derivative of formula (Id), in which $R^1$ is an alkyl group having 1 to 6 carbon atoms, which may have a substituent.

(5) The cholesterol or lipid lowering agent comprising a 4-fluorobiphenyl derivative of formula (Id), in which $R^2$ is a hydrogen atom.

(6) The cholesterol or lipid lowering agent comprising a 4-fluorobiphenyl derivative of formula (Id), in which $R^2$ is an alkyl group having 1 to 6 carbon atoms, which may have a substituent.

(6) The cholesterol or lipid lowering agent comprising a 4-fluorobiphenyl derivative of formula (Id), in which $R^1$ is a group represented by $R^5O$—, in which $R^5$ is an alkyl group having 1 to 6 carbon atoms, which may have a substituent, and $R^5$ and $R^2$ form a five-membered ring or a six-membered ring in combination with the oxygen atoms to which $R^5$ and $R^2$ are respectively bonded.

(7) The cholesterol or lipid lowering agent comprising a 4-fluorobiphenyl derivative of formula (Id), in which $R^1$ is a group represented by $R^5O$— wherein $R^5$ is an alkyl group having 1 to 6 carbon atoms, which may have a substituent, and $R^5$ and $R^3$ may form a five-membered ring or a six-membered ring in combination with the oxygen atom to which $R^5$ is bonded.

(8) The cholesterol or lipid lowering agent comprising a 4-fluorobiphenyl derivative of formula (Id), in which $R^3$ is a hydrogen atom.

(9) The cholesterol or lipid lowering agent comprising a 4-fluorobiphenyl derivative of formula (Id), in which $R^4$ is an alkaline metal.

(10) The cholesterol or lipid lowering agent comprising a 4-fluorobiphenyl derivative of formula (Id), in which $R^5$ is an alkyl group having 1 to 6 carbon atoms, which may have a substituent.

(11) The cholesterol or lipid lowering agent comprising a 4-fluorobiphenyl derivative of formula (Id), in which $R^1$ is a group represented by $R^5O$—, wherein $R^5$ is a hydrogen atom, or an alkyl group having 1 to 6 carbon atoms, which may have a substituent; $R^2$ is an alkyl group having 1 to 6 carbon atom, which may have a substituent, and $R^4$ is an alkaline metal.

(12) The cholesterol or lipid lowering agent comprising a 4-fluorobiphenyl derivative of formula (Id), in which $R^5$ is an alkyl group having 1 to 6 carbon atoms, which may have a substituent.

(13) The cholesterol or lipid lowering agent comprising a 4-fluorobiphenyl derivative of formula (Id), in which $R^3$ is a hydrogen atom.

A cholesterol or lipid lowering agent comprising a 4-fluorobiphenyl derivative of formula (Ia) is also useful:

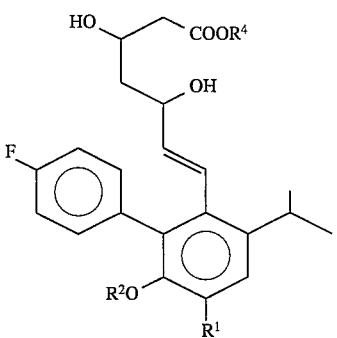

in which $R^1$ is a halogen atom, an alkyl group having 1 to 6 carbon atoms, which may have a substituent, or a group represented by $R^5O$—, wherein $R^5$ is an alkyl group having 1 to 6 carbon atoms, which may have a substituent; $R^2$ is an alkyl group having 1 to 6 carbon atom, which may have a substituent; $R^5$ and $R^2$ may form a five-membered ring or a six-membered ring in combination with the oxygen atoms to which $R^5$ and $R^2$ are respectively bonded; and $R^4$ is an alkyl group having 1 to 6 carbon atoms, which may have a substituent, or an alkaline metal.

In particular, a cholesterol or lipid lowering agent comprising a 4-fluorobiphenyl derivative of formula (Ia), in which $R^1$ is a group represented by $R^5O$—, wherein $R^5$ is an alkyl group having 1 to 6 carbon atoms, which may have a substituent; and $R^4$ is an alkaline metal, is particularly effective.

Specific examples of the 4-fluorobiphenyl derivative represented by formula (I) are as follows:

Sodium (E)-7-[4'-fluoro-6-hydroxy-5-methoxy-3-(propan-2-yl)biphenyl- 2-yl]-3,5-dihydroxy-6-heptenoate, Sodium (E)-7-[4'-fluoro-5,6-dimethoxy-3-(propan-2-yl)biphenyl- 2-yl]-3,5-dihydroxy-6-heptenoate, Sodium (E)-7-[4'-fluoro-6-(2-hydroxyethoxy)-5-methoxy-3-(propan- 2-yl)biphenyl-2-yl]-3,5-dihydroxy-6-heptenoate, Sodium (E)-7-[4'-fluoro-5-methoxy-6-(2-methoxyethoxy)-3-(propan- 2-yl)biphenyl-2-yl]-3,5-dihydroxy-6-heptenoate, Sodium (E)-7-[4'-fluoro-5-methoxy-6-[2-(2-methoxyethoxy)ethoxy]- 3-(propan-2-yl)biphenyl-2-yl]-3,5-dihydroxy- 6-heptenoate, Sodium (E)-7-[4'-fluoro-5-methoxy-3-(propan-2-yl) -6 -(2-pyridylmethyl)biphenyl- 2-yl]-3,5-dihydroxy-6-heptenoate, Sodium (E)-7-[4'-fluoro-5-methoxy-3-(propan-2-yl)-6-(3-pyridylmethyloxy)biphenyl- 2-yl]-3,5-dihydroxy-6-heptenoate, Sodium (E)-7-[4'-fluoro-5-methoxy-3-(propan-2-yl)-6-(4-pyridylmethyloxy)biphenyl- 2-yl]-3,5-dihydroxy-6-heptenoate, Sodium (E)-7-[4'-fluoro-5-(2-hydroxyethoxy)-6-methoxy-3-(propan- 2-yl)biphenyl-2-yl]-3,5-dihydroxy-6-heptenoate, Sodium (E) -7-[4'-fluoro-6-methoxy-5-(2-methoxyethoxy)-3-(propan- 2-yl)biphenyl-2 -yl]-3,5-dihydroxy-6-heptenoate, Sodium (E)-7-[4'-fluoro-6-methoxy-5-[2-(2-methoxyethoxy)ethoxy]- 3-(propan-2-yl)biphenyl-2-yl]-3,5-dihydroxy- 6-heptenoate, Sodium (E)-7-[7-benzyloxy-6-(4'-fluorophenyl)-2,3-dihydro- 2,2-dimethyl-4-(propan-2-yl)benzo[b ]furan-5yl]-3,5-dihydroxy-6-heptenoate, Sodium (E)-7-[6-(4'-fluorophenyl)-2,3-dihydro-7-hydroxy- 2,2-dimethyl-4-(propan-2-yl) benzo[b]furan-5-yl]-3, 5-dihydroxy- 6-heptenoate, Sodium (E)-7-[6-(4'-fluorophenyl)-2,3-dihydro-7-[2-(2-methoxyethoxy)ethoxy]- 2,2-dimethyl-4-(propan-2-yl)benzo [b]furan-5-yl]-3,5-dihydroxy-6-heptenoate, Sodium (E)-7-[6-(4'-fluorophenyl)-2,3-dihydro-2,2-dimethyl- 4-(propan-2-yl) -7-(2-pyridylmethyloxy)benzo[b]furan-5-yl]-3,5-dihydroxy-6-heptenoate, Sodium (E)-7-[6-(4'-fluorophenyl)-2,3-dihydro-2,2-dimethyl- 4-(propan-2-yl)-7-(3-pyridylmethyloxy)benzo[b]furan-5-yl]-3,5-dihydroxy-6-heptenoate, Sodium (E)-7-[5,6-diethoxy-4'-fluoro-3-(propan-2-yl)biphenyl- 2-yl]-3,5 -dihydroxy-6 -heptenoate, Sodium (E)-7-[4'-fluoro-5,6-di(2-hydroxyethoxy)-3-(propan- 2-yl)biphenyl-2 -yl]-3,5-dihydroxy-6-heptenoate, Sodium (E)-7-[4'-fluoro-5,6-di(2-methoxyethoxy)-3-(propan- 2-yl)biphenyl-2,yl]-3,5-dihydroxy-6-heptenoate, Sodium (E)-7-[4'-fluoro-5,6-methylenedioxy-3-(propan-2-yl)biphenyl- 2-yl]-3,5-dihydroxy-6-heptenoate, Sodium (E)-7-[5-(4'-fluorophenyl)-7-(propan-2-yl)-1,4-benzodioxan- 6 -yl]-3,5 -dihydroxy-6 -heptenoate, Sodium (E)-7-[4'-fluoro-5,6-dimethylmethylenedioxy-3-(propan- 2-yl)biphenyl-2-yl]-3,5-dihydroxy-6 -heptenoate, Sodium (E)-7-[4'-fluoro-6-methoxy-5-methyl-3-(propan-2-yl)biphenyl- 2-yl]-3,5-dihydroxy-6-heptenoate, Sodium (E)-7-[5-ethyl-4'-fluoro-6-methoxy-3-(propan-2-yl)biphenyl- 2-yl]-3,5-dihydroxy-6-heptenoate, Sodium (E)-7-[4',5-difluoro-6-methoxy-3-(propan-2-yl)biphenyl- 2-yl]-3,5-dihydroxy-6-heptenoate, Sodium (E)-7-[5-chloro-4'-fluoro-6-methoxy-3-(propan-2-yl)biphenyl- 2-yl]-3,5-dihydroxy-6-heptenoate, Sodium (E)-7-[5-bromo-4'-fluoro-6-methoxy-3-(propan-2-yl)biphenyl- 2-yl]-3,5-dihydroxy-6-heptenoate, Sodium (E)-7-[4'-fluoro-5-iodo-6-methoxy-3-(propan-2-yl)biphenyl- 2-yl]-3,5-dihydroxy-6-heptenoate, Ethyl (E)-7-[4'-fluoro-6-hydroxy-5-methoxy-3-(propan-2-yl)biphenyl)- 2-yl]-3,5-dihydroxy-6-heptenoate, Ethyl (E)-7-[4'-fluoro-5,6-dimethoxy-3-(propan-2-yl)biphenyl- 2-yl]-3,5 -dihydroxy-6 -heptenoate, Ethyl (E)-7-[4'-fluoro-6-(2-hydroxyethoxy)-5-methoxy-3-(propan- 2 -yl)biphenyl-2 -yl]-3,5-dihydroxy-6 -heptenoate, Ethyl (E)-7-[4'-fluoro-5-methoxy-6-(2-methoxyethoxy)-3-(propan- 2-yl)biphenyl-2-yl]-3,5-dihydroxy-6-heptenoate, Ethyl (E)-7-[4'-fluoro-5-methoxy-6-[2-(2-methoxyethoxy)ethoxy ]-3-(propan-2-yl)biphenyl-2-yl]-3,5-dihydroxy-6-heptenoate, Ethyl (E)-7-[4'-fluoro-5-methoxy-3-(propan-2-yl)-6-(2-pyridylmethyloxy)biphenyl- 2-yl]-3,5-dihydroxy-6heptenoate, Ethyl (E)-7-[4'-fluoro-5-methoxy-3-(propan-2-yl)-6-(3-pyridylmethyloxy)biphenyl- 2 -yl]-3,5 -dihydroxy-6-heptenoate, Ethyl (E)-7-[4'-fluoro-5-methoxy-3-(propan-2-yl)-6-(4pyridylmethyloxy)biphenyl- 2 -yl]-3,5 -dihydroxy-6-heptenoate, Ethyl (E)-7-[4'-fluoro-5-(2-hydroxyethoxy)-6-methoxy-3-(propan- 2-yl)biphenyl-2-yl]-3,5-dihydroxy-6-heptenoate, Ethyl (E)-7-[4'-fluoro-6-methoxy-5-(2-methoxyethoxy)-3( propan-2-yl)biphenyl-2-yl]-3,5-dihydroxy-6-heptenoate, Ethyl (E)-7-[4'-fluoro-6-methoxy-5-[2-(2-methoxyethoxy)ethoxy- 3-(propan-2-yl)biphenyl-2-yl]-3,5-dihydroxy-6-heptenoate, Ethyl (E)-7-[7-benzyloxy-6-(4'-fluorophenyl)-2,3-dihydro- 2,2-dimethyl-4-(propan-2-yl)benzo[b]furan-5-yl]-3,5-dihydroxy- 6 -heptenoate, Ethyl (E)-7-[6-(4'-fluorophenyl)-2,3-dihydro-7-hydroxy-2,2-dimethyl-4-(propan-2-yl) benzo[b]furan-5-yl]-3,5-dihydroxy- 6 -heptenoate, Ethyl (E)-7-[6-(4'-fluorophenyl)-2,3-dihydro-7-[2-(2-methoxyethoxy)ethoxy]- 2,2-dimethyl-4-(propan-2-yl)benzo[b]furan-5-yl]-3,5-dihydroxy-6-heptenoate, Ethyl (E)-7-[6-(4'-fluorophenyl)-2,3-dihydro-2,2-dimethyl- 4-(propan-2-yl)-7-(2-pyridylmethyloxy) benzo-[b]furan-5-yl]-3,5-dihydroxy-6-heptenoate, Ethyl (E)-7-[6-(4'-fluorophenyl)-2,3-dihydro-2,2-dimethyl- 4-(propan-2-yl)-7-(3-pyridylmethyloxy) benzo[b]furan-5-yl]-3,5-dihydroxy-6-heptenoate, Ethyl (E)-7-[5,6-diethoxy-4'-fluoro-3-(propan-2-yl)biphenyl- 2-yl]-3,5-dihydroxy-6-heptenoate, Ethyl (E)-7-[4'-fluoro-5,6-di(2-hydroxyethoxy)-3-(propan- 2-yl)biphenyl-2-yl]-3,5-dihydroxy-6-heptenoate, Ethyl (E)-7-[4'-fluoro-5,6-di (2-methoxyethoxy)-3-(propan- 2-yl)biphenyl-2-yl]-3,5-dihydroxy-6-heptenoate, Ethyl (E)-7-[4'-fluoro-5,6-methylenedioxy-3-(propan-2-yl)biphenyl- 2-yl]-3,5-dihydroxy-6-heptenoate, Ethyl (E)-7-[5-(4'-fluorophenyl)-7-(propan-2-yl)-1,4-benzodioxan- 6-yl]-3,5-dihydroxy-6-heptenoate, Ethyl (E)-7-[4'-fluoro-5,6-dimethylmethylenedioxy-3(propan- 2-yl)biphenyl-2-yl]-3,5-dihydroxy-6-heptenoate, Ethyl (E)-7 - [4'-fluoro-6-methoxy-5-methyl-3-(propan-2-yl)biphenyl- 2-yl]-3,5-dihydroxy-6-heptenoate, Ethyl (E)-7-[5-ethyl-4'-fluoro-6-methoxy-3-(propan-2-yl)biphenyl- 2-yl]-3,5-dihydroxy-6-heptenoate, Ethyl (E)-7-[4',5-difluoro-6-methoxy-3-(propan-2-yl)biphenyl- 2-yl]-3,5-dihydroxy-6-heptenoate, Ethyl (E)-7-[5-chloro-4'-fluoro-6-methoxy-3-(propan-2-yl)biphenyl- 2-yl]-3,5-dihydroxy-6-heptenoate, Ethyl (E)-7-[5-bromo-4'-fluoro-6-methoxy-3-(propan-2-yl)biphenyl- 2-yl]-3,5-dihydroxy-6-heptenoate, Ethyl (E)-7-[4'-fluoro-5-iodo-6-methoxy-3-(propan-2-yl)biphenyl- 2-yl]-3,5-dihydroxy-6-heptenoate, trans-(+)-6-[(E)-2-[4'-fluoro-6-hydroxy-5-methoxy-3-(propan- 2-yl)biphenyl-2-yl]ethenyl]-4-hydroxytetrahydropyran- 2-one, trans-(+)-6-[(E)-2-[4'-fluoro-5,6-dimethoxy-3-(propan-2-yl)biphenyl- 2-yl)ethenyl]-4-hydroxytetrahydropyran-2-one trans-(+)-6-[(E)-2-[4'-fluoro-6-(2-hydroxyethoxy)-5-methoxy- 3-(propan-2-yl)biphenyl-2-yl]ethenyl]-4-hydroxytetrahydropyran- 2-one, trans-(+)-6-[(E)-2-[4'-fluoro-5-methoxy-6-(2-methoxyethoxy)- 3-(propan-2-yl)biphenyl-2-yl]ethenyl]4-hydroxytetrahydropyran-2 -one, trans-(+)-6-[(E)-2-[4'-fluoro-5-methoxy-6-[2-(2-methoxyethoxy)ethoxy]- 3-(propan-2-yl)biphenyl-2-yl]ethenyl]-4-hydroxytetrahydropyran-2-one, trans-(±)-6-[(E)-2-[4'-fluoro-5-methoxy-3-(propan-2-yl)-6-(2-pyridylmethyloxy)biphenyl-2-yl]ethenyl]-4-hydroxytetrahydropyran- 2-one, trans-(+)-6-[(E)-2-[4'-fluoro-5-methoxy-3-(propan-2-yl)-6-(3-pyridylmethyloxy)biphenyl-2-yl]ethenyl]-4-hydroxytetrahydropyran- 2-one, trans-(+)-6-[(E)-2-[4'-fluoro-5-methoxy-3-(propan-2-yl)-6-(4-pyridylmethyloxy)biphenyl-2-yl]ethenyl]-4-hydroxytetrahydropyran- 2-one, trans-(+)-6-[(E)-2-[4'- fluoro-5-(2-hydroxyethoxy)-6-methoxy- 3-(propan-2-yl)biphenyl-2-yl]ethenyl]-4-hydroxytetrahydropyran- 2-one, trans-(+)-6-[(E)-2-[4'-fluoro-6-methoxy-5-(2-methoxyethoxy)- 3-(propan-2-yl)biphenyl-2-yl]ethenyl]-4-hydroxytetrahydropyran- 2-one, trans-(+)-6-[(E)-2-[4'-fluoro-6-methoxy-5-[2-(2-methoxyethoxy)ethoxy]- 3-(propan-2-yl)biphenyl-2-yl]ethenyl]-4-hydroxytetrahydropyran-2-one, trans-(+)-6-[(E)-2-[7-benzyloxy-6-(4'-fluorophenyl)-2,3-dihydro- 2,2-dimethyl-4-(propan-2-yl)benzo[b]furan-5-yl] ethenyl]- 4-hydroxytetrahydropyran-2 -one, trans-(+)-6-[(E)-2-[6-(4'-fluorophenyl)-2,3-dihydro-7-hydroxy- 2,2-dimethyl-4-(propan.-2-yl) benzo[b]furan-5-yl] ethenyl]- 4-hydroxytetrahydropyran-2 -one, trans-(+)-6-[(E)-2-[6-(4'-fluorophenyl)-2,3-dihydro-7-[2-( 2-methoxyethoxy) ethoxy ]-2,2-dimethyl-4-(propan-2-yl)benzo[b]furan-5-yl]ethenyl]-4-hydroxytetrahydropyran-2-one, trans-(+)-6-[(E)-2-[6-(4'-fluorophenyl)-2,3-dihydro-2,2-dimethyl- 4-(propan-2-yl)-7-(2-pyridylmethyloxy)benzo[b]furan-5-yl]ethenyl]-4-hydroxytetrahydropyran-2-one, trans-(+)-6-[(E)-2-[6-(4'-fluorophenyl)-2,3-dihydro-2,2-dimethyl- 4-(propan-2-yl)-7-(3-pyridylmethyloxy) benzo[b]furan-5-yl]ethenyl]-4-hydroxytetrahydropyran-2-one trans-(+)-6-[(E)-2-[5,6-diethoxy-4'-fluoro-3-(propan-2-yl)biphenyl- 2-yl]ethenyl]-4-hydroxytetrahydropyran-2-one trans-(+)-6-[(E)-2-[4'- fluoro-5,6-di(2-hydroxyethoxy)-3-(propan- 2-yl)biphenyl-2-yl]ethenyl]-4-hydroxytetrahydropyran- 2-one, trans-(+)-6-[(E)-2-[4'-fluoro-5,6-di(2-methoxyethoxy)-3-(propan- 2-yl)biphenyl-2-yl]ethenyl]-4-hydroxytetrahydropyran- 2-one, trans-(+)-6-[(E)-2-[4'-fluoro-5,6-methylenedioxy-3-(propan- 2-yl)biphenyl-2-yl]ethenyl]-4-hydroxytetrahydropyran- 2-one, trans-(+)-6-[(E)-2-[5-(4'-fluorophenyl)-7-(propan-2-yl)-1,4-benzodioxan-6-yl]ethenyl]-4-hydroxytetrahyropyran-12-one, trans-(+)-6-[(E)-2-[4'-fluoro-5,6-dimethylmethylenedioxy- 3-(propan-2-yl)biphenyl-2-yl]ethenyl]-4-hydroxytetrahydropyran- 2-one, trans-(+)-6-[(E)-2-[4'-fluoro-6-methoxy-5-methyl-3-(propan- 2-yl)biphenyl-2-yl] ethenyl]-4-hydroxytetrahydropyran- 2-one, trans-(+)-6-[(E)-2-[5-ethyl-4'-fluoro-6-methoxy-3-(propan- 2-yl)biphenyl-2-yl]ethenyl]-4-hydroxytetrahydropyran- 2-one, trans-(+)-6-[(E)-2-[4',5-difluoro-6-methoxy-3-(propan-2-yl)biphenyl- 2-yl]ethenyl]-4-hydroxytetrahydropyran-2one, trans-(+)-6-[(E)-2-[5-chloro-4'-fluoro-6-methoxy-3-(propan- 2-yl)biphenyl-2-yl]ethenyl]-4-hydroxytetrahydropyran- 2-one, trans-(+)-6-[(E)-2-[5-bromo-4'-fluoro-6-methoxy-3-(propan- 2-yl)biphenyl-2-yl]ethenyl]-4-hydroxytetrahydropyran- 2-one, trans-(+)-6-[(E)-2-[4'-fluoro-5-iodo-6-methoxy-3-(propan- 2-yl)biphenyl-2-yl]ethenyl]-4-hydroxytetrahydropyran- 2 -one, Ethyl (E)-7-[4'-fluoro-6-hydroxy-5-methoxy-3-(propan-2-yl)biphenyl- 2-yl]-5-hydroxy-3-oxo-6-heptenoate, Ethyl (E)-7-[4'-fluoro-5,6-dimethoxy-3-(propan-2-yl)biphenyl- 2-yl]-5-hydroxy-3-oxo-6-heptenoate, Ethyl (E)-7-[4'-fluoro-6-(2-hydroxyethoxy)-5-methoxy-3-(propan- 2-yl)biphenyl-2-yl]-5-hydroxy-3-oxo-6-heptenoate, Ethyl (E)-7-[4'-fluoro-5-methoxy-6-(2-methoxyethoxy)-3-(propan- 2-yl)biphenyl-2-yl]-5-hydroxy-3-oxo-6-heptenoate, Ethyl (E)-7-[4'-fluoro-5-methoxy-6-[2-(2-methoxyethoxy)ethoxy]-3-(propan-2-yl)biphenyl-2-yl]-5-hydroxy-3-oxo- 6-heptenoate, Ethyl (E)-7-[4'-fluoro-5-methoxy-3-(propan-2-yl)-6-(2-pyridylmethyloxy)biphenyl- 2-yl]-5-hydroxy-3 -oxo-6-heptenoate, Ethyl (E)-7-[4'-fluoro-5-methoxy-3-(propan-2-yl)-6-(3-pyridylmethyloxy)biphenyl- 2-yl]-5-hydroxy-3-oxo-6-heptenoate, Ethyl (E)-7-[4'-fluoro-5-methoxy-3-(propan-2-yl)-6-(4-pyridylmethyloxy)biphenyl- 2-yl]-5-hydroxy-3-oxo -6-heptenoate, Ethyl (E)-7-[4'-fluoro-5-(2-hydroxyethoxy)-6-methoxy-3-(propan- 2-yl)biphenyl-2-yl]-5-hydroxy-3-oxo-6-heptenoate, Ethyl (E)-7-[4'-fluoro-6-methoxy-5-(2-methoxyethoxy)-3-(propan- 2 -yl)biphenyl-2 -yl]-5 -hydroxy-3 -oxo-6-heptenoate, Ethyl (E)-7-[4'-fluoro-6-methoxy-5-[2-(2-methoxyethoxy )ethoxy ]-3-(propan-2-yl)biphenyl-2-yl]-5-hydroxy-3-oxo- 6-heptenoate, Ethyl (E)-7-[7-benzyloxy-6-(4'-fluorophenyl)-2,3-dihydro- 2,2-dimethyl-4-(propan-2-yl) benzo[b]furan-5-yl]-5-hydroxy- 3-oxo-6-heptenoate, Ethyl (E)-7-[6-(4'-fluorophenyl)-2,3-dihydro-7-hydroxy-2,2-dimethyl-4-(propan-2-yl) benzo[b]furan-5-yl]-5-hydroxy- 3-oxo-6-heptenoate, Ethyl (E)-7-[6-(4'-fluorophenyl)-2,3-dihydro-7-[2-(2-methoxyethoxy)ethoxy]- 2,2-dimethyl-4 -(propan-2-yl )benzo[b]furan-5-yl]-5-hydroxy-3-oxo-6-heptenoate, Ethyl (E)-7-[6-(4'-fluorophenyl)-2,3-dihydro-2,2-dimethyl- 4-(propan-2-yl)-7-(2-pyridylmethyloxy)benzo [b]furan-5-yl]-5-hydroxy-3-oxo-6-heptenoate, Ethyl (E)-7-[6-(4'-fluorophenyl)-2,3-dihydro-2,2-dimethyl- 4-(propan-2-yl)-7 -(3-pyridylmethyloxy)benzo[b]furan-5-yl]-5-hydroxy-3-oxo-6-heptenoate, Ethyl (E)-7-[5,6-diethoxy-4'-fluoro-3-(propan-2-yl)biphenyl- 2-yl]-5-hydroxy-3-oxo-6-heptenoate, Ethyl (E)-7-[4'-fluoro-5,6-di(2-hydroxyethoxy)-3-(propan- 2-yl)biphenyl-2-yl]-5-hydroxy-3-oxo-6-heptenoate, Ethyl (E)-7-[4'-fluoro-5,6-di (2-methoxyethoxy)-3-(propan- 2-yl)biphenyl-2-yl]-5-hydroxy-3-oxo-6-heptenoate, Ethyl (E)-7-[4'-fluoro-5,6-methylenedioxy-3-(propan-2-yl)biphenyl- 2-yl]-5-hydroxy-3-oxo-6-heptenoate, Ethyl (E)-7-[5-(4'-fluorophenyl)-7-(propan-2-yl)-1,4-benzodioxan- 6-yl]-5-dihydroxy-3-oxo -6-heptenoate, Ethyl (E)-7-[4'-fluoro-5,6-dimethylmethylenedioxy-3- (propan- 2-yl)biphenyl-2-yl]-5-hydroxy-3-oxo-6-heptenoate, Ethyl (E)-7-[4'-fluoro-6-methoxy-5-methyl-3-(propan-2-yl)biphenyl- 2-yl]-5-hydroxy-3-oxo-6-heptenoate, Ethyl (E)-7-[5-ethyl-4'-fluoro-6-methoxy-3-(propan-2-yl )biphenyl, 2 -yl]-5 -hydroxy-3 -oxo -6 -heptenoate, Ethyl (E)-7-[4',5-difluoro-6-methoxy-3-(propan-2-yl)biphenyl- 2-yl]-5-hydroxy-3-oxo-6-heptenoate, Ethyl (E)-7-[5-chloro-4'-fluoro-6-methoxy-3-(propan-2-yl)biphenyl- 2-yl]-5-hydroxy-3-oxo-6-heptenoate, Ethyl (E)-7-[5-bromo-4'-fluoro-6-methoxy-3-(propan-2-yl)biphenyl- 2 -yl]-5 -hydroxy-3 - oxo -6 -heptenoate, Ethyl (E)-7-[4'-fluoro-5-iodo-6-,methoxy-3-(propan-2-yl)biphenyl- 2 -yl]-5 -hydroxy-3 -oxo-6 -heptenoate, (E)-3-[4'-fluoro-6-hydroxy-5-methoxy-3-(propan-2-yl )biphenyl- 2-yl]-2-propenal, (E)-3-[4'-fluoro-5,6-dimethoxy-3-(propan-2-yl)biphenyl-2-yl]-2-propenal, (E)-3-[4'-fluoro-6-(2-hydroxyethoxy)-5-methoxy-3-(propan- 2-yl)biphenyl-2-yl]-2-propenal, (E)-3-[4'-fluoro-5-methoxy-6-(2-methoxyethoxy)-3-(propan- 2-yl)biphenyl-2-yl]-2-propenal, (E)-3-[4'-fluoro-5-methoxy-6-[2-(2-methoxyethoxy )ethoxy]- 3-(propan-2-yl)biphenyl-2-yl]-2-propenal, (E)-3-[4'-fluoro-5-methoxy-3-(propan-2-yl)-6-(2-pyridylmethyloxy)biphenyl- 2-yl]-2-propenal, (E)-3-[4'-fluoro-5-methoxy-3-(propan-2-yl)-6-(3-pyridylmethyloxy)biphenyl- 2-yl]-2-propenal, (E)-3-[4'-fluoro-5-methoxy-3-(propan-2-yl)-6-(4-pyridylmethyloxy)biphenyl- 2-yl]-2-propenal, (E)-3-[4'-fluoro-5-(2-hydroxyethoxy)-6-methoxy-3-(propan- 2-yl)biphenyl-2-yl]-2-propenal, (E)-3-[4'-fluoro-6-methoxy-5-(2-methoxyethoxy)-3-(propan- 2-yl)biphenyl-2-yl]-2-propenal, (E)-3-[4'-fluoro-6-methoxy-5-[2-(2-methoxyethoxy )ethoxy]- 3-(propan-2-yl)biphenyl-2-yl]-2-propenal, (E)-3-[7-benzyloxy-6-(4'-fluorophenyl)-2,3-dihydro-2,2-dimethyl- 4-(propan-2-yl)benzo[b]furan-5-yl]-2-propenal, (E)-3-[6-(4'-fluorophenyl)-2,3-dihydro-7-hydroxy-2,2-dimethyl- 4-(propan-2-yl)benzo[b]furan-5-yl]-2-propenal, (E)-3-[6-(4'-fluorophenyl)-2,3-dihydro-7-[2-(2-methoxyethoxy)ethoxy]-2,2-dimethyl-4-(propan-2-yl)benzo[b]-furan- 5-yl]-2-propenal, (E)-3-[6-(4'-fluorophenyl)-2,3-dihydro-2,2-dimethyl-4-(propan- 2-yl)-7-(2-pyridylmethyloxy)benzo[b]furan-5-yl]-2-propenal, (E)-3-[6-(4'-fluorophenyl)-2,3-dihydro-2,2-dimethyl-4-(propan- 2-yl)-7-(3-pyridylmethyloxy)benzo[b]furan-5-yl]-2-propenal, (E)-3-[5,6-diethoxy-4'-fluoro-3-(propan-2-yl)biphenyl-2-yl]-2-propenal, (E)-3-[4'-fluoro-5,6-di(2-hydroxyethoxy)-3-(propan-2-yl)biphenyl- 2-yl]-2-propenal, (E)-3-[4'-fluoro-5,6-di(2-methoxyethoxy)-3-(propan-2-yl)biphenyl- 2-yl]-2-propenal, (E)-3-[4'-fluoro-5,6-methylenedioxy-3-(propan-2-yl)biphenyl- 2-yl]-2-propenal, (E)-3-[5-(4'-fluorophenyl)-7-(propan-2-yl)-1,4-benzodioxan- 6-yl]-2-propenal, (E)-3-[4'-fluoro-5,6-dimethylmethylenedioxy-3-(propan-2-yl)biphenyl- 2-yl]-2-propenal, (E)-3-[4'-fluoro-6-methoxy-5-methyl-3-(propan-2-yl)biphenyl- 2-yl]-2-propenal, (E)-3-[5-ethyl-4'-fluoro-6-methoxy-3-(propan-2-yl)biphenyl- 2-yl]-2-propenal, (E)-3-[4',5-difluoro-6-methoxy-3-(propan-2-yl)biphenyl-2-yl]-2-propenal, (E)-3-[5-chloro-4'-fluoro-6-methoxy-3-(propan-2-yl)biphenyl- 2-yl]-2-propenal, (E)-3-[5-bromo-4'-fluoro-6-methoxy-3-(propan-2-yl)biphenyl- 2-yl]-2-propenal, (E)-3-[4'-fluoro-5 -iodo-6-methoxy-3-(propan-2-yl)biphenyl- 2-yl]-2-propenal, (E)-3-[4'-fluoro-6 -hydroxy-5-methoxy-3-(propan-2-yl )biphenyl- 2 -yl]-2-propenenitrile, (E)-3-[4'-fluoro-5,6-dimethoxy-3-(propan-2-yl)biphenyl-2-yl]-2-propenenitrile, (E)-3-[4'-fluoro-6-(2-hydroxyethoxy)-5-methoxy-3-(propan- 2-yl)biphenyl-2-yl]-2-propenenitrile, (E)-3-[4'-fluoro-5-methoxy-6-(2-methoxyethoxy)-3-(propan- 2 -yl)biphenyl-2-yl]-2-propenenitrile, (E)-3-[4'-fluoro-5-methoxy-6-[2-(2-methoxyethoxy )ethoxy]- 3-(propan-2-yl)biphenyl-2-yl]-2-propenenitrile, (E)-3-[4'-fluoro-5-methoxy-3-(propan-2-yl)-6-(2-pyridylmethyloxy)biphenyl 2 -yl]-2 -propenenitrile, (E)-3-[4'-fluoro-5-methoxy-3-(propan-2-yl)-6-(3-pyridylmethyloxy)biphenyl- 2 -yl]-2 -propenenitrile, (E)-3-[4'-fluoro-5-methoxy-3-(propan-2-yl)-6-(4-pyridylmethyloxy)biphenyl- 2-yl]-2-propenenitrile, (E)-3- [4'- fluoro-5-(2-hydroxyethoxy)-6-methoxy-3-(propan- 2-yl)biphenyl-2-yl]-2-propenenitrile, (E)-3- [4'- fluoro-6-methoxy-5-(2-methoxyethoxy)-3-(propan- 2-yl)biphenyl-2-yl]-2-propenenitrile, (E)-3-[4'-fluoro-6-methoxy-5-[2-(2-methoxyethoxy )ethoxy]- 3-(propan-2-yl)biphenyl-2-yl]-2-propenenitrile, (E)-3-[7-benzyloxy-6-(4'-fluorophenyl)-2,3-dihydro-2,2-dimethyl- 4-(propan-2-yl)benzo[b ] furan-5-yl]-2-propenenitrile, (E)-3-[6-(4'-fluorophenyl)-2,3-dihydro-7-hydroxy-2,2-dimethyl- 4-(propan-2-yl) benzo[b]furan-5-yl]-2-propenenitrile, (E)-3- [6-(4'- fluorophenyl)-2,3-dihydro-7 - [2-(2-methoxyethoxy)ethoxy]- 2,2-dimethyl-4-(propan-2-yl) benzo[b]-furan- 5-yl]-2-propenenitrile, (E)-3-[6-(4'-fluorophenyl)-2,3-dihydro-2,2'-dimethyl-4-(propan- 2-yl)-7 -(2-pyridylmethyloxy) benzo[b]furan-5-yl ]-2-propenenitrile, (E)-3-[6-(4'-fluorophenyl)-2,3-dihydro-2,2-dimethyl-4-(propan- 2-yl)-7-(3-pyridylmethyloxy) benzo[b]furan-5-yl ]-2-propenenitrile, (E)-3-[5,6-diethoxy-4'-fluoro-3-(propan-2-yl)biphenyl-2-yl ]-2-propenenitrile, (E)-3-[4'-fluoro-5,6-di(2-hydroxyethoxy)-3-(propan-2-yl)biphenyl- 2-yl]-2-propenenitrile, (E)-3- [4'-fluoro-5,6-di(2-methoxyethoxy)-3-(propan-2-yl)biphenyl- 2-yl]-2-propenenitrile, (E)-3-[4'-fluoro-5,6-methylenedioxy-3-(propan-2-yl)biphenyl- 2-yl]-2-propenenitrile, (E)-3- [5-(4'- fluorophenyl)-7 -(propan-2-yl)-1,4-benzodioxan- 6-yl]-2-propenenitrile, (E)-3-[4'-fluoro-5,6-dimethylmethylenedioxy-3-(propan-2-yl)biphenyl- 2 -yl]-2-propenenitrile, (E)-3- [4'-fluoro-6-methoxy-5-methyl-3-(propan-2-yl)biphenyl- 2-yl]-2-propenenitrile, (E)-3-[5-ethyl-4'-fluoro-6-methoxy-3-(propan-2-yl)biphenyl- 2-yl]-2-propenenitrile, (E)-3-[4',5-difluoro-6-methoxy-3-(propan-2-yl)biphenyl-2-yl) ]-2-propenenitrile, (E)-3-[5-chloro-4'-fluoro-6-methoxy-3-(propan-2-yl)biphenyl- 2-yl]-2-propenenitrile, (E)-3 - [5-bromo-4'-fluoro-6-methoxy-3-(propan-2-yl)biphenyl- 2-yl]-2-propenenitrile, and (E)-3- [4'-fluoro-5-iodo-6-methoxy-3-(propan-2-yl)biphenyl- 2-yl]-2-propenenitrile.

The 4-fluorobiphenyl derivative of formula (I) of the present invention can be produced in accordance with the following reaction scheme:

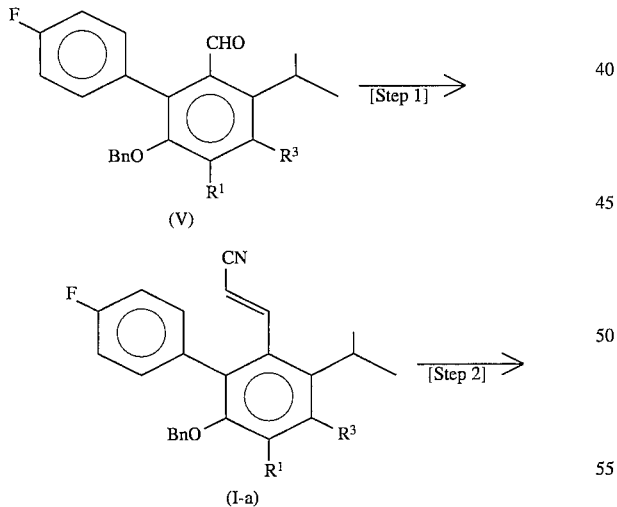

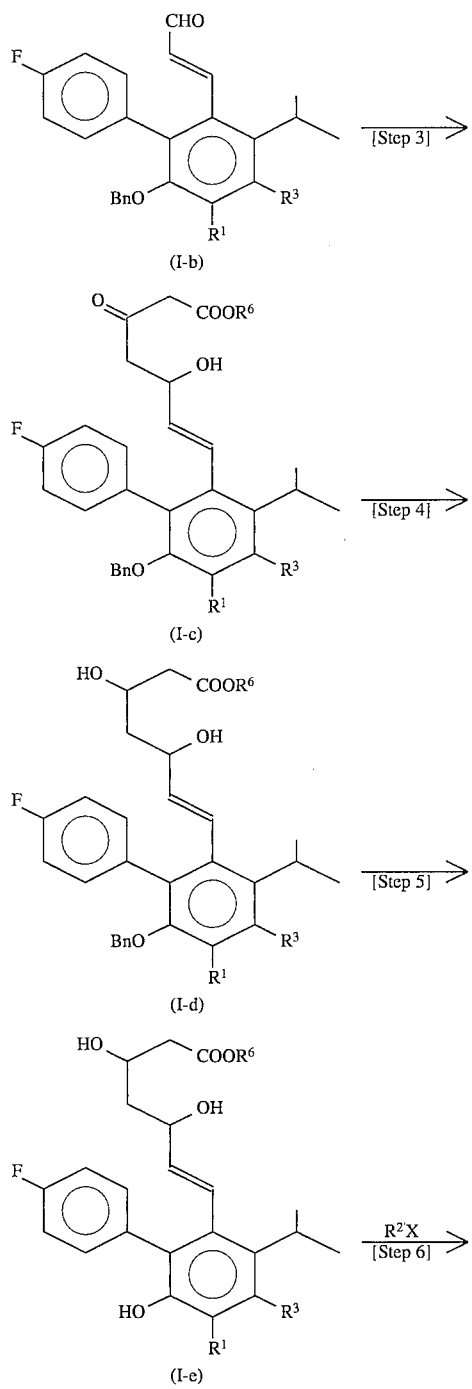

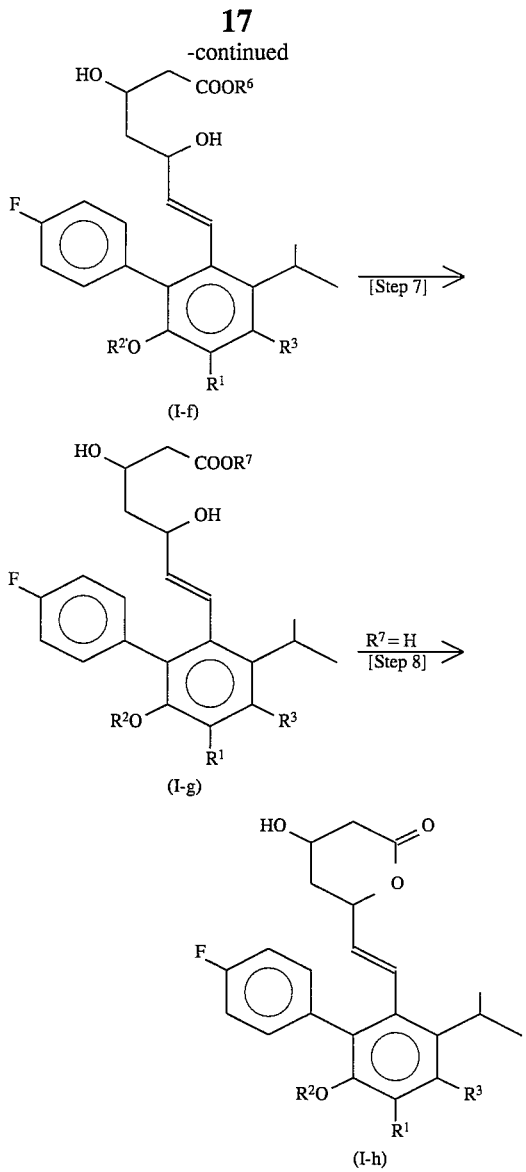

wherein $R^1$, $R^2$, and $R^3$ are respectively the same as defined previously, $R^{2'}$ is an alkyl group having 1 to 6 carbon atoms, which may have a substituent, $R^6$ is an alkyl group having 1 to 6 carbon atoms, which may have a substituent, $R^7$ is a hydrogen atom, an alkaline metal, or an alkaline earth metal, and Bn is benzyl group.

Step 1

In the reaction in this step, a 4-fluorobiphenyl derivative of formula (I-a) is produced by using a 2-biphenylcarboaldehyde derivative of formula (V) as a starting material in accordance with Horner-Emmons Reaction, Wittig Reaction and a reaction with acetonitrile.

As an agent for use in Honer-Emmons Reaction, for instance, diethyl cyanomethyl phosphonate is employed, and as an agent for Wittig Reaction, for instance, cyanomethyl triphenylphosphoniumhalide can be employed.

It is preferable that this reaction be carried out in the presence of an alkali, such as sodium hydride, potassium hydride, potassium t-butoxide, sodium carbonate, potassium carbonate, and butyl lithium.

Furthermore, it is preferable that this reaction be carried out in an inert atmosphere, in a solvent. Examples of a solvent for use in this reaction are ethers such diethyl ether, tetrahydrofuran (THF), dioxane and 1,2-dimethoxyethane (DME). These solvents can be used alone or in combination. The reaction can be carried out at temperatures in the range of 0° to 80° C.

Step 2

In this step, the 4-fluorobiphenyl derivative of formula (I-a) is reduced to produce a 4-fluorobiphenyl derivative of formula (I-b).

As a reducing agent employed in this reaction, any reducing agents which are capable of reducing cyano group to aldehyde group, for example, diisobutylaluminum hydride (DIBAL), can be employed. The reaction can be carried out in an inert solvent by methods which are conventionally known to those skilled in the art.

The 4-fluorobiphenyl derivative of formula (I-b) produced in this step can also be produced directly from the 2-biphenylcarboaldehyde derivative of formula (V) in step 1 by allowing the 2-biphenylcarboaldehyde derivative of formula (V) to react with acetaldehyde or an acetaldehyde derivative.

The acetaldehyde derivative for use in the above reaction is a Schiff's base of acetaldehyde and an amine compound, for example, N-ethylidenecyclohexylamine and N-ethylidenecyclopentylamine.

It is preferable that the above reaction be carried out in the presence of a base, such as lithium diisopropylamide (LDA), and potassium t-butoxide.

The reaction is usually carried out in an inert solvent. Examples of an inert solvent for use in this reaction include ethers such as diethyl ether, THF, dioxane, and DME. These solvents can be used alone or in combination. It is preferable that the reaction be carried out in an atmosphere of an inert gas at temperatures in the range of −78° C. to 100° C.

Step 3

In this step, a 4-fluorobiphenyl derivative of formula (I-c) is produced by allowing the 4-fluorobiphenyl derivative of formula (I-b) to react with an acetoacetate.

Examples of the acetoacetate for use in this reaction include methyl acetoacetate, ethyl acetoacetate, propyl acetoacetate, and butyl acetoacetate.

As a base for deriving a dianinon of such an acetoacetate, for example, sodium hydride and butyl lithium can be employed.

It is preferable that the reaction be carried out in an atmosphere of an inert gas, in a solvent, for instance, an inert solvent, for examples, ethers such as THF, dioxane, and DME.

The reaction can be usually carried out at a temperature in the range of −78° C. to room temperature.

Step 4

In this step, a 4-fluorobiphenyl derivative of formula (I-d) is produced by reducing the 4-fluorobiphenyl derivative of formula (I-c) obtained in Step 3.

A variety of reducing agents can be employed for the reduction of the carbonyl group in this step. For instance, sodium borohydride can be employed. The amount of such a reducing agent is in the range of 1 to 6 equivalents to one equivalent of the 4-fluorobiphenyl derivative of formula (I-c), but for more efficient synthesis of the 4-fluorobiphenyl derivative of formula (I-d), it is preferable that the amount of such a reducing agent be in the range of 1 to 4 equivalents to one equivalent of the 4-fluorobiphenyl derivative of formula (I-c).

For improving the steric selectivity in this step, it is preferable to add to the reaction system in this step a borane compound such as trimethylborane, triethylborane, or diethylmethoxyborane, and pivalic acid.

The reaction is usually carried out in an inert solvent. Examples of an inert solvent for use in this reaction include water, alcohols such as methanol, ethanol, and butanol; ethers such as THF, and dioxane; halogenated hydrocarbons such as methylene chloride, and 1,2-dichloroethane; and aromatic hydrocarbons such as benzene and toluene. These inert solvents can be used alone or in combination.

The reaction can be usually carried out at temperatures in the range of −78° C. to room temperature.

Step 5

In this step, a 4-fluorobiphenyl derivative of formula (I-e) is produced by subjecting the 4-fluorobiphenyl derivative of formula (I-d) obtained in Step 4 to catalytic reduction.

It is preferable that the catalytic reduction in this step be such that the double bond in the 4-fluorobiphenyl derivative of formula (I-d) be not reduced. Thus, it is preferable to use, for instance, $H_2$/Lindlar's catalyst, and $HCO_2H$, $NEt_3$/Pd-C catalysts.

The reaction is usually carried out in a solvent, for examples, alcohols such as methanol, ethanol and propanol; esters such as methyl acetate, and ethyl acetate; and acetic acid. These solvents can be used alone or in combination.

Step 6

In this step, a 4-fluorobiphenyl derivative of formula (I-f) is produced by allowing the 4-fluorobiphenyl derivative of formula (I-e) obtained in Step 4 to react with a compound of formula $R^{2'}$-X.

In the compound of formula $R^{2'}$-X employed in this step, X is, for instance, a halogen atom such as chlorine, bromine, and iodine; or a substituted sulfonyloxy group such as a methanesulfonyloxy group, and a p-toluenesulfonyloxy group; and the lower alkyl group or a substituted lower alkyl group represented by $R^{2'}$ is respectively the same as the lower alkyl group or the substituted lower alkyl group represented by $R^I$ previously defined in formula (I).

In this step, the compound of formula $R^{2'}$-X is used in an amount in the range of 1 to 10 equivalents to one equivalent of the 4-fluorobiphenyl derivative of formula (I-e), preferably in an amount in the range of 1 to 3 equivalents to one equivalent of the 4-fluorobiphenyl derivative of formula (I-e) for the effective synthesis of the 4-fluorobiphenyl derivative of formula (I-f).

It is preferable that the reaction in this step be carried out in the presence of a base such as potassium carbonate, sodium carbonate, sodium hydroxide, and potassium hydroxide. Further it is preferable that the reaction be carried out in an inert solvent. Examples of an inert solvent for use in this reaction include ketones such as acetone and methyl ethyl ketone; ethers such as diethyl ether, THF, dioxane, and DME; and dimethylformamide (DMF).

The reaction can be carried out at temperatures in the range of 0° C. to 100° C.

Step 7

In this step, the 4-fluorobiphenyl derivative of formula (I-g) is produced by hydrolyzing the 4-fluorobiphenyl derivative of formula (I-f) obtained in Step 6 by use of a base.

Examples of a base for the hydrolysis in this step are hydroxides of alkaline metals and alkaline earth metals such as sodium hydroxide, potassium hydroxide, calcium hydroxide, and barium hydroxide.

In this step, such a base is used in an amount in the range of 1 to 3 equivalents, preferably in the range of 1 to 2 equivalents, to one mole of the 4-fluorobiphenyl derivative of formula (I-f).

The reaction is usually carried out in water, or in a mixed solvent of water and a solvent which is miscible with water, such as methanol and ethanol, at temperatures in the range of 0° to 80° C.

Step 8

In this step, a 4-fluorobiphenyl derivative of formula (I-h) is produced by subjecting the 4-fluorobiphenyl derivative of formula (I-g) in which $R^7$ is a hydrogen atom, which is obtained in Step 7, to ring closure.

The reaction in this step is carried out in a neutral or acidic condition, in an inert solvent, for example, an aromatic hydrocarbon such as toluene, and xylene, a halogenated hydrocarbon such as dichloromethane, chloroform, and 1,2-dichloroethane; an ester such as methyl acetate; or in a mixed solvent of any of the above solvents.

The reaction can be carried out at temperatures in the range of room temperature to 150° C.

When the above reaction is carried out in an acidic condition, acids such as trifluoroacetic acid, and p-toluenesulfonic acid can be employed.

Furthermore, this step can be conducted by use of a condensing agent, for example, carbodiimide reagents such as dicyclohexylcarbodiimide (DCC).

Furthermore, the 4-fluorobiphenyl derivative of formula (I) can be produced by conducting the reaction in the same manner as in the previously mentioned reaction scheme 1 from a 2-biphenylcarbaldehyde derivative of the following formula (VI), in which the benzyl group in the 2-biphenyl-carbaldehyde derivative of formula (V) is replaced by $R^2$:

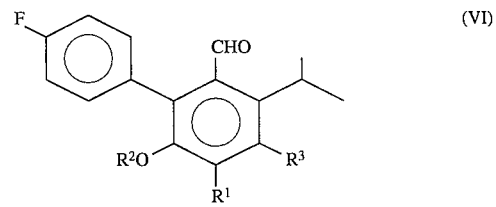

(VI)

wherein $R^1$, $R^2$, and $R^3$ and are respectively the same as defined previously.

When the reaction is conducted in accordance with the previously mentioned reaction scheme 1 by using the 2-biphenylcarbaldehyde of formula (VI), the previously mentioned Step 5 and Step 6 can be omitted.

EXAMPLE 1

(E)-3-[6-benzyloxy-4'-fluoro-5-methoxy-3-(propan-2-yl)biphenyl- 2-yl]-2-propenenitrile:

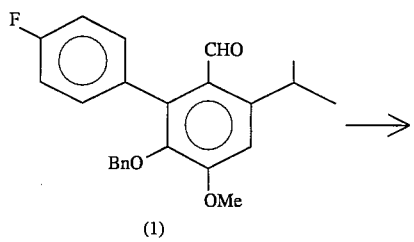
(1)

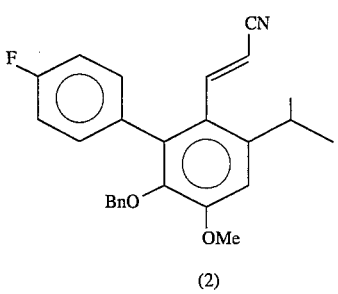
(2)

In an atmosphere of argon, 2.64 g (66.0 mmol) of a 60% sodium hydride was suspended in 100 ml of anhydrous THF. To this suspension, 10.7 ml (66.0 mmol) of diethyl cyanomethylphosphonate was added at 0° C.

To this reaction mixture, a solution of 23.7 g (62.8 mmol) of 6-benzyloxy-4'-fluoro-5-methoxy-3-(propan-2-yl)biphenyl- 2-carbaldehyde (Compound 1) in 180 ml of THF, was added dropwise with stirring over a period of 10 minutes. This reaction mixture was stirred was then stirred for 50 minutes.

The reaction mixture was then added to a saturated aqueous solution of ammonium chloride. This mixture was extracted with ethyl acetate.

The ethyl acetate extract layer was successively washed with water and then with a saturated aqueous solution of sodium chloride, dried over magnesium sulfate, and then concentrated. The residue was then crystallized from a mixed solvent of ethyl acetate and hexane, whereby (E)-3-[6-benzyloxy-4'-fluoro-5-methoxy-3-(propan- 2-yl)biphenyl-2-yl]-2-propenenitrile (Compound 2) was obtained in a yield of 15.9 g (63.0%). The filtrate obtained in the crystallization was concentrated, chromatographed on silica gel and eluted with a mixed solvent of ethyl acetate and hexane (1:4), whereby Compound 2 was also obtained in a yield of 4.50 g (17.9%).

Melting point: 175.0°–175.5° C. (colorless needles, recrystallized from a mixed solvent of ethyl acetate and hexane)

$^1$HNMR (300MHz, CDCl$_3$) δ 1.28 (d, J=6.8Hz, 6H), 3.20 (hept, J=6.8Hz, 1H),3.96 (s, 3H), 4.62 (s, 2H), 4.90 (d, J=17.0Hz, 1H), 6.92 (s, 1H), 6.90–6.98 (m, 2H), 7.03–7.15 (m, 4H), 7.18–7.25 (m, 3H2), 7.31 (d, J=17.0Hz, 1H)ppm. IR (KBr): 2972, 2216, 1620, 1582 cm$^{-1}$. Mass (m/z, %): 401 (M$^+$, 52), 310 (10), 268 (40), 253 (16), 91 (100).

EXAMPLE 2

(E)-3-[6-benzyloxy-4'-fluoro-5-methoxy-3-(propan-2-yl)biphenyl- 2-yl]-2-propenal:

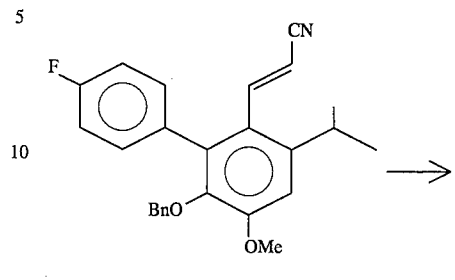
(2)

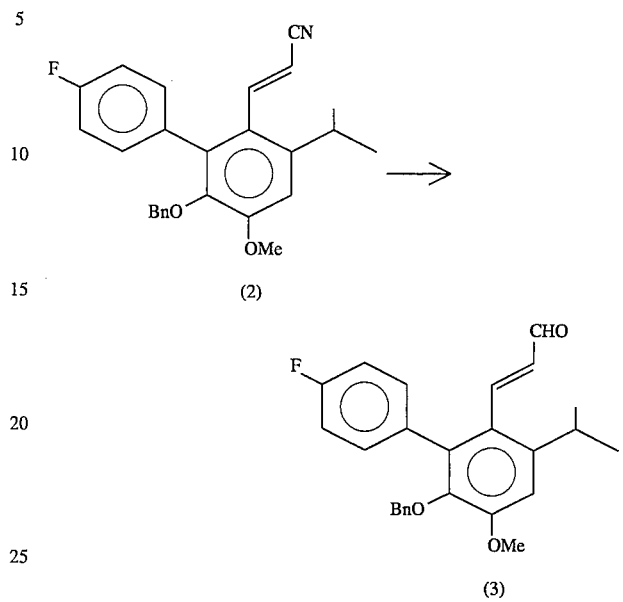
(3)

To a solution prepared by adding 34.5 ml (60.6 mmol) of diisobutylaluminum hydride to 50 ml of anhydrous toluene, a solution prepared by dissolving 22.1 g (55.1 mmol) of Compound 2 synthesized in Example 1 in 250 ml of anhydrous toluene was added dropwise over a period of 50 minutes. After the dropwise addition of the toluene solution of Compound 2, the reaction mixture was stirred for 20 minutes.

To this reaction mixture, methanol was added until bubbles were not formed any longer in the reaction mixture.

The reaction mixture was then added to a 1N hydrochloric acid at room temperature. To this mixture, ethyl acetate was added, and the mixture was stirred for 2 hours and 40 minutes.

The ethyl acetate layer was separated, washed with water and then with a saturated aqueous solution of sodium chloride, and dried over magnesium sulfate and then concentrated.

The residue was then crystallized from a mixed solvent of ethyl acetate and hexane, whereby (E)-3-[6-benzyloxy-4'-fluoro-5-methoxy-3-(propan-2-yl)biphenyl-2-yl]- 2-propenal (Compound 3) was obtained in a yield of 18.77 g (84.3%).

The filtrate obtained in the crystallization was concentrated, chromatographed on silica gel and eluted with a mixed solvent of ethyl acetate and hexane (1:3), whereby Compound 3 was also obtained in a yield of 777 mg (3.5%).

Melting point: 129.5°–130.5° C. (colorless needles, recrystallized from a mixed solvent of ethyl acetate and hexane)

$^1$HNMR (300MHz, CD$_3$OD) δ 1.31 (d, J=6.8Hz, 6H), 3.35 (hept, J=6.8Hz, 1H), 3.99 (s, 3H), 4.67 (s, 2H), 5.71 (dd, J=16.2 and 7.7Hz, 1H), 6.91–6.96 (m, 2H), 7.05–7.22 (m, 8H), 7.59 (d, J=16.2Hz, 1H), 9.34 (d, J=7.7Hz, 1H)ppm. IR (KBr): 3064, 1688, 1582 cm$^{-1}$. Mass (m/z, %): 404 (M$^+$, 27), 361 (100), 313 (16), 271 (26), 253 (17), 91 (72).

EXAMPLE 3

Ethyl (E)-7-[6-benzyloxy-4'-fluoro-5-methoxy-3-(propan-2-yl)biphenyl- 2-yl]-5-hydroxy-3-oxo-6-heptenoate:

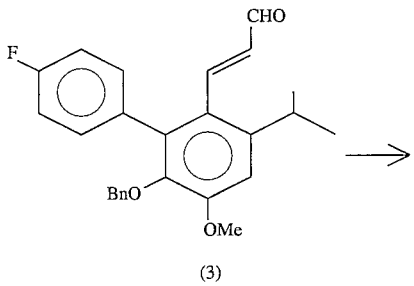

(3)

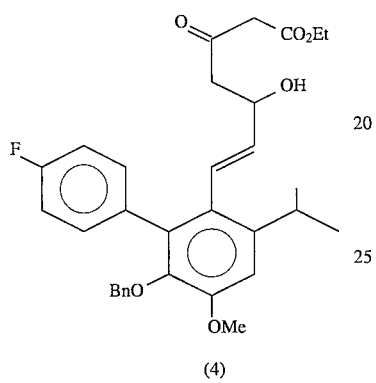

(4)

In a stream of argon, 7.94 g (62.3 mmol) of ethyl acetoacetate was added to a suspension prepared by dispersing 2.49 g (62.3 mmol) of sodium hydride (60%) in 80 ml of anhydrous THF, and the mixture was stirred for 35 minutes.

To this reaction mixture, 39.9 ml (62.3 mmol) of a 15% hexane solution of butyllithium was added, and the mixture was stirred for 30 minutes, and was then cooled to −78° C.

A THF solution of 19.4 g (47.9 mmol) of Compound 3 synthesized in Example 2, which was dissolved in 100 ml of anhydrous THF, was added dropwise to the above reaction mixture over a period of 25 minutes. After the dropwise addition of Compound 3, the reaction mixture was stirred for 2 hours.

The reaction mixture was added to 1N hydrochloric acid, and the mixture was then extracted with ethyl acetate. The extract layer was washed with water and then with a saturated aqueous solution of sodium chloride, dried over magnesium sulfate, and concentrated.

The residue was crystallized from a mixed solvent of ethyl acetate, hexane and dichloromethane, whereby ethyl (E)-7-[6-benzyloxy-4'-fluoro-5-methoxy-3-(propan-2-yl)biphenyl- 2-yl]-5-hydroxy-3-oxo-6-heptenoate (Compound 4) was obtained in a yield of 2.97 g (11.6%).

The filtrate obtained in the crystallization was concentrated, chromatographed on silica gel and eluted with a mixed solvent of ethyl acetate and hexane (1:3), whereby Compound 4 was also obtained in a yield of 20.5 g (80.1%).

Melting point: 72.0°–73.0° C. (colorless needles, recrystallized from a mixed solvent of ethyl acetate, hexane, and dichloromethane)

$^1$HNMR (300MHz, CDCl$_3$) δ 1.23 (d, J=6.8Hz, 3H), 1.24 (d, J=6.8Hz, 3H), 1.28 (t, J=7.2Hz, 3H), 2.32–2.48 (m, 2H), 3.21 (hept, J=6.8Hz, 1H), 3.40 (s, 2H), 3.93 (s,3H), 4.20 (q, J=7.2Hz, 2H), 4.44–4.52 (m, 1H), 4.64 (s, 2H), 5.15 (dd, J=16.1 and 6.2Hz, 1H), 6.39 (dd, J=16.1 and 1.3HI, 1H), 6.88 (s, 1H), 6.93–7.01 (m, 2H), 7.01–7.09 (m, 2H), 7.10–7,.17 (m, 2H), 7.17–7.26 (m, 3H)ppm. IR (KBr): 3504, 2968, 2936, 1730, 1708, 1604 cm$^{-1}$. Mass (m/z, %): 534 (M$^-$, trace), 404 (26), 361 (100), 271 (28), 253 (19), 130 (13), 91 (74).

EXAMPLE 4

Ethyl (E)-7-[6-benzyloxy-4'-fluoro-S-methoxy-3-(propan-2-yl)biphenyl- 2-yl]-3,5-dihydroxy-6-heptenoate:

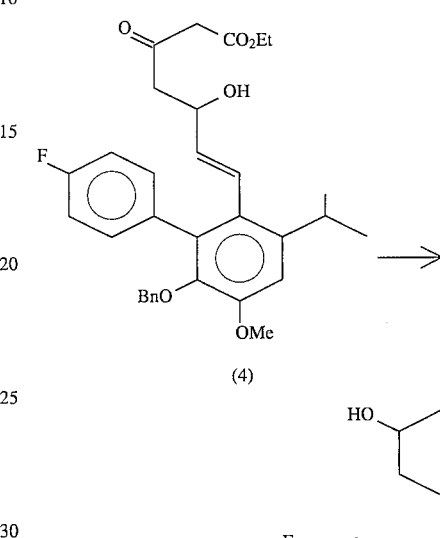

(4)

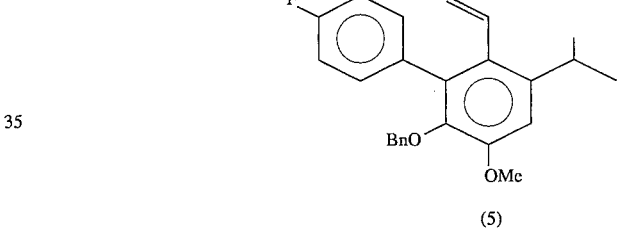

(5)

In an argon atmosphere, 56.6 ml (56.6 mmol) of a 1.0 M tetrahydropyran solution of triethylborane was added to 222 mg (2.18 mmol) of pivalic acid was added, and the mixture was stirred at room temperature for 55 minutes.

To this mixture, 23.23 g (43.5 mmol) of Compound 4 synthesized in Example 3, with being dissolved in 150 ml of anhydrous THF, was added, and the mixture was stirred for I hour.

The reaction mixture was then cooled to −78° C., and 6.6 ml of methanol was added thereto. To this reaction mixture, 2.47 g (65.3 mmol) of sodium borohydride was added, with the entire amount being into several portions. The reaction mixture was then starred for 1 hour and 20 minutes.

The reaction mixture was then gradually added to a mixed solution of 180 ml of a 30% aqueous solution of hydrogen peroxide and 180 ml of water at 0° C. The mixture was stirred overnight. The thus obtained reaction mixture was added to a saturated aqueous solution of ammonium chloride, and the mixture was then extracted with ethyl acetate.

The extract layer was successively washed with water, a saturated aqueous solution of sodium thiosulfate, water, and then a saturated aqueous solution of sodium chloride, dried over magnesium sulfate, and concentrated.

The residue was chromatographed on silica gel and eluted with a mixed solvent of ethyl acetate and hexane (1:1), whereby crude crystals were obtained. The thus obtained crude crystals were washed with hexane, whereby ethyl (E)-7-[6-benzyloxy-4'-fluoro-5-methoxy-3-(propan-2-yl)biphenyl- 2-yl]-3,5-dihydroxy-6-heptenoate (Compound 5) was obtained in a yield of 20.6 g (88.4%).

The filtrate obtained when the crude crystals were washed with hexane, was concentrated, chromatographed on silica gel and eluted with a mixed solvent of ethyl acetate and hexane (1:1), whereby Compound 5 was also obtained in a yield of 960 mg (4.1%).

Melting point: 99.5°–100.5° C. (colorless fine particle-shaped crystals, recrystallized from a mixed solvent of ethyl acetate and hexane)

$^1$HNMR (300MHz, CDCl$_3$) δ 1.23 (d, J=6.8Hz, 3H), 1.24 (d, J=6.8Hz, 3M), 1.29 (t, J=7.2Hz, 3H), 1.15–1.30 (m, 1H), 1.33–1.50 (m, 1H), 2.35–2.47 (m, 2H), 2.74–2.77 (m, 1H), 3.24 (hept, J=6.8Hz, 1H), 3.57–3.60 (m, 1H), 3.93 (s, 3H), 4.00–4.11 (m, 1H), 4.18 (q, J=7.2Hz, 2H), 4.21–4.33 (m, 1H), 4.64 (s, 2H), 5.17 (dd, J=16.0 and 6.8Hz, 1H), 6.36 (d, J=16.0Hz, 1H), 6.89 (s, 1H), 6.91–7.06 (m, 4H), 7.10–7.17 (m, 2H), 7.18–7.24 (m, 3H)ppm, IR (KBr)s 3536, 3424, 2972, 1716, 1588 cm$^{-1}$. Mass (m/z, %): 536 (M$^+$,24), 518 (36), 500 (36), 402 (36), 269 (60), 91 (100).

EXAMPLE 5

Sodium (E)-7-[6-benzyloxy-4'-fluoro-5-methoxy-3-(propan- 2-yl)biphenyl-2 -yl]-3,5 -dihydroxy-6 -heptenoate:

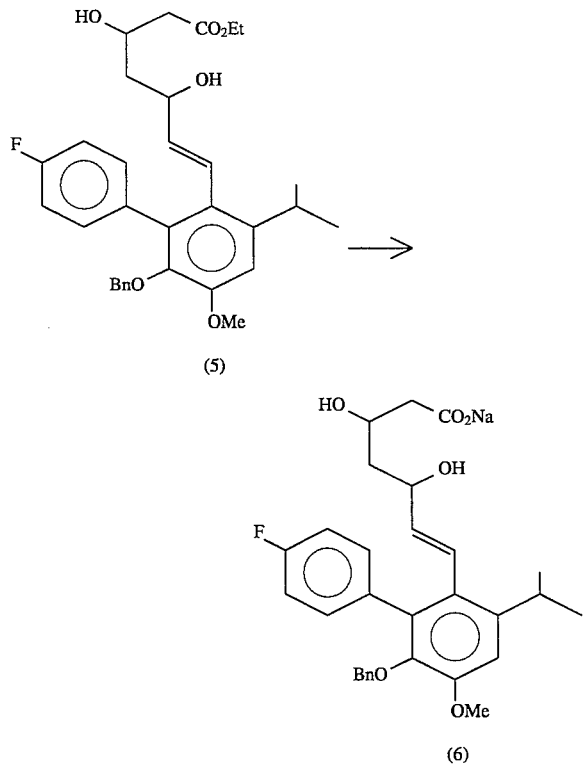

5.06 g (9.44 mmol) of Compound 5 synthesized in Example 4 was dissolved in 50 ml of ethanol. To this solution, 4.72 ml (9.44 mmol) of a 2N aqueous solution of sodium hydroxide was added, and the mixture was stirred in an atmosphere of argon at room temperature for 1 hour and 30 minutes.

The reaction mixture was then concentrated, dissolved in water and subjected to freeze-drying, whereby sodium (E)-7-[6-benzyloxy-4'-fluoro-5-methoxy-3-(propan- 2-yl)biphenyl-2-yl]-3,5-dihydroxy-6-heptenoate (Compound 6) was obtained in the form of a colorless amorphous solid in a yield of 4.82 g (96.3%).

$^1$HNMR (300MHz, CD$_3$OD) δ 1.25 (d, J=6.9Hz, 3H), 1.25 (d, J=6.9Hz,, 3H), 1.20 –1.40 (m, 1H), 1.45–1.61 (m, 1H), 2.17 (dd, J=15.4 and 7.9Hz, 1H), 2.28 (dd, J=15.4 and 4.6Hz, 1H), 3.37 (hept, J=6.9Hz, 1H), 3.72–3.82 (m, 1H), 3.93 (s, 3H), 4.14–4.23 (m, 1H), 4.59–4.69 (m, 2H), 5.23 (dd, J=16.1 and 6.7Hz, 1H), 6.32 (dd, J=16.1 and 1.0Hz, 1H), 6.91–6.97 (m, 2H), 6.99 (s, 1H), 7.03–7.20 (m, 7H)ppm. IR (KBr): 3416, 2964, 2872, 1580, 1512 cm$^{-1}$. Mass (FAB-neg, m/z, %): 529 ([M-H], trace), 507 (100).

EXAMPLE 6

Ethyl (E)-7-[4'-fluoro-6-hydroxy-5-methoxy-3-(propan-2-yl)biphenyl- 2-yl]-3,5-dihydroxy-6 -heptenoate:

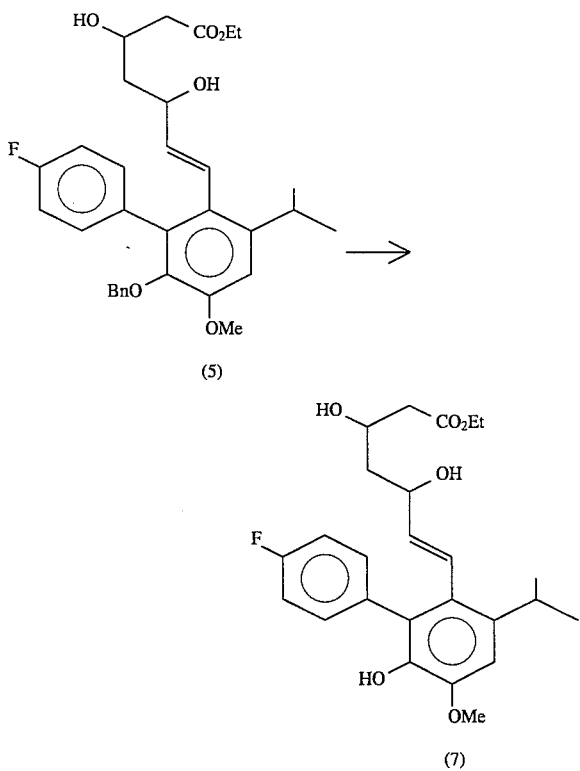

68 mg (0.127 mmol) of Compound 5 synthesized in Example 4 was dissolved in 2 ml of methanol. To this solution, 0.177 ml (1.27 mmol) of triethylamine and 7 mg of 10% Pd-C were added. To this mixture, a solution prepared by dissolving 0.043 ml (1.14 mmol) of formic acid in 0.5 ml of methanol was added. This reaction mixture was stirred in an atmosphere of argon at room temperature for 3 hours and 30 minutes. The reaction mixture was then added to diluted hydrochloric acid. The mixture was then extracted with ethyl acetate.

The extract layer was successively washed with water, a saturated aqueous solution of sodium hydrogencarbonate, water, and then a saturated aqueous solution of sodium chloride, dried over magnesium sulfate, whereby crude crystals of ethyl (E)-7-[4'-fluoro-6-hydroxy-5-methoxy-3-(propan-2-yl)biphenyl-2-yl]-3,5-dihydroxy-6-heptenoate (Compound 7) was obtained in an amount of 55 mg.

The crude crystals of Compound 7 were washed with a mixed solvent of ethyl acetate and hexane, whereby Compound 7 was obtained in a yield of 53 mg (93.5%).

Melting point: 163.0°–164.0° C. (colorless fine particle-shaped crystals, recrystallized from a mixed solvent of ethyl acetate and hexane)

¹HNMR (300MHz, CDCl₃) δ 1.21 (d, J=6.8Hz, 3H), 1.22 (d, J=6.8Hz, 3H), 1.29 (t, J=7.1Hz, 3H), 1.18–1.30 (m, 1H), 1.32–1.50 (m, 1H), 2.36–2.48 (m, 2H), 2.75–2.80 (m, 1H), 3.22 (hept, J=6.8Hz, 1H), 3.57–3.61 (m, 1H), 3.95 (s, 3H), 4.02–4.12 (m, 1H), 4.18 (q, J=7.1Hz, 2H), 4.25–4.34 (m, 1H), 5.17 (dd, J=16.1 and 6.6Hz, 1H), 5.46 (s, 1H), 6.38 (dd, J=16.1 and 1.1Hz, 1H), 6.81 (s, 1H), 7.03–7.10 (m, 2H), 7.15–7.24 (m, 2H)ppm. IR (KBr): 3352, 2980, 2940, 1718, 1608 cm⁻¹. Mass (m/z, %): 446 (M⁺, 87), 428 (96), 410 (45), 313 (67), 269 (100), 259 (78).

EXAMPLE 7

Sodium (E)-7-[4'-fluoro-6-hydroxy-5-methoxy-3-(propan-2-yl)biphenyl- 2-yl]-3,5-dihydroxy-6-heptenoate:

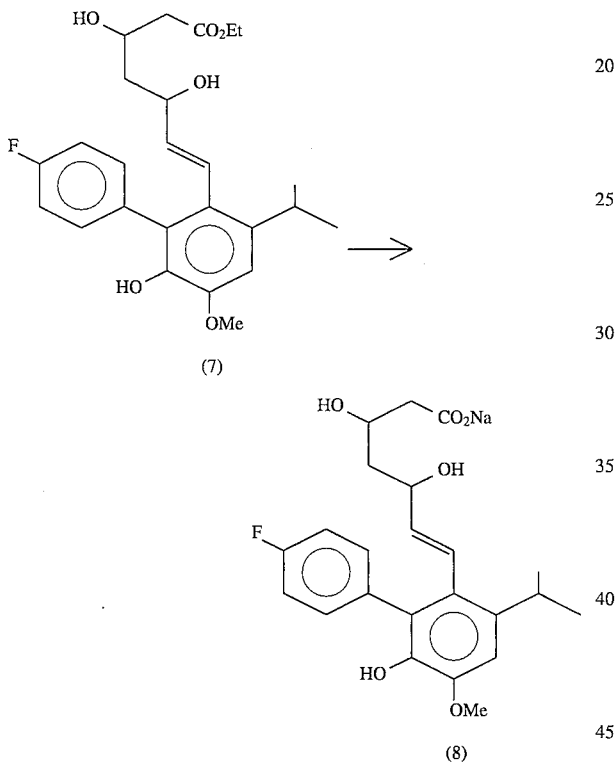

EXAMPLE 8

Ethyl (E)-7-[4'-fluoro-5,6-dimethoxy-3-(propan-2-yl)-biphenyl- 2-yl]-3,5-dihydroxy-6-heptenoate, and trans-(±)-6-[(E)-2-[4'-fluoro-5,6-dimethoxy-3-(propan-2-yl)biphenyl -2 -yl] ethenyl]-4 -hydroxytetrahydropyran-2-one:

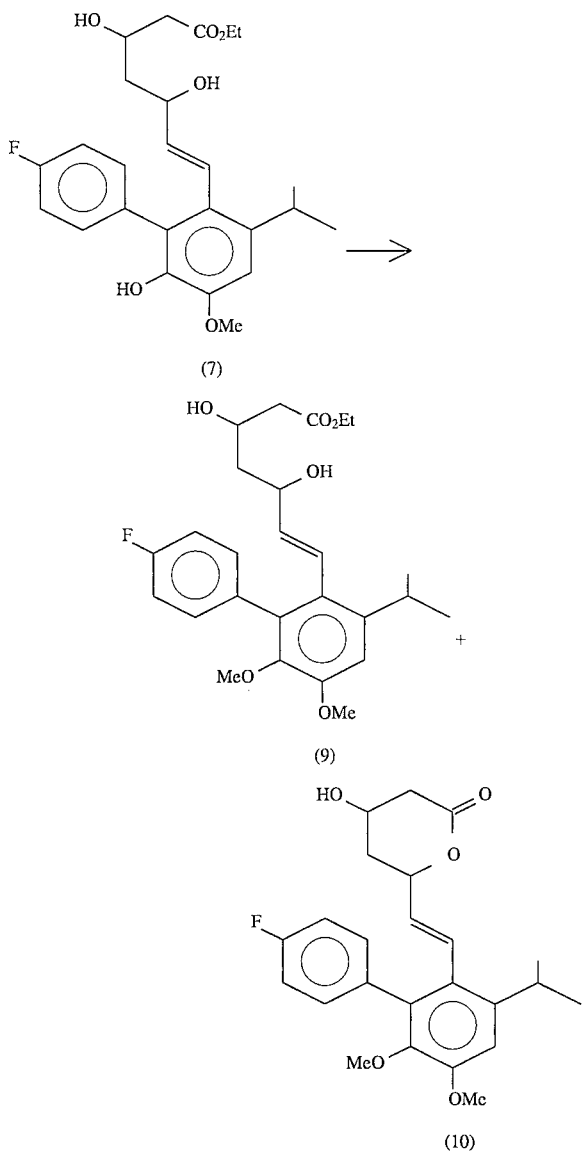

1.50 g (3.38 mmol) of Compound 7 synthesized in Example 6 was dissolved in 15 ml of ethanol. To this solution, 1.69 ml (3.38 mmol) of a 2N aqueous solution of sodium hydroxide was added, and this reaction mixture was stirred at room temperature overnight.

The reaction mixture was concentrated, and the residue was dissolved in water and was then subjected to freeze-drying, whereby sodium (E)-7-[4'-fluoro-6-hydroxy-5-methoxy-3-(propan-2-yl)biphenyl-2-yl]-3,5-dihydroxy-6-heptenoate (Compound 8) was obtained in the form of colorless amorphous solid in a yield of 1.47 g (98.8%).

¹HNMR (300MHz, CD₃OD) δ 1.22 (d, J=6.8Hz, 3H), 1.22 (d, J=6.8Hz, 3H), 1.20 –1.36 (m, 1H), 1.46–1.60 (m, 1H), 2.17 (dd, J=15.4 and 8.0Hz, 1H), 2.28 (dd, J=15.4 and 4.5Hz, 1H), 3.35 (hept, J=6.8Hz, 1H), 3.73–3.84 (m, 1H), 3.90 (s, 3H), 4.12–4.20 (m, 1H), 5.19 (dd, J=16.1 and 6.7Hz, 1H), 6.30 (dd, J=16.1 and 1.1Hz, 1H), 6.87 (s, 1H), 7.02–7.22 (m, 4H)ppm. IR (KBr): 3416, 2964, 1580, 1512 cm⁻¹. Mass (FAB-neg, m/z, %): 439 ([M-H]⁻, 4), 417 (100).

131 mg (0.294 mmol) of Compound 7 synthesized in Example 6 was dissolved in 2 ml of anhydrous DMF. To this solution, 0. 055 ml (0. 882 mmol) of methyl iodide and 122 mg (0.882 mmol) of potassium carbonate were added. This reaction mixture was stirred in an atmosphere of argon at room temperature overnight.

The reaction mixture was then added to water. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of ethyl acetate and hexane (1:1), whereby ethyl (E)-7-[4'-fluoro-5,6-dimethoxy-3-(propan-2-yl)biphenyl-2-yl]-3,5-dihydroxy-6-heptenoate (Compound 9) was obtained in a yield of 78 mg (57.7%), and trans-(±)-6-[(E)-2-[4'-fluoro-5,6-dimethoxy-3-(propan- 2-yl)biphenyl-2-yl]ethenyl]-4-hydroxytetrahydropyran-2-one (Compound 10) was also obtained in a yield of 16 mg (13.1%).

Compound 9:

Melting point: 77.0°–78.5° C. (colorless needles, recrystallized from a mixed solvent of ethyl acetate and hexane) $^1$HNMR (300MHz, CDCl$_3$) δ 1.22 (d, J=6.8Hz, 3H), 1.23 (d, J=6.8Hz, 3H), 1.15 –1.30 (m, 1H), 1.29 (t, J=7.2Hz, 3H), 1.34–1.49 (m, 1H), 2.32–2.48 (m, 2H), 2.75–2.79 (m, 1H), 3.22 (hept, J=6.8Hz, 1H), 3.48 (s, 3H), 3.58 (s with fine coupling, 1H), 3.91 (s, 3H), 4.00–4.12 (m, 1H), 4.18 (q, J=7.2Hz, 2H), 4.22–4.34 (m, 1H), 5.16 (dd, J=16.1 and 6.5Hz, 1H), 6.34 (dd, J=16.1 and 1.1Hz, 1H), 6.86 (s, 1H), 7.00–7.09 (m, 2H), 7.10–7.20 (m, 2H)ppm. IR (KBr): 3432, 1724 cm$^{-1}$. Mass (m/z, %): 460 (M$^+$, 100), 442 (88 ), 424 (41 ), 327 (51), 285 (56), 273 (65), 243 (28).

Compound 10:

Melting point: 124.0°–125.5° C. (colorless fine particle-shaped crystals, recrystallized from a mixed solvent of ethyl acetate and hexane) $^1$HNMR (300MHz, CDCl$_3$) δ 1.22 (d, J=6.8Hz, 6H), 1.40–1.76 (m, 3H), 2.54 (ddd, J=17.7, 4.3 and 1.5Hz, 1H), 2.67 (dd, J=17.7 and 5.0Hz, 1H), 3.20 (hept, J=6.8Hz, 1H), 3.48 (s, 3H), 3.92 (s, 3H), 4.10–4.18 (m, 1H), 5.01–5.10 (m, 1H), 5.17 (dd, J=16.0 and 6.5Hz, 1H), 6.43 (dd, J=16.0 and 1.2Hz, 1H), 6.87 (s, 1H), 7.00–7.10 (m, 2H), 7.10–7.20 (m, 2H)ppm. IR (KBr): 3464, 2968, 1728, 1604 cm$^{-1}$. Mass (m/z, %): 414 (M$^+$, 100), 396 (15 ), 285 (38 ), 283 (31), 257 (16).

EXAMPLE 9

Sodium (E)-7-[4'-fluoro-5,6-dimethoxy-3-(propan-2-yl)biphenyl- 2-yl]-3,5-dihydroxy-6-heptenoate:

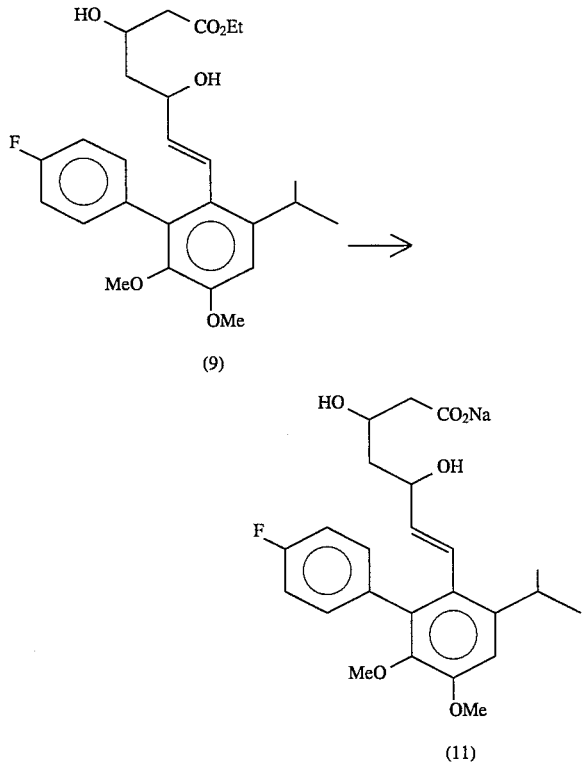

122 mg (0.265 mmol) of Compound 9 synthesized in Example 8 was dissolved in 3 ml of ethanol. To this solution, 0.530 ml (0.265 mmol) of a 0.5N aqueous solution of sodium hydroxide was added, and the mixture was stirred in an atmosphere of argon at room temperature for 1 hour and 25 minutes.

The reaction mixture was then concentrated, dissolved in water and subjected to freeze-drying, whereby sodium (E)-7-[4'-fluoro-5,6-dimethoxy-3-(propan- 2-yl)biphenyl-2-yl]-3,5-dihydroxy-6-heptenoate (Compound 11) was obtained in the form of colorless, amorphous solid in a yield of 117 mg (97.2%).

$^1$HNMR (300MHz, CD$_3$OD) δ 1.28 (d, J=6.8Hz, 6H), 1.24–1.35 (m, 1H), 1.56 (ddd, J=13.7, 8.9 and 7.3Hz, 1H), 2.21 (dd, J=15.4 and 7.8Hz, 1H), 2.32 (dd, J=15.4 and 4.5Hz, 1H), 3.38 (hept, J=6.8Hz, 1H), 3.48 (s, 3H), 3.74–3.86 (m, 1H), 3.93 (s, 3H), 4.15–4.25 (m, 1H), 5.25 (dd, J=16.1 and 6.7Hz, 1H), 6.33 (dd, J=16.1 and 1.1Hz, 1H), 6.99 (s, 1H), 7.06–7.25 (m, 4H)ppm. IR (KBr): 3456, 2968, 1574 cm$^{-1}$. Mass (FAB-neg, m/z, %): 453 ([M-H]$^-$, 7), 431 (100).

EXAMPLE 10

Ethyl (E)-7-[4'-fluoro-6-(2-hydroxyethoxy)-5-methoxy-3-(propan- 2-yl)biphenyl-2-yl]-3,5-dihydroxy-6-heptenoate:

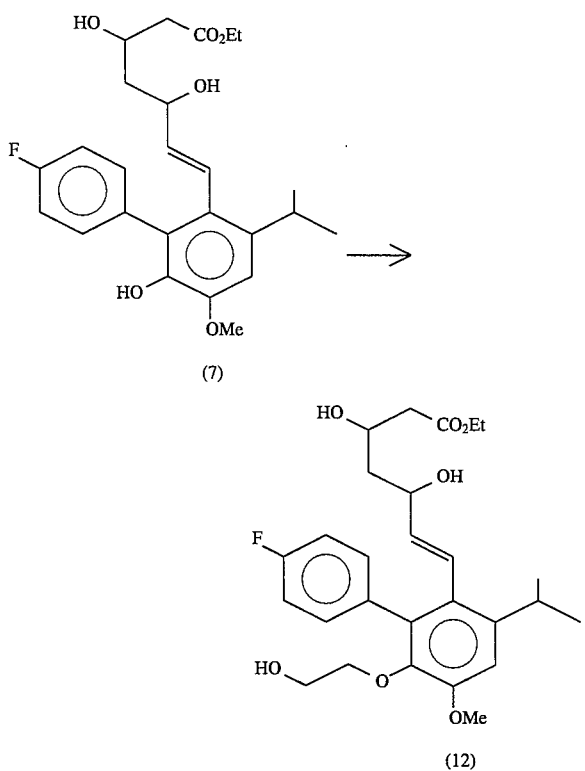

178 mg (0.40 mmol) of Compound 7 synthesized in Example 6 was dissolved in 2 ml of anhydrous DMF. To this solution, 0.156 ml (2.0 mmol) of 2-iodoethanol and 122 mg (0.882 mmol) of potassium carbonate were added. This reaction mixture was stirred in an atmosphere of argon at room temperature for two days.

The reaction mixture was then added to water. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of ethyl acetate and hexane (1:1 to 2:1), whereby ethyl (E)-7-[4'-fluoro-6-(2-hydroxyethoxy)-5-methoxy-3-(propan-2-yl)biphenyl-2-yl]- 3,5-dihydroxy-6-heptenoate (Compound 12) was obtained in the form of a colorless oil in a yield of 25 mg (12.8%). Compound 7 was recovered in a yield of 141 mg (79.2%).

¹HNMR (300MHz, CDCl₃) δ 1.22 (d, J=6.8Hz, 3H), 1..23 (d, J=6.8Hz, 3H), 1.29 (t, J=7.2Hz, 3H), 1.17–1.32 (m, 1H), 1.32–1.48 (m, 1H), 2.33–2.48 (m, 2H), 2.85 (broad s, 1H), 3.23 (hept, J=6.8Hz, 1H), 3.47–3.55 (m, 2H), 3.59 (broad s, 1H), 3.62–3.69 (m, 2H), 3.92 (s, 3H), 4.00–4..11 (m, 1H), 4.18 (q, J=7.2Hz, 2H), 4.24–4.34 (m, 1H), 4.53 (s, 1H), 5.17 (dd, J=16.1 and 6.5Hz, 1H), 6.36 (dd, J=16.1 and 1.1Hz, 1H), 6.86 (s, 1H), 7.00–7.12 (m, 2H), 7.15–7.26 (m, 2H)ppm. IR (liquid film): 3460, 2968, 1730 cm⁻¹. Mass (m/z, %): 490 (M⁺, 7), 444 (8), 426 (100), 341 (28), 271 (39).

EXAMPLE 11

Sodium (E)7-[4,-fluoro-6-(2-hydroxyethoxy)-B-methoxy-3-(propan-2-yl)biphenyl-2-yl]-3,5-dihydroxy-6-heptenoate:

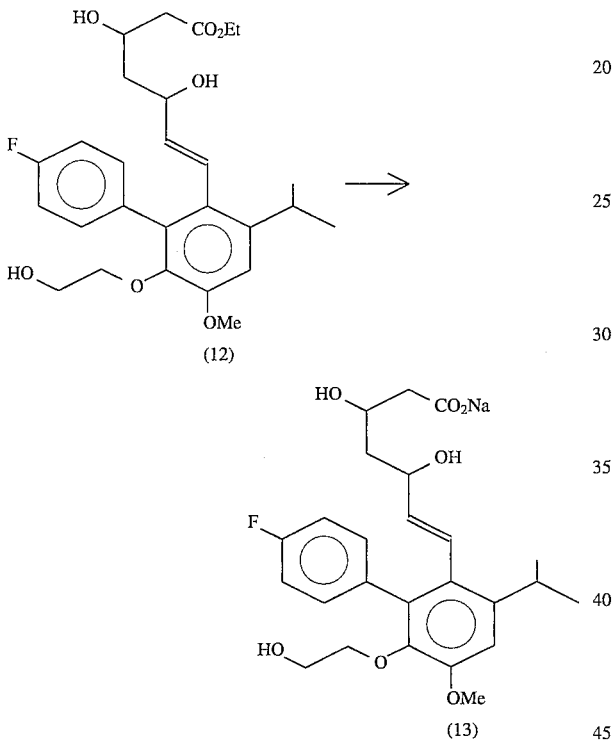

(12)

(13)

18 mg (0.037 mmol) of Compound 12 synthesized in Example 10 was dissolved in 1 ml of ethanol. To this solution, 0.37 ml (0.037 mmol) of a 0.1N aqueous solution of sodium hydroxide was added, and the mixture was stirred in an atmosphere of argon at room temperature for 40 minutes.

The reaction mixture was then concentrated, dissolved in water and subjected to freeze-drying, whereby sodium (E)-7-[4'-fluoro-6-(2-hydroxyethoxy)-5-methoxy- 3-(propan-2-yl)biphenyl-2-yl]-3,5-dihydroxy-6-heptenoate (Compound 13) was obtained in the form of a colorless, amorphous solid in a quantitative yield.

¹HNMR (300MHz, CD₃OD) δ 1.24 (dr J=6.8Hz, 6H), 1.20–1.35 (m, 1H), 1.47–1.59 (m, 1H), 2.16 (dd, J=15.3 and 7.8Hz, 1H), 2.28 (dd, J=15.3 and 4.4Hz, 1H), 3.35 (hept, J=6.8Hz, 1H), 3.39–3.44 (m, 2H), 3.64–3.70 (m, 2H), 3.70–3.80 (m, 1H), 3.90 (s, 3H), 4.12–4.21 (m, 1H), 5.22 (dd, J=16.1 and 6.6Hz, 1H), 6.31 (dd, J=16.1 and 1.1Hz, 1H), 6.96 (s, 1H), 7.05–7.23 (m, 4H)ppm. IR (KBr): 3448, 2968, 1584, 1514 cm⁻¹. Mass (FAB-neg, m/z, %): 483 ([M-H]⁻, 11), 461 (100).

EXAMPLE 12

Ethyl (E)-7-[4'-fluoro-5-methoxy-6-(2-methoxyethoxy)-3-(propan-2-yl)biphenyl-2-yl]-3,5-dihydroxy-6-heptenoate, and trans-(+)-6-[(E)-2-[4'-fluoro-5-methoxy-6-(2-methoxyethoxy)-3-(propan-2-yl)biphenyl-2-yl]ethenyl]-4-hydroxytetrahydropyran- 2-one:

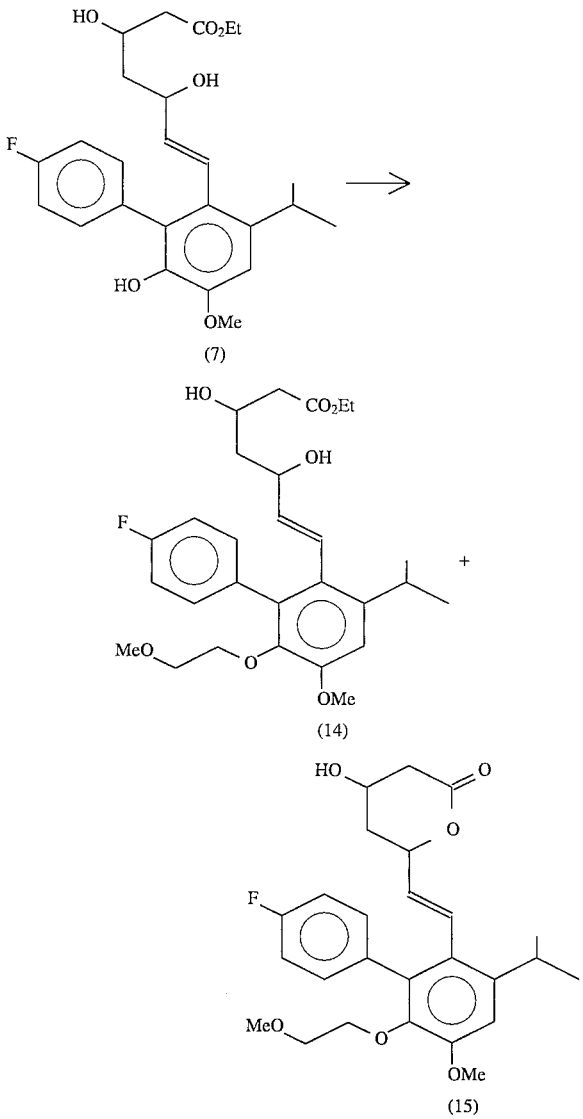

(7)

(14)

(15)

178 mg (0.40 mmol) of Compound 7 synthesized in Example 6 was dissolved in 1.5 ml of anhydrous DMF. To this solution, 372 mg (2.0 mmol) of 1-iodo-2-methoxyethane and then 166 mg (1.2 mmol) of potassium carbonate were added. This reaction mixture was stirred in an atmosphere of argon at room temperature overnight.

The reaction mixture was then added to water. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of ethyl acetate and hexane (2:1), whereby ethyl (E)-7-[4'-fluoro-5-methoxy-6-(2-methoxyethoxy)- 3-(propan-2-yl)biphenyl-2-yl]-3,5-dihydroxy-6-heptenoate (Compound 14) was obtained in a yield of 108 mg (53.6%), and trans-(±)-6-[(E)-2-[4'-fluoro- 5-methoxy-6

-(2-methoxyethoxy)-3-(propan-2-yl)biphenyl- 2-yl]ethenyl] -4-hydroxytetrahydropyran-2-one (Compound 15) was also obtained in a yield of 66 mg (36.0%).

Compound 14:

Melting point: 83.0°–84.0° C. (colorless, fine particle-shaped crystals, recrystallized from a mixed solvent of hexane and dichloromethane)

$^1$HNMR (300MHz, CDCl$_3$) δ 1.22 (d, J=6.8Hz, 3H), 1.23 (d, J=6.8Hz, 3H), 1.16 –1.33 (m, 1H), 1.34–1.48 (m, 1H), 1.28 (t, J=7.2Hz, 3H), 2.36–2.47 (m, 2H), 2.75–2.78 (m, 1H), 3.19 (s, 3H), 3.22 (hept, J=6.8Hz, 1H), 3.26–3.33 (m, 2H), 3.58 (s with fine coupling, 1H), 3.73–3.80 (m, 2H), 3.89 (s, 3H), 4.00–4.12 (m, 1H), 4.18 (q, J=7.2Hz, 2H), 4.22–4.34 (m, 1H), 5.16 (dd, J= 16.1 and 6.6Hz, 1H), 6.35 (dd, J=16.1 and 1.1Hz, 1H), 6.84 (s, 1H), 6.98–7.08 (m, 2H), 7.12–7.22 (m, 2H)ppm. IR (KBr): 3476, 2968, 1732 cm$^{-1}$. Mass (m/z, %): 504 (M$^+$, 100), 486 (55), 440 (36), 329 (42), 271 (34), 59 (61).

Compound 15:

Melting point: 111.0°–112.5° C. (colorless, fine particle-shaped crystals, recrystallized from a mixed solvent of hexane and dichloromethane)

$^1$HNMR (300 MHz, CDCl$_3$) δ 1.22 (d, J=6.8Hz, 6H), 1.40–1.75 (m, 3H), 2.54 (ddd, J=17.8, 4.4 and 1.4Hz, 1H), 2.67 (dd, J=17.8 and 5.0Hz, 1H), 3.19 (s, 3H), 3.20 (hept, J=6.8Hz, 1H), 3.30 (t, J=5.0Hz, 1H), 3.72–3.81 (m, 2H), 3.90 (s, 3H), 4.08–4.20 (m, 1H), 5.02–5.10 (m, 1H), 5.18 (dd, J=16.0 and 6.5Hz, 1H), 6.44 (dd, J=16.0 and 1.1Hz, 1H), 6.85 (s, 1H), 7.00–7.10 (m, 2H), 7.10–7.21 (m, 2H)ppm. IR (KBr): 3480, 2968, 2932, 1732, 1604 cm$^{-1}$. Mass (m/z, %): 458 (M$^+$, 100), 440 (13), 396 (14), 271 (22), 269 (23), 183 (10), 59 (39).

EXAMPLE 13

Sodium (E)-7-[4'-fluoro-5-methoxy-6-(2-methoxyethoxy)- 3-(propan- 2-yl)biphenyl-2-yl]-3,5-dihydroxy-6-heptenoate:

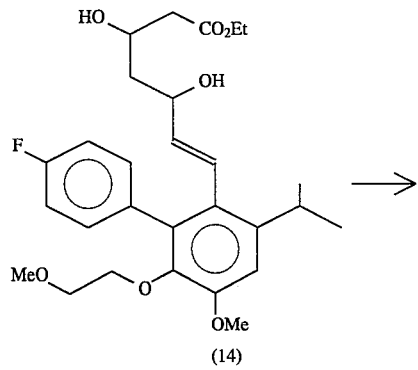

(14)

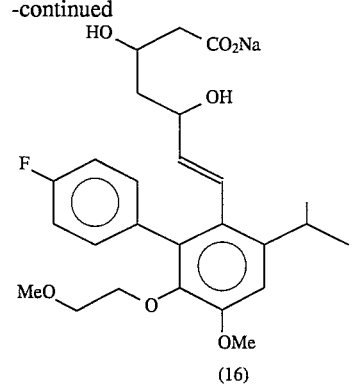

(16)

49 mg (0.097 mmol) of Compound 14 synthesized in Example 12 was dissolved in 1.5 ml of ethanol. To this solution, 0.194 ml (0.097 mmol) of a 0.5N aqueous solution of sodium hydroxide was added, and the mixture was stirred in an atmosphere of argon at room temperature for 25 minutes.

The reaction mixture was then concentrated, dissolved in water and subjected to freeze-drying, whereby sodium (E)-7-[4'-fluoro-5-methoxy-6-(2-methoxyethoxy)- 3-(propan-2-yl)biphenyl-2-yl]-3,5-dihydroxy-6-heptenoate (Compound 16) was obtained in the form of a colorless, amorphous solid in a quantitative yield.

$^1$HNMR (300MHz, CD$_3$OD) δ 1.23 (d, J=6.8Hz, 3H), 1.23 (d, J=6.8Hz, 3H), 1.20 –1.32 (m, 1H), 1.47–1.60 (m, 1H), 2.16 (dd, J=15.5 and 7.9Hz, 1H), 2.28 (dd, J=15.5 and 4.7Hz, 1H), 3.15 (s, 3H), 3.25–3.38 (m, 3H), 3.72–3.82 (m, 3H), 3.89 (s, 3H), 4.12–4.22 (m, 1H), 5.22 (dd, J=16.1 and 6.6Hz, 1H), 6.30 (dd, J=16.1 and 1.0Hz, 1H), 6.95 (s, 1H), 7.05–7.23 (m, 4H)ppm. IR (KBr): 3428, 2968, 1582, 1512 cm$^{-1}$. Mass (FAB-neg, m/z, %): 497 ([M-H]$^-$, 4), 475 (100).

EXAMPLE 14

Ethyl (E)-7-[4'-fluoro-5-methoxy-6-[2-(2-methoxyethoxy)ethoxy]- 3-(propan-2-yl)biphenyl-2-yl]-3,5-dihydroxy-6-heptenoate, and trans-(+)-[(E)-2-[4'-fluoro-5-methoxy-6-[ 2-(2-methoxyethoxy)ethoxy]-3-(propan-2-yl)biphenyl-2-yl]ethenyl]- 4-hydroxytetrahydropyran-2-one:

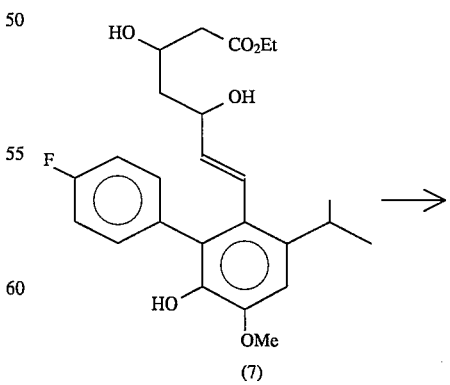

(7)

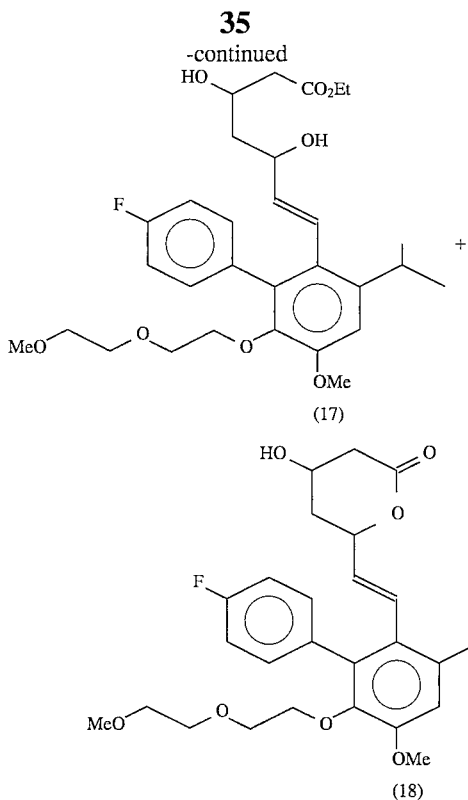

(17)

(18)

111 mg (0.25 mmol) of Compound 7 synthesized in Example 6 was dissolved in 2 ml of anhydrous DMF. To this solution, 287 mg (1.25 mmol) of 1-iodo-2-(2-methoxyethoxy)ethane and then 104 mg (0.75 mmol) of potassium carbonate were added. This reaction mixture was stirred in an atmosphere of argon at room temperature overnight.

The reaction mixture was then added to water. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of ethyl acetate and hexane (2:1), whereby ethyl (E)-7-[4'-fluoro-5-methoxy-6-[2-( 2-methoxyethoxy) ethoxy ]-3-(propan-2-yl)biphenyl-2-yl]- 3,5-dihydroxy-6-heptenoate (Compound 17) was obtained in a yield of 69 mg (50.4%), and trans-(+)-[(E)-2-[4'-fluoro-5-methoxy-6-[2-(2-methoxyethoxy)ethoxy]-3-(propan-2yl)biphenyl-2-yl]ethenyl]-4-hydroxytetrahydropyran-2-one (Compound 18) was also obtained in the form of a colorless oil in a yield of 41 mg (32.7%).

Compound 17:

Melting point: 63.0°–65.0° C. (colorless, fine particle-shaped crystals, recrystallized from a mixed solvent of ethyl acetate and hexane)

$^1$HNMR (300MHz, CDCl$_3$) δ 1.21 (d, J=6.8Hz, 3H), 1.22 (d, J=6.8Hz, 3H), 1.28 (t, J=7.1Hz, 3H), 1.16–1.32 (m, 1H), 1.34–1.48 (m, 1H), 2.33–2.48 (m, 2H), 2.74–2.78 (m, 1H), 3.15–3.29 (m, 1H), 3.34 (s, 3H), 3.41 (s, 4H), 3.34–3.44 (m, 2H), 3.57 (s with fine coupling, 1H), 3.76–3.84 (m, 2H), 3.89 (s, 3H), 4.00–4.11 (m, 1H), 4.18(q, J=7.1Hz, 2H), 4.20–4.32 (m, 1H), 5.16 (dd, J=16.1 and 6.5Hz, 1H), 6.34 (dd, J=16.1 and 1.1Hz, 1H), 6.84 (s, 1H), 6.96–7.06 (m, 2H), 7.10–7.20 (m, 2H)ppm. IR (KBr): 3444, 2968, 1726 cm$^{-1}$. Mass (m/z, %): 548 (M$^+$, 21), 530 (31), 484 (85), 271 (31), 269 (25), 183 (15), 103 (100), 59 (87).

Compound 18:

$^1$HNMR (300MHz, CDCl$^3$) δ 1.22 (d, J=6.8Hz, 6H), 1.41–1.74 (m, 3H), 2.54 (ddd, J=17.7, 4.3 and 1.3Hz, 1H), 2.67 (dd, J=17.7 and 5.0Hz, 1H), 3.13–3.28 (m, 1H), 3.34.(s, 3H), 3.40–3.45 (m, 2H), 3.41 (s, 4H), 3.78–3.84 (m, 2H), 3.89 (s, 3H), 4.09–4.19 (m, 1H), 5.00–5.10 (m, 1H), 5.17 (dd, J=16.0 and 6.5Hz, 1H), 6.43 (dd, J=16.0 and 1.0Hz, 1H), 6.85 (s, 1H), 6.98–7.10 (m, 2H), 7.10–7.22 (m, 2H)ppm. IR (liquid film): 3480, 2964, 1740 cm$^{-1}$. Mass (m/z, %): 502 (M$^+$, 59), 484 (70), 440 (17), 399 (15), 297 (25), 271 (25), 269 (27), 183 (13), 103 (100), 59 (78).

EXAMPLE 15

Sodium (E)-7-[4'-fluoro-5-methoxy-6-[2-(2-methoxyethoxy)ethoxy]-3-(propan-2-yl)biphenyl-2-yl]-3,5-dihydroxy-6-heptenoate:

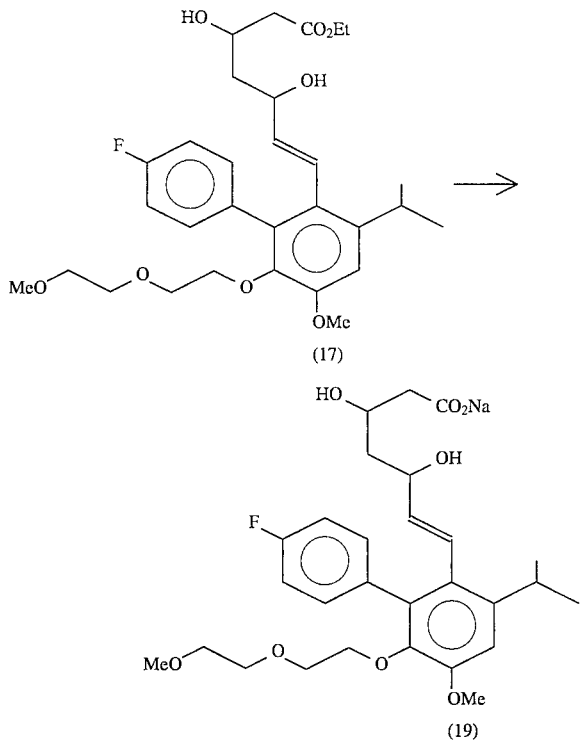

46 mg (0.084 mmol) of Compound 17 synthesized in Example 14 was dissolved in 1.5 ml of ethanol. To this solution, 0.168 ml (0.084 mmol) of a 0.5N aqueous solution of sodium hydroxide was added, and the mixture was stirred in an atmosphere of argon at room temperature for 45 minutes.

The reaction mixture was then concentrated, dissolved in water and subjected to freeze-drying, whereby sodium (E)-7-[4'-fluoro-5-methoxy-6-[2-(2-methoxyethoxy)ethoxy]-3-(propan-2-yl)biphenyl-2-yl]-3,5-dihydroxy- 6-heptenoate (Compound 19) was obtained in the form of a colorless, amorphous solid in a quantitative yield.

$^1$HNMR (300MHz, CD$_3$OD δ 1.24 (d, J=6.8Hz, 6H), 1.20–1.33 (m, 1H), 1.46–1.59 (m, 1H), 2.16 (dd, J=15.3 and 7.8Hz, 1H), 2.28 (dd, J=15.3 and 4.4Hz, 1H), 3.35–3.45 (m, 7H), 3.71–3.83 (m, 3H), 3.89 (s, 3H), 4.12–4.21 (m, 1H), 5.22 (dd, J=16.1 and 6.6Hz, 1H), 6.30 (dd, J=16.1 and 1.2Hz, 1H), 6.95 (s, 1H), 7.05–7.23 (m, 4H)ppm. IR (KBr): 3428, 2964, 1582, 1514 cm$^{-1}$. Mass (FAB-neg, m/z, %): 541 ([M-H]$^-$, 3), 519 (100).

EXAMPLE 16

Trans-(±)-6-[(E)-2-[4'-fluoro-5-methoxy-3-(propan-2-yl)-6-(2-pyridylmethyloxy)biphenyl-2-yl]ethenyl]-4-hydroxytetrahydropyran-2-one

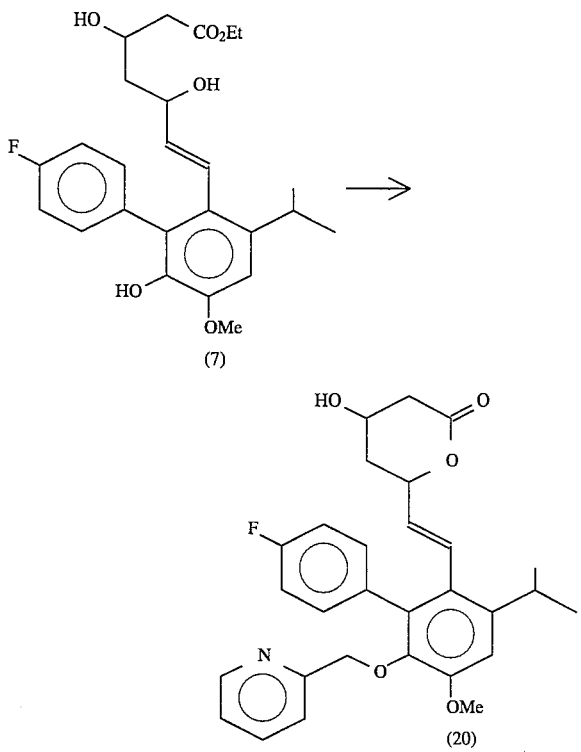

141 mg (0.316 mmol) of Compound 7 synthesized in Example 6 was dissolved in 2 ml of anhydrous DMF. To this solution, 131 mg (0.948 mmol) of potassium carbonate and then 60 mg (0.471 mmol) of 2-chloromethylpyridine were added. This reaction mixture was stirred in an atmosphere of argon at room temperature for 3 days.

The reaction mixture was then added to diluted hydrochloric acid. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of ethyl acetate and hexane (2:1) and followed by ethyl acetate, whereby trans-(±)- 6-[(E)-2-[4'-fluoro-5-methoxy-3-(propan-2-yl)-6-(2-pyridylmethyloxy)biphenyl- 2-yl]ethenyl]-4-hydroxytetrahydropyran- 2-one (Compound 20) was obtained in a yield of 51 mg (32.9%).

Melting point: 148.0°–150.0° C. (colorless, particle-shaped crystals, recrystallized from ethyl acetate and hexane)

$^1$HNMR (300M/{z, CDCl$_3$) δ 1.24 (d, J=6.8Hz, 6H), 1.40–1.69 (m, 3H), 2.53 (ddd, J=17.7, 4.3 and 1.4Hz, 1H), 2.66 (dd, J=17.7 and 4.9Hz, 1H), 3.22 (hept, J=6.8Hz, 1H), 3.91 (s, 3H), 4.08–4.18 (m, 1H), 41.84 (d, J=13.1Hz, 4.89 (d, J=13.1Hz, 1H), 5.02–5.12 (m, 1H), 5.20 (dd, J=16.0 and 6.4Hz, 1H), 6.44 (dd, J=16.0 end 1.1Hz, 1H), 6.90 (s, 1H), 6.92–7.04 (m, 3H), 7.04–7.20 (m, 3H), 7.52 (ddd, J=7.7, 7.7 and 1.7Mz, 1H), 8.42 (d with fine coupling, J=4.8Hz, 1H)ppm. IR (KBr): 3460, 2968, 1716 cm$^{-1}$. Mass (m/z, %): 491 (M$^+$, 19), 473 (62), 442 (100), 269 (33), 253 (30), 183 (17), 93 (25).

EXAMPLE 17

Sodium (E)-7-[4'-fluoro-5-methoxy-3-(propan-2-yl)-6-(2-pyridylmethyloxy)biphenyl- 2-yl]-3,5-dihydroxy-6-heptenoate:

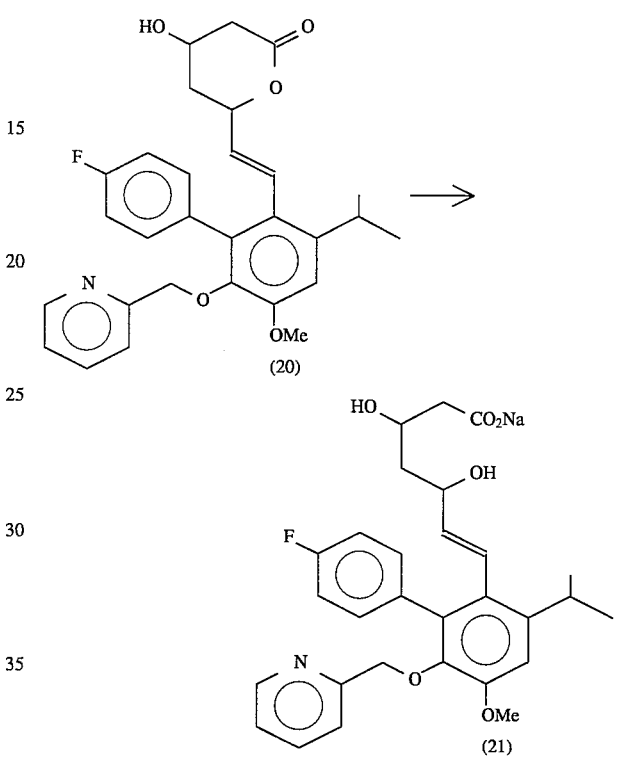

40 mg (0.082 mmol) of Compound 20 synthesized in Example 16 was dissolved in 1 ml of ethanol. To this solution, 0.1.63 ml (0.082 mmol)of a 0.5N aqueous solution of sodium hydroxide was added, and the mixture was stirred in an atmosphere of argon at room temperature for 1 hour and 55 minutes.

The reaction mixture was then concentrated, dissolved in water and subjected to freeze-drying, whereby sodium (E)-7-[4'-fluoro-5-methoxy-3-(propan-2-yl)- 6-(2-pyridylmethyloxy)biphenyl-2-yl]-3,5-dihydroxy-6-heptenoate (Compound 21) was obtained in the form of a colorless, amorphous solid in yield of 41 mg (94.7%).

$^1$HNMR (300MHz, CD$_3$OD) δ 1.26 (d, J=6.8Hz, 6H), 1.15–1.30 (m, 1H), 1.46– 1.58 (m, 1H), 2.15 (dd, J=15.4 and 7.9Hz, 1H), 2.27 (dd, J=15.4 end 4.4Hz, 1H), 3.30–3.45 (m, 1H), 3.70–3.80 (m, 1H), 3.91 (s, 3H), 4.13–4.22 (m, 1H), 4.81 (s with line coupling, 2H), 5.23 (dd, J=16.1 and 6.6Hz, 1H), 6.32 (dd, J=16.1 and 1.1Hz, 1H), 7.00–7.10 (m, 4H), 7.10–7.20 (m, 2H), 7.20–7.30 (m, 1H), 7.66 (ddd, J=7.7, 7.7. and 1.7Hz, 1H), 8.32–8.38 (m, 1H)ppm. IR (KBr)t 3432, 2968, 1588, 1514 cm$^{-1}$. Mass (FAB-neg, m/z, %): 530 ([M-H]$^-$, 2), 508 (100).

EXAMPLE 18

(E)-3- [7-benzyloxy-6-(4'-fluorophenyl)-2,3-dihydro-2,2-dimethyl- 4-(propan-2-yl)benzo[b]furan-5-yl]-2-propenenitrile:

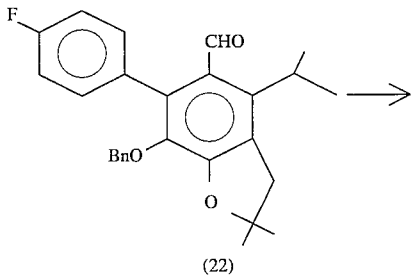

(22)

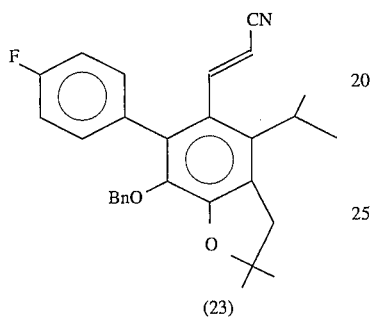

(23)

104 mg (2.61 mmol) of sodium hydride (60%) was suspended in 10 ml of anhydrous THF. To this suspension, at 0° C., 0.42 ml (2.61 mmol) of diethyl cyanomethylethylphosphonate was added, and 1.04 g (2.49 mmol) of 7-benzyloxy- 6-(4,-fluorophenyl)-2,3-dihydro-2,2-dimethyl-4-(propan- 2-yl)benzo[b]furan-5-carbaldehyde (Compound 22), which was dissolved in 5 ml of anhydrous THF, was then added and dissolved therein.

This mixture was stirred in an atmosphere of argon for 30 minutes and was then added to a 1N solution of hydrochloric acid.

This mixture was then extracted with ethyl acetate. The extract layer was successively washed with water, a saturated aqueous solution of sodium hydrogencarbonate, water, and then saturated aqueous solution of sodium chloride, dried over magnesium sulfate, and concentrated.

The residue was crystallized from hexane, whereby (E)-3-[7-benzyloxy-6-(4'-fluorophenyl)-2,3-dihydro-2,2-dimethyl- 4-(propan-2-yl)benzo[b]furan-5-yl]-2-propenenitrile (Compound 23) was obtained in a yield of 887 mg (80.8%).

The filtrate obtained in the crystallization was concentrated and chromatographed on silica gel and eluted with a mixed solvent of ethyl acetate and hexane (1:6), whereby Compound 23 was obtained in a yield of 73 mg (6.6%).

Melting point=162.0°–163.0° C. (colorless, fine particle-shaped crystals, recrystallized from hexane)

$^1$HNMR (300MHz, CDCl$_3$) δ 1.27 (d, J=7.1Hz, 6H), 1.55 (s, 6H), 3.17 (s, 2H), 3.21 (hept, J=7.1Hz, 1H), 4.80 (s, 2H), 4.86 (d, J=16.9Hz, 1H), 6.93–7.00 (m, 2H), 7.00–7.06 (m, 4H), 7.14–7.24 (m, 3H), 7.29 (d, J=16.9Hz, 1H)ppm. IR (KBr): 2972, 2936, 2216, 1616 cm$^{-1}$. Mass (m/z, %): 441 (M$^+$, 92), 350 (36), 308 (100), 291 (19), 91 (60).

EXAMPLE 19

(E)-3- [7-benzyloxy-6-(4'-fluorophenyl)-2,3-dihydro-2,2-dimethyl- 4-(propan-2-yl) benzo[b]furan-5-yl]-2-propenal:

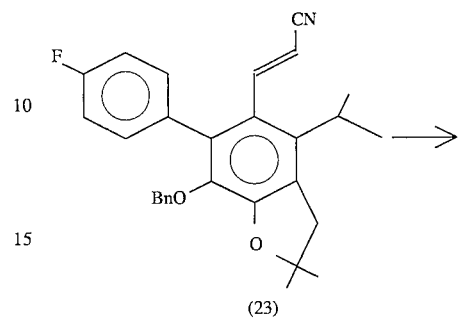

(23)

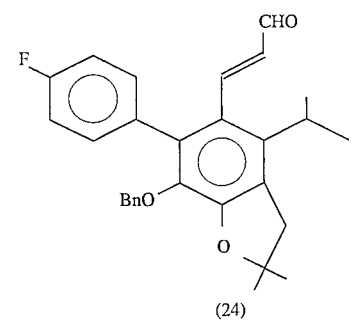

(24)

953 mg (2.16 mmol) of Compound 23 synthesized in Example 18 was dissolved in 25 ml of anhydrous toluene. To this solution, 1.35 ml (2.38 mmol) of a 25% hexane solution of diisobutylaluminum hydride was added at −78° C.

This mixture was then stirred in an atmosphere of argon for 1 hour and 30 minutes, and was then added to a 1N solution of hydrochloric acid. This mixture was stirred, with the addition of ethyl acetate thereto, at room temperature overnight.

The ethyl acetate layer of the mixture was separated and successively washed with a 1N solution of hydrochloric acid, a saturated aqueous solution of sodium hydrogencarbonate, and a saturated aqueous solution of sodium chloride, dried over magnesium sulfate, and concentrated.

The residue was chromatographed on silica gel and eluted with a mixed solvent of dichloromethane and hexane (2:1), whereby (E)-3-[7-benzyloxy-6-(4'-fluorophenyl)- 2,3-dihydro-2,2-dimethyl-4-(propan-2-yl)benzo[b]furan-5yl]-2-propenal (Compound 24) was obtained in a yield of 753 mg (78.5%).

Melting point: 142.0°–143.5° C. (colorless, fine particle-shaped crystals, recrystallized from a mixed solvent of ethyl acetate and hexane)

$^1$HNMR (300MHz, CDCl$_3$) δ 1.28 (d, J=7.1Hz, 6H), 1.57 (s, 6H), 3.21 (s, 2H), 3.33 (hept, J=7.1Hz, 1H), 4.82 (s, 2H), 5.85 (dd, J=16.2 and 7.8Hz, 1H), 6.93–7.08 (m, 6H), 7.17–7.24 (m, 3H), 7.29 (d, J=16.2Hz, 1H), 9.34 (d, J=7.8Hz, 1H)ppm. IR (KBr): 2976, 2936, 1674, 1622 cm$^{-1}$. Mass (m/z, %): 444 (M$^+$, 30), 401 (100), 353 (18), 311 (34), 293 (21), 267 (15), 91 (41).

EXAMPLE 20

Ethyl (E)-7-[7-benzyloxy-6-(4'-fluorophenyl)-2,3-dihydro-2,2-dimethyl-4-(propan-2-yl)benzo[b] furan-5-yl]-5-hydroxy- 3 -oxo-6-heptenoate:

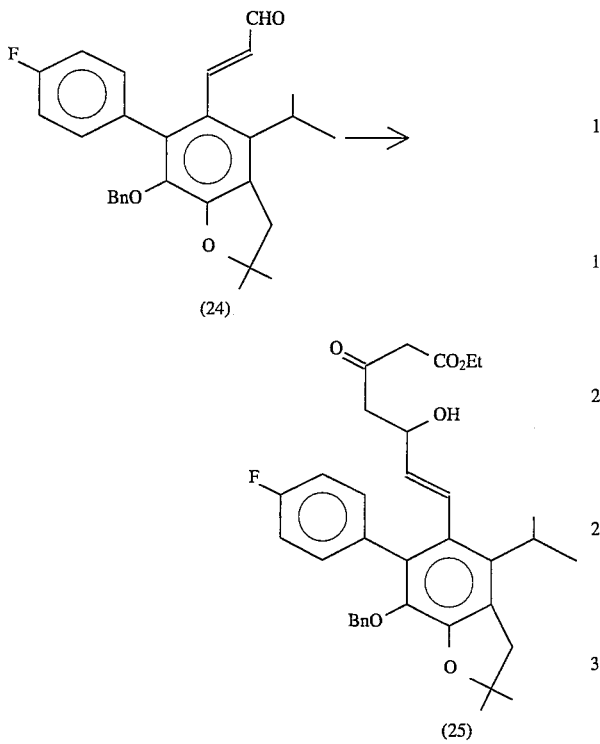

115 mg (1.88 mmol) of sodium hydride (60%) was suspended in 3 ml of anhydrous THF. To this solution, 0.367 ml (2.88 mmol) of ethyl acetoacetate was added in a stream of argon at 0° C. This reaction mixture was stirred for 40 minutes. With the addition of 1.84 ml (2.88 mmol) of a 15% hexane solution of butyllithium thereto, the reaction mixture was further stirred for 40 minutes, and was then cooled to −78° C.

To this reaction mixture, 852 mg (1.92 mmol) of Compound 24 synthesized in Example 19, which was dissolved in 5 ml of anhydrous THF, was added.

This mixture was then stirred for 50 minutes and was added to a 1N solution of hydrochloric acid.

This mixture was then extracted with ethyl acetate. The extract layer was successively washed with a saturated aqueous solution of sodium hydrogencarbonate, and then with a saturated aqueous solution of sodium chloride, dried over magnesium sulfate, and concentrated.

The residue was chromatographed on silica gel and eluted with a mixed solvent of ethyl acetate and hexane (1:3), whereby ethyl (E)-7-[7-benzyloxy-6-(4'-fluorophenyl)- 2,3-dihydro-2,2-dimethyl-4-(propan-2-yl)benzo[b]furan-5-yl]- 5-hydroxy-3-oxo-6-heptenoate (Compound 25) was obtained in a yield of 978 mg (88.7%).

Melting point: 99.5–101.0° C. (colorless, particle-shaped crystals, recrystallized from hexane)

$^1$HNMR (300MHz, CDCl$_3$) δ 1.22 (d, J=7.1Hz, 3H), 1.23 (d, J=7.1Hz, 3H), 1.28 (t, J=7.2Hz, 3H), 1.54 (s, 6H), 2.25–2.42 (m, 2H), 3.16 (s, 2H), 3.24 (hept, J=7.1Hz, 1H), 3.38 (s, 2H), 4.20 (q, J=7.2Hz, 2H), 4.40–4.50 (m, 1H), 4.81 (s, 2H), 5.08 (dd, J=16.0 and 6.4Hz, 1H), 6.36 (dd, J=16.0 and 1.2Hz, 1H), 6.94–7.07 (m, 6H), 7.17–7.23 (m, 3H)ppm. IR (KBr): 3492, 2976, 2936, 1734, 1716, 1602 cm$^{-1}$. Mass (m/z, %): 574 (M$^+$, 9), 556 (6), 401 (100), 311 (25), 293 (16), 267 (10), 91 (28).

EXAMPLE 21

Ethyl (E)-7-[7-benzyloxy-6-(4'-fluorophenyl)-2,3-dihydro-2,2-dimethyl-4-(propan-2-yl) benzo[b]furan-5-yl]-3,5-dihydroxy- 6-heptenoate:

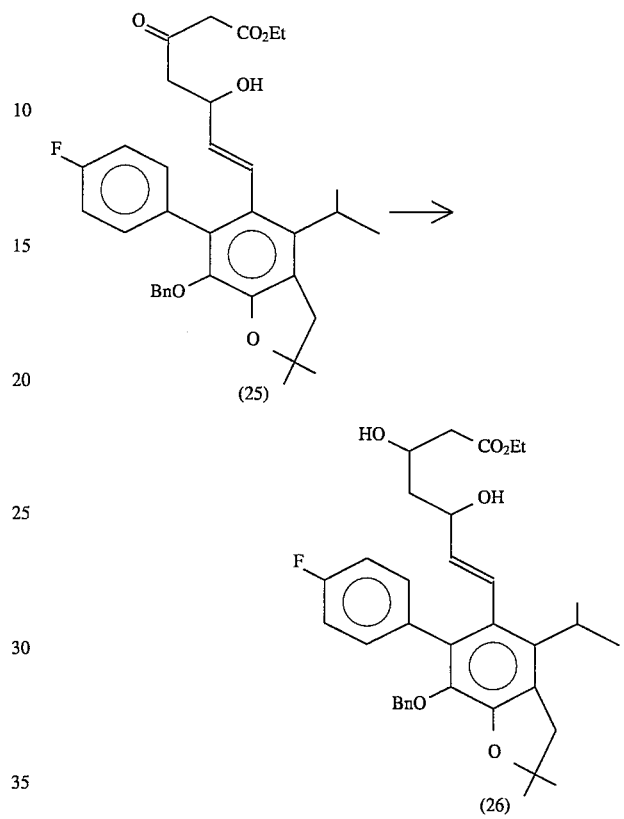

1.99 ml (1.99 mmol) of a 1.0M THF solution of triethylborane was added to 17 mg (0.167 mmol) of pivalic acid. This mixture was stirred in an atmosphere of argon at room temperature for 1 hour.

To this mixture, 924 mg (1.61 mmol) of Compound 25 synthesized in Example 20, which was dissolved in 10 ml of anhydrous THF, was added, and the mixture was stirred for 55 minutes. This reaction mixture was then cooled to −78° C., and 2.5 ml of methanol, and then 94 mg (2.49 mmol) of sodium borohydride were added thereto.

This mixture was stirred for 1 hour and 45 minutes, and poured into a solution of 7.0 ml of a 30% hydrogen peroxide, and 14 ml of water at 0° C.

This mixture was then extracted with ethyl acetate. The extract layer was successively washed with water, a saturated aqueous solution of sodium thiosulfate, and then with a saturated aqueous solution of sodium chloride, dried over magnesium sulfate, and concentrated.

The residue was chromatographed on silica gel and eluted with a mixed solvent of ethyl acetate and hexane (1:1), whereby ethyl (E)-7-[7-benzyloxy-6-(4'-fluorophenyl)- 2,3-dihydro-2,2-dimethyl-4-(propan-2-yl)benzo[b]furan-5-yl]-3,5-dihydroxy-6-heptenoate (Compound 26) was obtained in a yield of 859 mg (89.8%).

Melting point: 120.5–121.5° C. (colorless, particle-shaped crystals, recrystallized from a mixed solvent of ethyl acetate and hexane)

¹HNMR (300MHz, CDCl₃) δ 1.22 (d, J=7.1Hz, 3H), 1.23 (d, J=7.1Hz, 3H), 1.10 –1.43 (m, 2H), 1.28 (t, J=7.2Hz, 1H), 1.54 (s, 6H), 2.30–2.46 (m, 2H), 2.65 (s with fine coupling, 1H), 3.16 (s, 2H), 3.28 (hept, J=7.1Hz, 1H), 3.57 (s with fine coupling, 1H), 3.98–4.10 (m, 1H), 4.18 (q, J=7.2Hz, 2H), 4.18–4.30 (m, 1H), 4.81 (s, 2H), 5.10 (dd, J=16.0 and 6.6Hz, 1H), 6.33 (dd, J=16.0 and 1.0Hz; 1H), 6.90–7.08 (m, 6H), 7.16–7.24 (m, 3H)ppm. IR (KBr): 3456, 2976, 2936, 1730, 1604 cm⁻¹. Mass (m/z, %): 576 (M⁺, 100), 558 (61), 485 (23), 467 (27), 442 (33), 311 (67), 269 (25), 91 (42).

EXAMPLE 22

Sodium (E)-7-[7-benzyloxy-6-(4'-fluorophenyl)-2,3-dihydro- 2,2-dimethyl-4-(propan-2-yl) benzo[b]furan-5-yl]-3,5-dihydroxy-6-heptenoate:

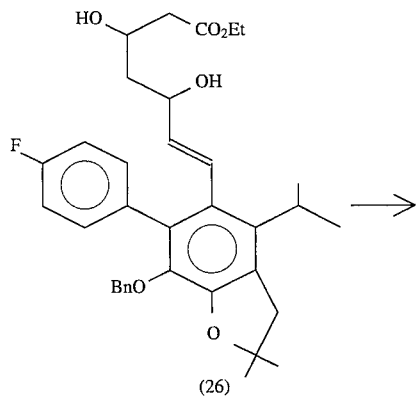

(26)

→

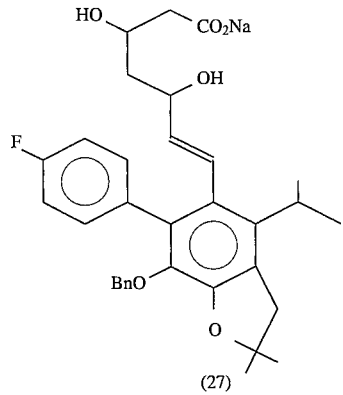

(27)

53 mg (0.092 mmol) of Compound 26 synthesized in Example 21 was dissolved in 1 ml of ethanol. To this solution, 0.092 ml (0.092 mmol) of a 1N aqueous solution of sodium hydroxide was added, and the mixture was stirred in an atmosphere of argon at room temperature for 1 hour and 50 minutes.

The reaction mixture was then concentrated, dissolved in water and subjected t6 freeze-drying, whereby sodium (E)-7-[7-benzyloxy-6-(4'-fluorophenyl)- 2,3-dihydro-2,2-dimethyl-4-(propan-2-yl)benzo[b]furan-5-yl]- 3,5-dihydroxy-6-heptenoate (Compound 27) was obtained in the form of a colorless, amorphous solid in a quantitative yield.

¹HNMR (300MHz, CD₃OD) δ 1.17–1.38 (m, 1H), 1.25 (d, J=7.2Hz, 6H), 1.42–1.53 (m, 1H), 1.53 (s, 6H), 2.15 (dd, J=15.4 and 7.8Hz, 1H), 2.27 (dd, J=15.4 and 4.4Hz, 1H), 3.21 (s, 2H), 3.43 (hept, J=7.2Hz, 1H), 3.68–3.80 (m, 1H), 4.10–4.19 (m, 1H), 4.77 (s, 2H), 5.16 (dd, J=16.0 and 6.6Hz, 1H), 6.29 (d with fine coupling, J=16.0Hz, 1H), 6.94–7.10 (m, 6H), 7.14–7.24 (m, 3H)ppm. IR (KBr): 3448, 2976, 1580, 1514 cm⁻¹. Mass (FAB-neg, m/z, %): 569 ([M-H]⁻, 8), 547 (100).

EXAMPLE 23

Ethyl (E)-7-[6-(4'-fluorophenyl)-2,3-dihydro-7-hydroxy-2,2-dimethyl-4-(propan-2-yl) benzo[b]furan-5-yl]-3,5-dihydroxy- 6-heptenoate:

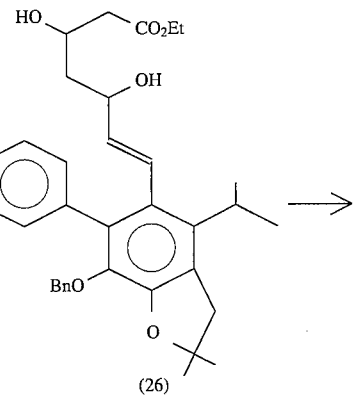

(26)

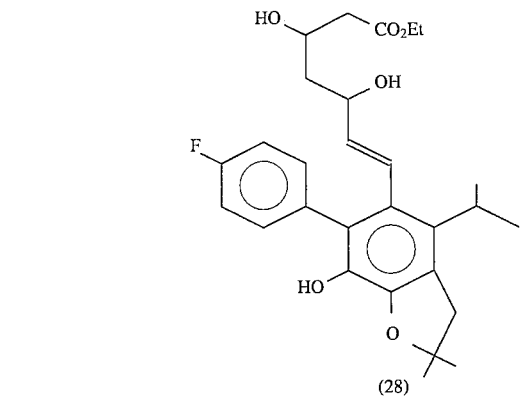

(28)

616 mg (1.07 mmol) of Compound 26 synthesized in Example 21 was dissolved in 4 ml of methanol. To this solution, 1.49 ml (10.7 mmol) of triethylamine and 62 mg of 10% Pd-C were added. To this mixture, 0.363 ml (9.63 mmol) of formic acid, which was dissolved in 2 ml of methanol, was gradually added in a stream of argon at room temperature, and this reaction mixture was stirred for 4 hours and 20 minutes.

This reaction mixture was diluted with ethyl acetate and filtered through Celite. The filtrate was successively washed with diluted hydrochloric acid, a saturated aqueous solution of sodium hydrogencarbonate, and a saturated aqueous solution of sodium chloride, dried over magnesium sulfate, and concentrated.

The residue was washed with hexane, whereby ethyl (E)-7-[6-(4'-fluorophenyl)-2,3-dihydro-7-hydroxy-2,2 -dimethyl-4-(propan-2-yl)benzo[b]furan-5-yl]-3,5 -dihydroxy-6-heptenoate (Compound 28) was obtained in the form of crystals in a yield of 475 mg (91.3%).

Melting point: 174.0°–174.5° C. (colorless, fine particle-shaped crystals, recrystallized from a mixed solvent of ethyl acetate and hexane)

¹HNMR (300 MHz, CDCl₃)

δ 1.21 (d, J=7.1Hz, 3H), 1.22 (d, J=7.1Hz, 3H), 1.29 (t, J=7.2Hz, 3H), 1.10–1.45 (m, 2H), 1.53 (s, 6H), 2.32–2.47 (m, 2H), 2.70–2.73 (m, 1H), 3.19 (s, 2H), 3.26 (hept, J=7.1Hz, 1H), 3.56–3.60 (m, 1H), 4.00–4.11

(m, 1H), 4.18 (q, J=7.2Hz, 2H), 4.20–4.31 (m, 1H), 4.54 (s, 1H), 5.11 (dd, J=16.0 and 6.5Hz, 1H), 6.36 (dd, J=16.0 and 1.1Hz, 1H), 7.03–7.13 (m, 2H), 7.14–7.23 (m, 2H)ppm.

IR (KBr): 3432, 2976, 1716, 1612 cm$^{-1}$.

Mass (m/z %): 486 (M$^+$, 100), 468 (42), 309 (49), 279 (65), 167 (72), 129 (58), 60 (82).

EXAMPLE 24

Sodium (E)-7-[ 6-(4 '-fluorophenyl)-2,3-dihydro-7-hydroxy -2,2-dimethyl-4-(propan-2-yl)benzo [ b]furan-5-yl ]-3,5 -dihydroxy-6-heptenoate:

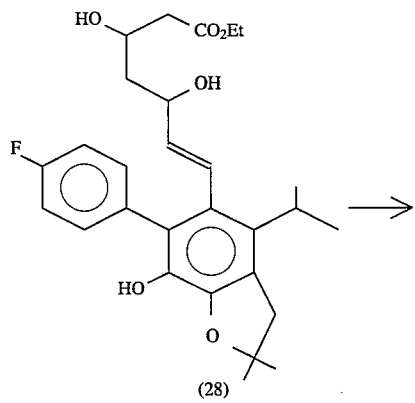

(28)

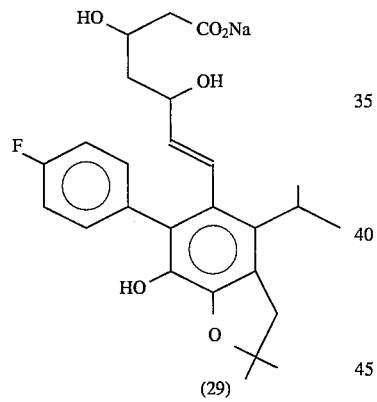

(29)

33 mg (0.068 mmol) of Compound 28 synthesized in Example 23 was dissolved in 2 ml of ethanol. To this solution, 0.068 ml (0.068 mmol) of a 1N aqueous solution of sodium hydroxide was added, and the mixture was stirred in an atmosphere of argon at room temperature for 1 hour and 40 minutes.

The reaction mixture was then concentrated, dissolved in water and subjected to freeze-drying, whereby sodium (E)-7-[6-(4'-fluorophenyl)-2,3-dihydro-7 -hydroxy-2,2-dimethyl-4-(propan-2.-yl)benzo[b]furan-5-yl]-3,5-dihydroxy-6-heptenoate (Compound 29) was obtained in the form of a colorless, amorphous solid in a quantitative yield.

$^1$HNMR (300MHz, CD$_3$OD)

δ 1.20–1.31 (m, 1H), 1.22 (d, J=7.1Hz, 6H), 1.50 (s, 6H), 1.55–1.66 (m, 1H), 2.15 (dd, J=15.3 and 7.9Hz, 1H), 2.28 (dd, J=15.3 and 4.4Hz, 1H), 3.19 (s, 2H), 3.39 (hept, J=7.1Hz, 1H), 3.72–3.83 (m, 1H), 4.10–4.20 (m, 1H), 5.13 (dd, J=16.1 and 6.6Hz, 1H), 6.28 (dd, J=16.1 and 1.0Hz, 1H), 7.00–7.18 (m, 4H)ppm.

IR (KBr): 3436, 2972, 1580, 1514 cm$^{-1}$.

Mass (FAB-neg, m/z, %): 479([M-H]$^-$, 7), 457 (100).

EXAMPLE 25

Ethyl (E)-7-[ 6-(4 '-fluorophenyl)-.2,3-dihydro-7-[ 2-(2 -methoxyethoxy)ethoxy] -2,2-dimethyl-4-(propan-2 -yl)benzo [ b ] furan-5-yl ] -3,5-dihydroxy-6-heptenoate:

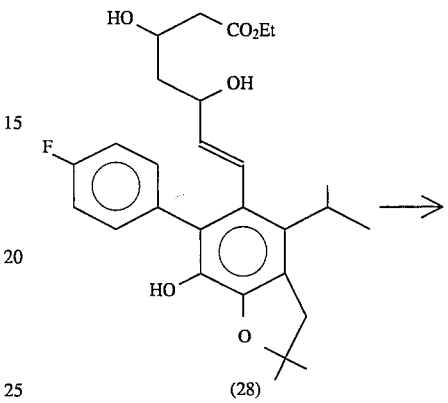

(28)

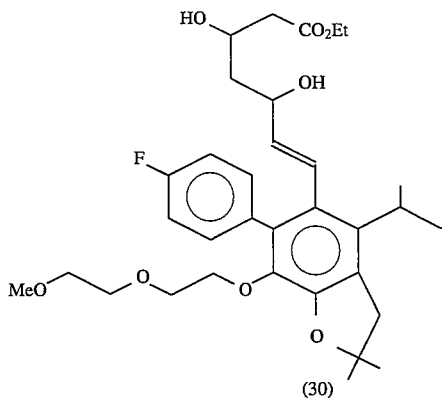

(30)

77 mg (0.158 mmol) of Compound 28 synthesized in Example 23 was dissolved in 2 ml of anhydrous DMF. To this solution, 255 mg (1.11 mmol) of 1-iodo-2-(2-methoxyethoxy)ethane and then 109 mg (0.79 mmol) of potassium carbonate were added. This reaction mixture was stirred in an atmosphere of argon at room temperature for 5 hours.

The reaction mixture was then added to water. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of ethyl acetate and hexane (2:1), whereby ethyl (E)-7-[6-(4'-fluorophenyl)-2,3-dihydro -7-[ 2-(2-methoxyethoxy) ethoxy ] -2,2-dimethyl -4 -(propan-2-yl)benzo[b]furan-5-yl ] -3,5-dihydroxy-6-heptenoate (Compound 30) was obtained in a yield of 70 mg (75.3%).

Melting point: 97.5°~98.5° C. (colorless, fine particle-shaped crystals, recrystallized from a mixed solvent of ethyl acetate and hexane)

$^1$HNMR (300MHz, CDCl$_3$ )

δ 1.21 (d, J=7 . 1Hz, 3H), 1.22 (d, J=7.1Hz, 3H), 1.28 (t, J=7.2Hz, 3H), 1.10–1.44 (m, 2H), 1.50 (s, 6H), 2.32–2.46 (m, 2H), 2.64–2.68 (m, 1H), 3.13 (s, 2H ), 3.27 (hept, J=7.1Hz, 1H ), 3.34 (s, 3H), 3.38 (s, 4H), 3.45–3.50 (m, 2H), 3.55–3.60 (m, 1H), 3.94–3.99 (m, 2H), 3.99–4.10 (m, 1H), 4.18 (q, J=7.2Hz, 2H), 4.20–4.31 (m, 1H), 5.09 (dd, J=16.0 and 6.6Hz, 1H), 6.33 (dd, J=16.0 and 1.0Hz, 1H), 6.94–7.04 (m, 2H), 7.08–7.16 (m, 2H)ppm.

IR (KBr): 3432, 2972, 2936, 2880, 1722, 1596 cm$^{-1}$.

Mass (m/z, %): 588 (M$^+$, 100), 570 (76), 454 (23 ), 413 (17), 311 (17), 269 (11), 103 (36), 59 (40).

EXAMPLE 26

Sodium (E)-7-[ 6-(4 '-fluorophenyl)-2,3-dihydro-7-[2-(2-methoxyethoxy) ethoxy ] -2,2-dimethyl-4-(propan-2-yl) benzo[b] furan-5-yl ] -3,5-dihydroxy-6-heptenoate:

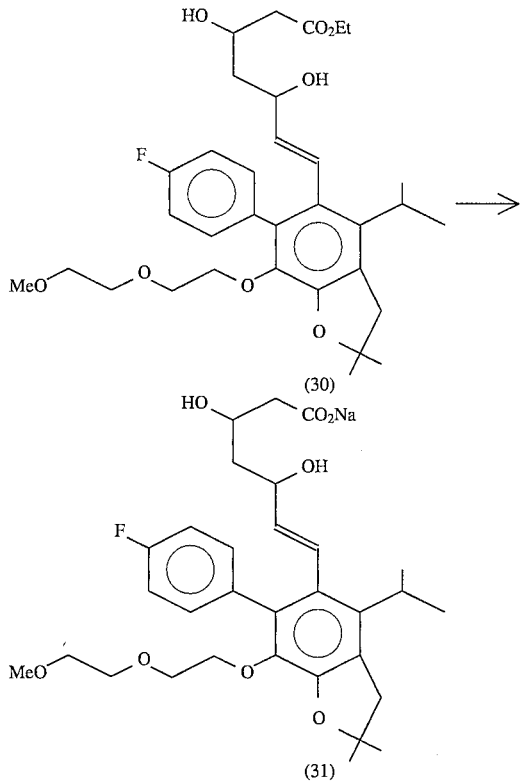

55 mg (0.094 mmol) of Compound 30 synthesized in Example 25 was dissolved in 1 ml of ethanol. To this solution, 0.94 ml (0.094 mmol) of a 0.1N aqueous solution of sodium hydroxide was added, and the mixture was stirred in an atmosphere of argon at room temperature for 40 minutes.

The reaction mixture was then concentrated, dissolved in water and subjected to freeze-drying, whereby sodium (E)-7-[6-(4'-fluorophenyl)-2,3-dihydro-7-[2-(2-methoxyethoxy)ethoxy]-2,2-dimethyl-4-(propan-2-yl)benzo[b]furan-5-yl]-3,5-dihydroxy-6-heptenoate (Compound 31) was obtained in the form of a colorless, amorphous solid in a yield of 52 mg (95.1%).

$^1$HNMR (300 MHz, CDCl$_3$)

δ 1.13(d, J=6.8Hz, 6H), 1.02–1.38 (m, 2H), 1.48 (s, 6H), 2.00–2.40 (m, 2H), 3.10 (s, 2H), 3.19–3.35 (m, 1H), 3.30 (s, 3H), 3.39 (s, 4H), 3.45 (t, J=5.2Hz, 2H), 3.91 (t, J=5.2Hz, 2H), 3.90–4.00 (m, 1H), 4.03–4.14 (m, 1H), 5.06 (dd, J=15.9 and 6.0Hz, 1H), 6.23 (d, J=15.9Hz, 1H), 6.84–6.96 (m, 2H), 7.00–7.13 (m, 2H)ppm.

IR (KBr): 3432, 2968, 2932, 1574, 1514 cm$^{-1}$.

Mass (FAB-neg, m/z, % ): 581 ([M-H]$^-$, 3), 559 (100).

EXAMPLE 27

Ethyl (E)-7-[ 6-(4 '-fluorophenyl)-2,3-dihydro-2,2 -dimethyl-4-(propan-2-yl)-7-(3-pyridylmethyloxy)benzo -[b] furan-5-yl ] -3,5-dihydroxy-6-heptenoate:

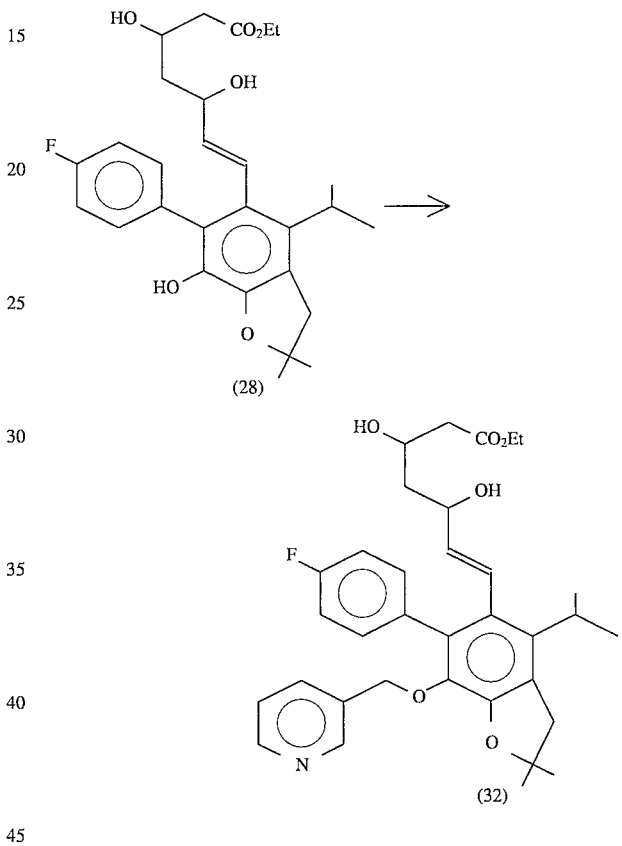

65 mg (0.134 mmol) of Compound 28 synthesized in Example 23 was dissolved in 2 ml of anhydrous DMF. To this solution, 92 mg (0.67 mmol) of potassium carbonate and 171 mg (1.34 mmol) of 3-chloromethylpyridine were added. This reaction mixture was stirred in an atmosphere of argon at room temperature for 3 hours and 30 minutes.

The reaction mixture was then added to water. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of ethyl acetate and hexane (2:1), whereby ethyl (E)-7-[6-(4'-fluorophenyl)-2,3 -dihydro-2,2-dimethyl-4-(propan-2-yl)-7-(3-pyridylmethyloxy)benzo[b]furan-5-yl]-3,5-dihydroxy-6-heptenoate (Compound 32) was obtained in a yield of 29 mg (37.5%).

Melting point: 117.0°–117.5° C. (colorless, particle-shaped crystals, recrystallized from a mixed solvent of ethyl acetate and hexane)

$^1$HNMR (300MHz, CDCl$_3$)

δ1.22 (d, J=7.1Hz, 3H), 1.23 (d, J=7.1Hz, 3H), 1.28 (t, J=7.1Hz, 3H), 1.10–1.43 (m, 2H), 1.54 (s, 6H), 2.32–2.46 (m, 2H), 2.72 (broad s, 1H), 3.16 (s, 2H), 3.28 (hept, J=7.1Hz, 1H), 3.58 (broad s, 1H), 3.98–4.10 (m, 1H), 4.18 (q, J=7.1Hz, 2H), 4.19– 4.30 (m, 1H), 4.83 (s, 2H), 5.09 (dd, J=16.0 and 6.6Hz, 1H), 6.32 (dd, J=16.0 and 1.0Hz, 1H), 6.92– 7.08 (m, 4H), 7.11 (dd, J=7.5 and 4.8Hz, 1H), 7.22– 7.26 (m, 1H), 8.27 (d, J=1.6Hz, 1H), 8.45 (dd, J=4.8 and 1.6Hz, 1H)ppm.

IR (KBr): 3448, 2976, 2936, 1738, 1602 cm$^{-1}$.

Mass (m/z, %): 577 (M$^+$, 11), 513 (33), 469 (29), 368 (40), 311 (35), 284 (39), 256 (100), 129 (43), 60 (47).

EXAMPLE 28

Sodium (E)-7-[ 6-(4 '-fluorophenyl)-2,3-dihydro-2,2 -dimethyl-4-(propan-2-yl)-7-(3-pyridylmethyloxy)benzo [ b] -furan-5-yl ] -3,5-dihydroxy-6-heptenoate:

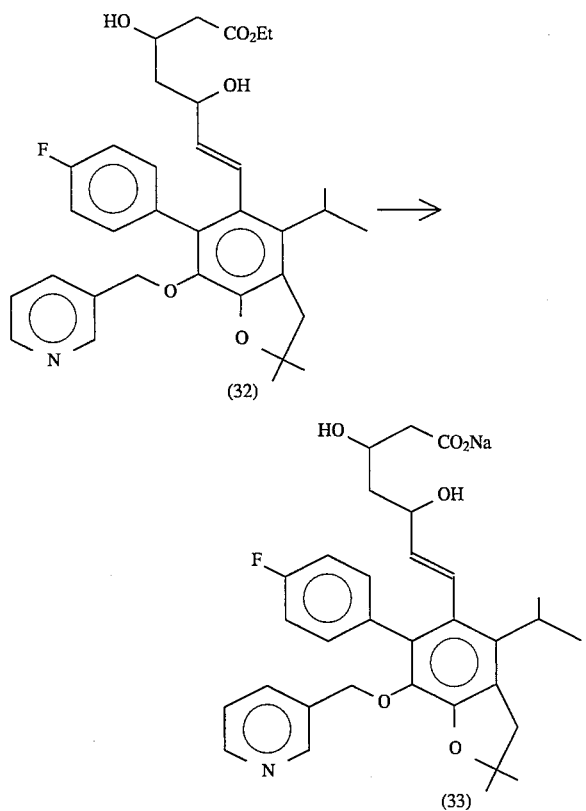

27 mg (0.047 mmol) of Compound 32 synthesized in Example 27 was dissolved in 1 ml of ethanol. To this solution, 0.47 ml (0,047 mmol) of a 0.1N aqueous solution of sodium hydroxide was added, and the mixture was stirred in an atmosphere of argon at room temperature for 45 minutes.

The reaction mixture was then concentrated, dissolved in water and subjected to freeze-drying, whereby sodium (E)-7-[6-(4'-fluorophenyl)-2,3-dihydro -2,2-dimethyl-4-(propan-2-yl)-7-(3-pyridylmethyloxy)benzo -[b]furan-5-yl]-3,5-dihydroxy-6-heptenoate (Compound 33) was obtained in the form of a colorless, amorphous solid in a quantitative yield.

$^1$HNMR (300MHz, CD$_3$OD)

δ1.25 (d, J=7.1Hz, 6H), 1.13–1.37 (m, 1H), 1.42–1.55 (m, 1H), 1.53 (s, 6H), 2.15 (dd, J=15.4 and 7.9Hz, 1H), 2.27 (dd, J=15.4 and 4.5Hz, 1H), 3.21 (s, 2H), 3.43 (hept, J=7.1Hz, 1H), 3.68–3.79 (m, 1H), 4.10–4.20 (m, 1H), 4.85 (s, 2H), 5.16 (dd, J=16.1 and 6.6Hz, 1H), 6.29 (dd, J=16.1 and 1.0Hz, 1H), 7.00–7.10 (m, 4H), 7.28 (dd with fine coupling, J=7.9 and 5.0Hz, 1H), 7.39–7.45 (m, 1H), 8.18 (d, J=1.6Hz, 1H), 8.38 (dd, J=5.0 and 1.6Hz, 1H)ppm.

IR (KBr): 3432, 2972, 2932, 1580, 1514 cm$^{-1}$.

Mass (FAB-neg, m/z, %): 570 ([M-H]$^-$, trace), 548 (100).

EXAMPLE 29

(E)-3-[ 4' -fluoro-6-methoxy-5-(2-methoxyethoxy)-3-(propan -2-yl)biphenyl-2-yl]-2-propenal:

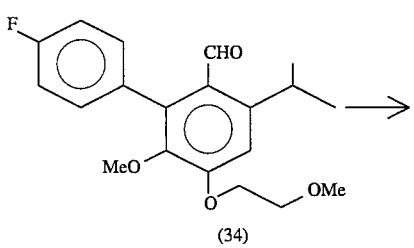

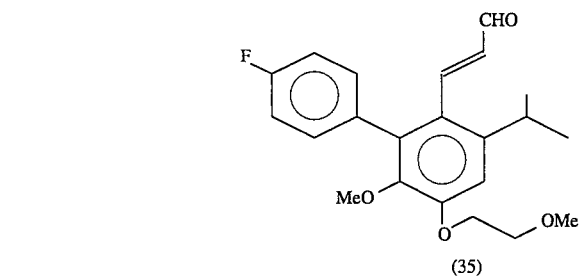

1.0 g (2.89 mmol) of 4'-fluoro-6-methoxy-5-(2 -methoxyethoxy)-3-(propan-2-yl)biphenyl-2-carbaldehyde (Compound 34) and 590 mg (3.76 mmol) of N-ethylidenecyclohexylamine were dissolved, with stirring, in 10 ml of anhydrous THF in an atmosphere of argon at 0° C.

To this solution, 356 mg (3.2 mmol) of potassium t-butoxide was added, and the mixture was stirred for 1 hour and 30 minutes.

This mixture, with addition of 6 ml of a 3N solution of hydrochloric acid thereto, was refluxed for 1 hour.

The reaction mixture was then poured into a saturated aqueous solution of sodium hydrogencarbonate, and the mixture was extracted with ethyl acetate. The extract layer was successively washed with water, and then with a saturated aqueous solution of sodium chloride, dried over magnesium sulfate, and concentrated.

The residue was chromatographed on silica gel and eluted with a mixed solvent of hexane and ethyl acetate (6:1), whereby (E)-3-[4'-fluoro-6-methoxy-5-(2 -methoxyethoxy)-3-(propan-2-yl)biphenyl-2-yl]-2-propenal (Compound 35) was obtained in a yield of 976 mg (90.8%).

Melting point: 90.0°–90.5° C. (colorless columns, recrystallized from a mixed solvent of hexane and dichloromethane)

$^1$HNMR (300 MHz, CDCl$_3$)

δ1.26 (d, J=6.8Hz, 6H), 3.27 (hept, J=6.8Hz, 1H), 3.47 (s, 3H), 3.53 (s, 3H), 3.82 (t, J=4.8Hz, 2H), 4.26 (t, J=4.8Hz, 2H), 5.89 (dd, J=16.2 and 7.8Hz, 1H), 6.98 (s, 1H), 7.05–7.10 (m, 2H), 7.14–7.19 (m, 2H), 7.29 (d, J=16.2Hz, 1H), 9.38 (d, J=7.8Hz, 1H)ppm.

IR (KBr): 2972, 2932, 1688, 1622, 1582 cm$^{-1}$.

Mass (m/z, %): 372 (M$^+$, 12), 329 (100), 271 (31), 59 (12).

EXAMPLE 30

Ethyl (E)-7-[4'-fluoro-6-methoxy-5-(2-methoxyethoxy)-3-(propan-2-yl)biphenyl-2-yl]-5-hydroxy-3-oxo-6-heptenoate:

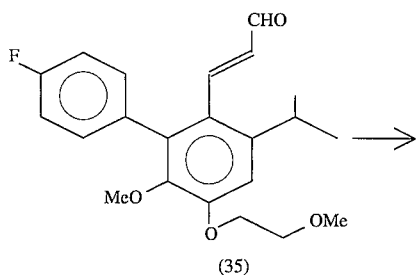

(35)

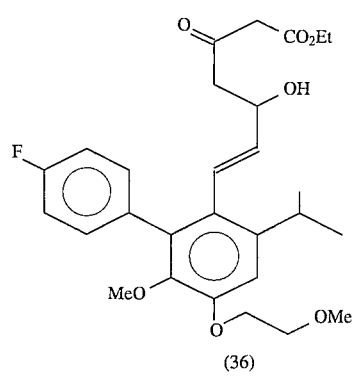

(36)

145 mg (3.63 mmol) of sodium hydride (60%) was suspended in 10 ml of anhydrous THF in an atmosphere of argon at 0° C. To this solution, 0.46 ml (3.63 mmol) of ethyl acetoacetate was added. This reaction mixture was stirred for 20 minutes. With the addition of 2.27 ml (3.63 mmol) of a 15% hexane solution of butyllithium thereto, the reaction mixture was further stirred for 15 minutes.

To this reaction mixture, 900 mg (2.42 mmol) of Compound 35 synthesized in Example 29 was added.

This mixture was then stirred at 0° C. for 30 minutes and was added to a 1N solution of hydrochloric acid.

This mixture was then extracted with ethyl acetate. The extract layer was successively washed with water, and then with a saturated aqueous solution of sodium, dried over magnesium sulfate, and concentrated.

The residue was chromatographed on silica gel and eluted with a mixed solvent of hexane and ethyl acetate (4:1), whereby ethyl (E)-7-[4'-fluoro-6-methoxy-5-(2 -methoxyethoxy)-3-(propan-2-yl)biphenyl-2-yl]-5-hydroxy-3 -oxo-6-heptenoate (Compound 36) was obtained in the form of a yellow oil in a yield of 1.09 g (89.7%).

$^1$HNMR (300 MHz, CDCl$_3$)

δ1.20 (d, J=6.8Hz, 3H), 1.21 (d, J=6.8Hz, 3H), 1.28 (t, J=7.2Hz, 3H), 2.38–2.46 (m, 2H), 3.17 (hept, J=6.8Hz, 1H), 3.40 (s, 2H), 3.47 (s, 3H), 3.52 (s, 3H), 3.80 (t, J=4.9Hz, 2H), 4.16–4.23 (m, 1H), 4.22 (q, J=7.2Hz, 2H), 4.42–4.52 (m, 1H), 5.14 (dd, J=16.2 and 6.3Hz, 1H), 6.37 (dd, J=16.2 and 1.3Hz, 1H), 6.90 (s, 1H), 7.02–7.08 (m, 2H), 7.14–7.17 (m, 2H)ppm.

IR (liquid film): 3484, 2968, 2936, 1744, 1716 cm$^{-1}$.

Mass (m/z, %): 502 (M$^+$, 2), 484 (2), 372 (12), 329 (100), 271 (31).

EXAMPLE 31

Ethyl (E)-7-[4'-fluoro-6-methoxy-5-(2-methoxyethoxy)-3-(propan-2-yl)biphenyl-2-yl]-3,5-dihydroxy-6-heptenoate:

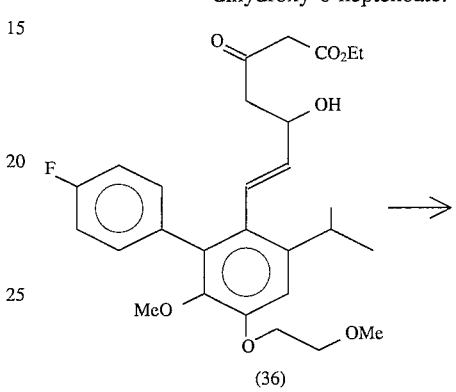

(36)

(37)

1.01 g (2.01 mmol) of Compound 36 synthesized in Example 30 was dissolved, with stirring, in a mixed solvent of 7.2 ml of anhydrous THF and 2.4 ml of methanol in an atmosphere of argon at –78° C. by using a cooling bath.

To this solution, 2.41 ml (2.41 mmol) of a 1.0 M THF solution of diethylmethoxyborane was added, and the mixture was stirred at room temperature for 15 minutes, with the removal of the cooling bath at –78° C.

This reaction mixture was again cooled to –78° C., and 114 mg (3.01 mmol) of sodium borohydride was added thereto. The reaction mixture was stirred for 2 hours.

The reaction mixture was then gradually added, with stirring, to 2.3 ml of 30% hydrogen peroxide at 0° C., and the mixture was stirred at room temperature overnight.

This mixture was then added to a saturated aqueous solution of sodium chloride. This mixture was extracted with ethyl acetate.

The extract layer was successively washed with a saturated aqueous solution of sodium chloride, an aqueous solution of sodium thiosulfate, and a saturated aqueous solution of sodium chloride, dried over magnesium sulfate, and concentrated.

The residue was chromatographed on silica gel and eluted with a mixed solvent of hexane and ethyl acetate (1:1), whereby ethyl (E)-7-[4'-fluoro-6-methoxy-5-(2 -methoxyethoxy)-3-(propan-2-yl)biphenyl-2-yl]-3,5 -dihydroxy-6-heptenoate (Compound 37) was obtained in the form of a colorless oil in a yield of 922 mg (91.0%).

¹HNMR (300 MHz, CDCl₃)

δ1.18–1.24 (m, 1H), 1.20 (d, J=6.8Hz, 3H), 1.21 (d, J=6.8Hz, 3H), 1.26 (t, J=7.2Hz, 3H), 1.34–1.47 (m, 1H), 2.38–2.42 (m, 2H), 2.78 (broad s, 1H), 3.20 (hept, J=6.8Hz, 1H), 3.46 (s, 3H), 3.52 (s, 3H), 3.58 (s with fine coupling, 1H), 3.79 (t, J=4.8Hz, 2H), 4.00–4.11 (m, 1H), 4.19 (q, J=7.2Hz, 2H), 4.22 (t, J=4.8Hz, 2H), 4.24–4.32 (m, 1H), 5.16 (dd, J=16.1 and 6.5Hz, 1H), 6.33 (dd, J=16.1 and 1.0Hz, 1H), 6.90 (s, 1H), 7.00–7.06 (m, 2H), 7.14–7.16 (m, 2H)ppm.

IR (liquid film): 3464, 2964, 2936, 1734, 1602, 1588 cm⁻¹.

Mass (m/z, %): 504 (M⁺, 14), 486 (43), 468 (48), 458 (36), 440 (79), 371 (34), 59 (100).

EXAMPLE 32

Sodium (E)-7-[ 4'-fluoro-6-methoxy-5-(2-methoxyethoxy)-3 (propan-2-yl)biphenyl-2-yl ]-3,5-dihydroxy-6-heptenoate:

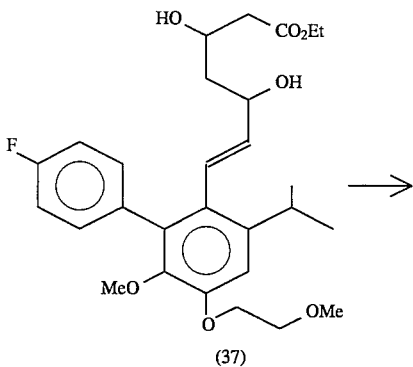

(37)

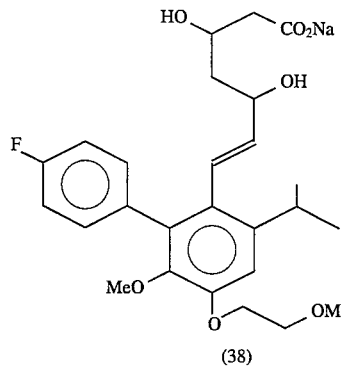

(38)

772 mg (1.53 mmol) of Compound 37 synthesized in Example 31 was dissolved in 5 ml of ethanol. To this solution, 1.53 ml (1.53 mmol) of a 1N aqueous solution of sodium hydroxide was added, and the mixture was stirred in an atmosphere of argon at 0° C. for 1 hour.

The reaction mixture was then concentrated, dissolved in water and subjected to freeze-drying, whereby sodium (E)-7-[4'-fluoro-6-methoxy-5-(2-methoxy -ethoxy)-3-(propan-2-yl)biphenyl-2-yl]-3,5-dihydroxy-6 -heptenoate (Compound 38) was obtained in the form of a colorless, amorphous solid in a quantitative yield.

¹HNMR (300 MHz, CD₃OD)

δ1.26 (d, J=6.8Hz, 6H), 1.29–1.33 (m, 1H), 1.51– 1.61 (m, 1H), 2.20 (dd, J=15 4 and 7.8 Hz, 1H), 2.32 (dd, J=15.4 and 4.4Hz, 1H), 3.37 (hept, J=6.8 Hz, 1H), 3.48 (s, 3H), 3.58 (s, 3H), 3.75–3.83 (m, 1H), 3.82 (t, J=4.6Hz, 2H), 4.17–4.25 (m, 1H), 4.25 (t, J=4.6Hz, 2H), 5.25 (dd, J=16.2 and 6.7Hz, 1H), 6.34 (dd, J=16.2 and 1.1Hz, 1H), 7.01 (s, 1H), 7.09–7.24 (m, 4H)ppm.

IR (KBr): 3420, 2964, 2932, 1582 cm⁻¹.

Mass (FAB-neg, m/z, %): 497 ([M-H]⁻, 11), 475 (100).

EXAMPLE 33

(E)-3-[ 4' -fluoro-5-[ 2-(2-tetrahydropyranyloxy)ethoxy]-6 -methoxy-3-(propan-2-yl)biphenyl-2-yl ]-2-propenenitrile:

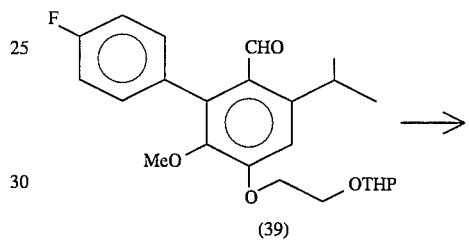

(39)

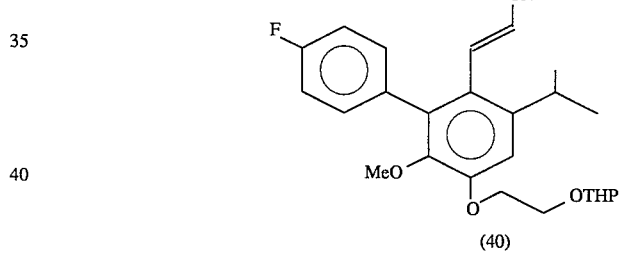

(40)

In an argon atmosphere, 143 mg (3.58 mmol) of a 60% sodium hydride was suspended in 15 ml of anhydrous THF. To this suspension, 0.58 ml (3.58 mmol) of diethyl cyanomethylphosphonate was added, and the mixture was stirred at 0° C.

To this reaction mixture, a solution of 1.42 g (3.41 mmol) of 4'-fluoro-5-[2-(2-tetrahydropyranyloxy)ethoxy]-6-methoxy-3-(propan-2-yl)biphenyl-2-yl]-2-carbaldehyde (Compound 39) in 10 ml of THF, was added dropwise, with stirring, and this reaction mixture was stirred was then stirred for 20 minutes.

The reaction mixture was then added to a 1N solution of hydrochloric acid. This mixture was extracted with ethyl acetate.

The ethyl acetate extract layer was successively washed with water and then with a saturated aqueous solution of sodium chloride, dried over magnesium sulfate, and then concentrated.

The residue was then crystallized from hexane, whereby (E)-3-[4'-fluoro-5-[2-(2-tetrahydropyranyloxy)ethoxy]-6-methoxy-3-(propan-2-yl)biphenyl-2-yl]-2-propenenitrile (Compound 40) was obtained in a yield of 1.28 g (82.5%).

The filtrate obtained in the crystallization was concentrated, chromatographed on silica gel and eluted with a mixed solvent of hexane and ethyl acetate (4:1), whereby Compound 40 was also obtained in a yield of 80 mg (5.2%).

Melting point: 131.5°–133.0° C. (colorless, fine particle-shaped crystals, recrystallized from hexane)

¹HNMR (300 MHz, CDCl₃)

δ1.25 (d, J=6.8Hz, 6H), 1.47–1.90 (m, 6H), 3.17 (hept, J=6.8Hz, 1H ), 3.52 (3H), 3.50–3.58 (m, 1H), 3.82–3.98 (m, 2H), 4.08–4.16 (m, 1H), 4.27 (t, J=5.0Hz, 2H), 4.72–4.75 (m, 1H), 4.91 (d, J=17.0Hz, 1H), 6.94 (s, 1H), 7.04–7.18 (m, 4H), 7.29 (d, J=17.0Hz, 1H)ppm.

IR (KBr): 2960, 2220, 1622, 1588 cm⁻¹.

Mass (m/z, % ): 439 (M⁺, 64 ), 356 (21 ), 355 (90 ), 315 (37 ), 311 (15 ), 271 (31 ), 129 (100), 85 (38).

EXAMPLE 34

(E)-3-[ 4' -fluoro-5-[ 2-(2-tetrahydropyranyloxy)ethoxy] -6 -methoxy-3-(propan-2-yl)biphenyl-2-yl ] -2-propenal:

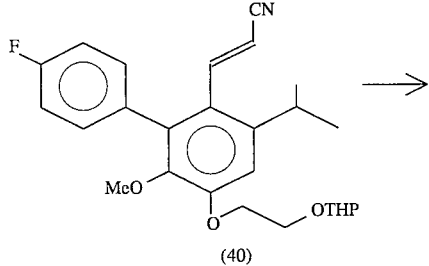

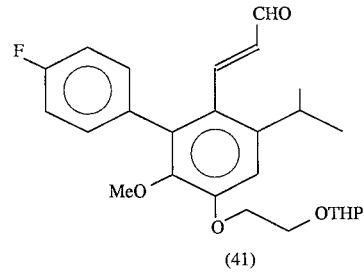

1.34 g (2.95 mmol) of Compound 40 synthesized in Example 33 was dissolved in 10 ml of anhydrous toluene. To this solution, 1.76 ml (3.10 mmol) of a 25% hexane solution of diisobutylaluminum hydride was added at −78° C. in an atmosphere of argon, and this mixture was stirred for 1 hour and 15 minutes.

To this reaction mixture which was at −78° C. was then added methanol, with stirring, and this mixture was then added to a mixed solvent of a 1N solution of hydrochloric acid and ethyl acetate. This mixture was stirred at room temperature for 1 hour and 30 minutes.

The ethyl acetate layer of the mixture was separated and successively washed with water and then with a saturated aqueous solution of sodium chloride, dried over magnesium sulfate, and concentrated.

The residue was chromatographed on silica gel and eluted with a mixed solvent of hexane and ethyl acetate (2:1), whereby (E)-3-[4'-fluoro-5-[2-(2-tetrahydropyranyloxy)ethoxy]-6-methoxy-3-(propan-2-yl)biphenyl-2-yl]-2-propenal (Compound 41) was obtained in a yield of 1.124 g (83.2%).

Melting point: 86.5°–88.0° C. (colorless, fine particle-shaped crystals, recrystallized from hexane)

¹HNMR (300 MHz, CDCl₃)

δ1.27 (d, J=6.8Hz, 6H), 1.46–1.90 (m, 6H), 3.27 (hept, J=6.8 Hz, 1H), 3.54 (s, 3H), 3.50–3.59 (m, 1H), 3.82–3.96 (m, 2H), 4.09–4.18 (m, 1H), 4.29 (t, J=5.0Hz, 2H), 4.74 (dd, J=3.5 and 3.0Hz, 1H), 5.89 (dd, J=16.3 and 7.8Hz, 1H), 6.98 (s, 1H), 7.02–7.12 (m, 2H), 7.13–7.20 (m, 2H), 7.29 (d, J=16.3Hz, 1H), 9.37 (d, J=7.8 Hz, 1H)ppm.

IR (KBr): 2960, 1682, 1622, 1584 cm⁻¹.

Mass (m/z, %): 442 (M⁺, 8), 399 (57 ), 315 (100 ), 271 (43), 129 (29).

EXAMPLE 35

Ethyl (E)-7-[ 4'-fluoro-5-[ 2-(2-tetrahydropyranyloxy)ethoxy]-6-methoxy-3-(propan-2-yl)biphenyl-2-yl ]-5 -hydroxy-3-oxo-6-heptenoate:

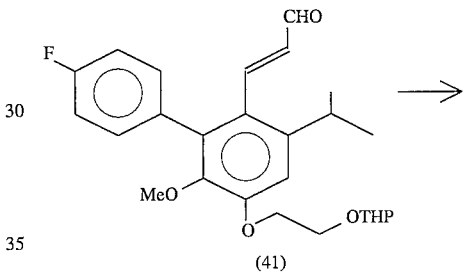

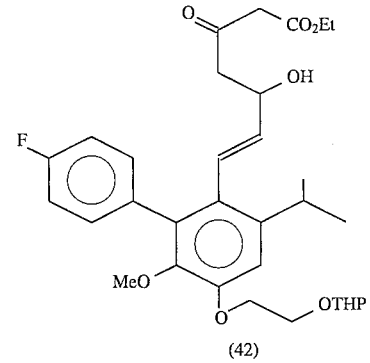

135 mg (3.38 mmol) of sodium hydride (60%) was suspended in 10 ml of anhydrous THF in an atmosphere of argon at 0° C. To this solution, 0.43 ml (3.38 mmol) of ethyl acetoacetate was added, and this mixture was stirred for 25 minutes. With the addition of 2.09 ml (3.38 mmol) of a 15% hexane solution of butyllithium thereto, the reaction mixture was further stirred for 25 minutes.

To this reaction mixture was added 1.19g (2.60 mmol) of Compound 41 synthesized in Example 34, and this mixture was stirred at 0° C. for 1 hour and 35 minutes and was then added to a 1N solution of hydrochloric acid.

This mixture was then extracted with ethyl acetate. The extract layer was successively washed with water, and then with a saturated aqueous solution of sodium chloride, dried over magnesium sulfate, and concentrated.

The residue was chromatographed on silica gel and eluted with a mixed solvent of hexane and ethyl acetate (1:1 to 2:1), whereby ethyl (E)-7-[4'-fluoro-5-[2-(2-tetrahydropyranyloxy)ethoxy]-6-methoxy-3-(propan-2-yl)biphenyl-2-yl]-5-hydroxy-3-oxo-6-heptenoate (Compound 42) was obtained in the form of a yellow oil in a yield of 1.17 g (76.5%).

¹HNMR (300 MHz, CDCl₃)

δ1.20 (d, J=6.8Hz, 3H), 1.21 (d, J=6.8Hz, 1H) 1.28 (t, J=7.0Hz, 3H), 1.46–1.90 (m, 6H), 2.32–2.49 (m, 2H), 3.17 (hept, J=6.8Hz, 1H), 3.40 (s, 2H), 3.54 (s, 3H), 3.50–3.58 (m, 1H), 3.81–3.96 (m, 2H), 4.06–4.27 (m, 2H), 4.20 (q, J=7.0Hz, 2H), 4.25 (t, J=5.1Hz, 2H), 4.43–4.52 (m, 1H), 4.74 (t, J=3.3Hz, 1H), 5.14 (dd, J=16.1 and 6.2Hz, 1H), 6.36 (dd, J=16.1 and 1.1Hz, 1H), 6.90 (s, 1H), 7.03–7.18 (m, 4H)ppm.

IR (liquid film): 3476, 2960, 1744, 1718, 1602, 1588 cm⁻¹.

Mass (m/z, %): 572 (M⁺, 0.2) 442 (9), 399 (73), 315 (100), 271 (59), 129 (34).

EXAMPLE 36

Ethyl (E)-7-[ 4 '-fluoro-5-[ 2-(2-tetrahydropyranyloxy)ethoxy ]-6-methoxy-3-(propan-2-yl)biphenyl-2-yl ] -3,5 -dihydroxy-6-heptenoate:

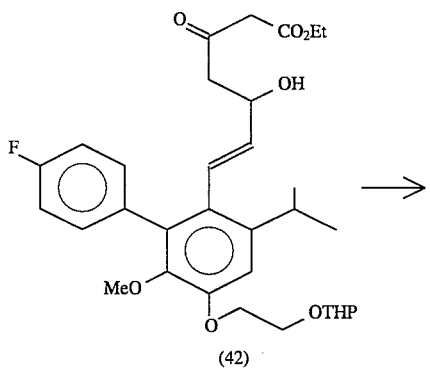

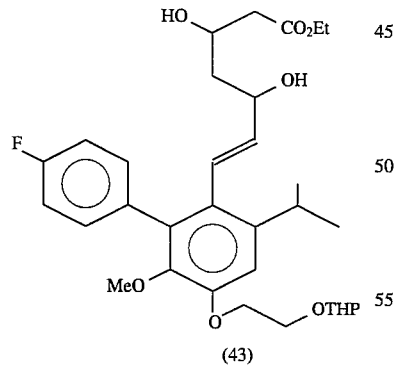

1.44 g (2.45 mmol) of Compound 42 synthesized in Example 35 was dissolved, with stirring, in a mixed solvent of 9 ml of anhydrous THF and 3 ml of methanol in an atmosphere of argon at −78° C. by using a cooling bath.

To this solution, 2.94 ml (2.94 mmol) of a 1.0 M THF solution of diethylmethoxyborane was added, and the mixture was stirred at room temperature for 15 minutes, with the removal of the cooling bath at −78° C.

This reaction mixture was again cooled to −78° C., and 139 mg (3.68 mmol) of sodium borohydride was added thereto. The reaction mixture was stirred for 55 minutes.

The reaction mixture was then gradually added, with stirring, to 2.8 ml of 30% hydrogen peroxide at 0° C., and the mixture was stirred at room temperature for 2 hours.

This reaction mixture was then added to a saturated aqueous solution of ammonium chloride. This mixture was extracted with ethyl acetate. The extract layer of this mixture was separated and successively washed with a saturated aqueous solution of sodium chloride, an aqueous solution of sodium thiosulfate, and a saturated aqueous solution of sodium chloride, dried over magnesium sulfate, and concentrated.

The residue was chromatographed on silica gel and eluted with a mixed solvent of hexane and ethyl acetate (1:1), whereby ethyl (E)-7-[4'-fluoro-5-[2-(2-tetrahydropyranyloxy)ethoxy]-6-methoxy-3-(propan-2-yl)biphenyl-2-yl]-3,5-dihydroxy-6-heptenoate (Compound 43) was obtained in a yield of 1.34 g (92.7%).

Melting point: 64.0°–65.0° C. (colorless needles, recrystallized from a mixed solvent of hexane and ethyl acetate)

¹HNMR (300 MHz, CDCl₃)

δ1.20 (d, J=6.8Hz,3H), 1.21 (d, J=6.8 Hz, 1H), 1.28 (t, J=7.2Hz, 3H), 1.17–1.30 (m, 1H), 1.35–1.45 (m, 1H), 1.50–1.90 (m, 6H), 2.35–2.44 (m, 2H), 2.76 (d, J=1.9Hz, 1H), 3.20 (hept, J=6.8 Hz, 1H), 3.48–3.56 (m, 1H), 3.54 (s, 3H), 3.57 (d, J=2.2Hz, 2H), 3.82–3.96 (m, 2H), 4.01–4.30 (m, 2H), 4.16 (q, J=7.2Hz, 2H), 4.25 (t, J=4.9Hz, 2H), 4.72–4.76 (m, 1H), 5.16 (dd, J=16.1 and 6.5Hz, 1H), 6.33 (dd, J=16.1 and 1.0Hz, 1H), 6.90 (s, 1H), 7.00–7.08 (m, 2H), 7.10–7.20 (m, 2H)ppm.

IR (KBr): 3536, 3428, 2964, 1716, 1602, 1588 cm⁻¹.

Mass (m/z, %): 574 (M⁺, 2), 556 (4), 510 (49 ), 426 (57), 129 (100).

EXAMPLE 37

Ethyl (E)-7-[ 4'-fluoro-5-(2-hydroxyethoxy)-6-methoxy-3 -(propan-2-yl)biphenyl-2-yl ] -3,5-dihydroxy-6-heptenoate:

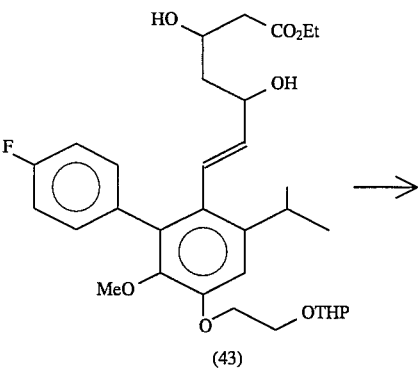

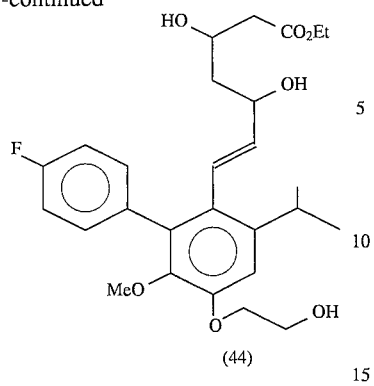

(44)

1.21 g (2.05 mmol) of Compound 43 synthesized in Example 36 and ].03 mg (0.41 mmol) of pyridinium p-toluenesulfonate were dissolved in 15 ml of methanol.

This solution was stirred at room temperature for 6 hours and 25 minutes.

This reaction mixture was added to water, and the mixture was extracted with ethyl acetate.

The extract layer of the mixture was successively washed with a saturated aqueous solution of sodium chloride, dried over magnesium sulfate, and concentrated.

The residue was chromatographed on silica gel and eluted with a mixed solvent of ethyl acetate and hexane (2:1), whereby ethyl (E)-7-[4'-fluoro-5-(2-hydroxy-ethoxy)-6-methoxy-3-(propan-2-yl)biphenyl-2-yl]-3,5-dihydroxy-6-heptenoate (Compound 44) was obtained in the form of a colorless oil in a yield of 768 mg (74.0%).

$^1$HNMR (300 MHz, CDCl$_3$)

δ1.20 (d, J=6.8Hz, 3H), 1.21 (d, J=6.8Hz, 1H), 1.28 (t, J=7.2Hz, 3H), 1.18–1.32 (m, 1H), 1.34–1.48 (m, 1H), 2.33–2.48 (m, 2H), 2.85 (d, J=1.9Hz, 1H), 3.21 (hept, J=6.8Hz, 1H), 3.49 (s, 3H), 3.59 (d, J=2.3Hz, 1H), 3.92–3.99 (m, 2H), 4.01–4.11 (m, 1H), 4.12 (q, J=7.2Hz, 2H), 4.13–4.22 (m, 3H), 4.23–4.33 (m, 1H), 5.17 (dd, J=16.1 and 6.5Hz, 1H), 6.34 (dd, J=16.1 and 1.2Hz, 1H), 6.90 (s, 1H), 7.00–7.09 (m, 2H), 7.12–7.18 (m, 2H)ppm.

IR (liquid film): 3424, 2964, 2936, 1732, 1588 cm$^{-1}$.

Mass (m/z, %): 490 (M$^+$, 27), 473 (13), 472 (43), 454 (15), 426 (100), 357 (33), 341 (36), 315 (34), 45 (41).

EXAMPLE 38

Sodium (E)-7-[4'-fluoro-5-(2-hydroxyethoxy)-6-methoxy-3-(propan-2-yl) biphenyl-2-yl]-3,5-dihydroxy-6-heptenoate:

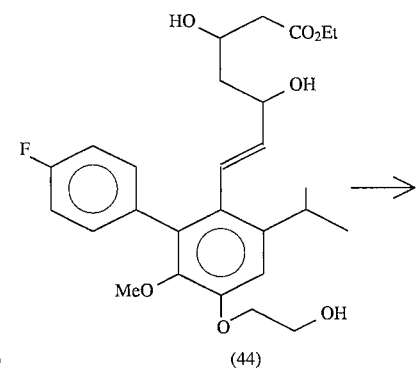

(44)

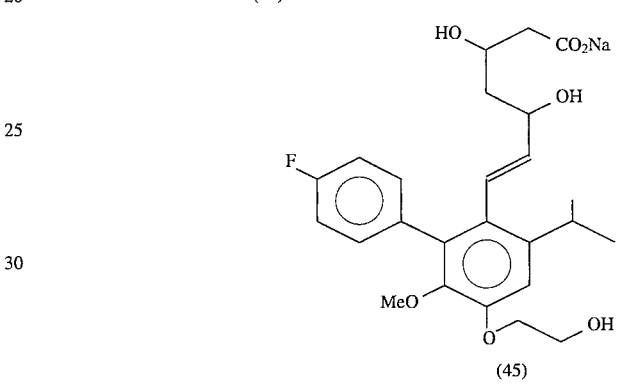

(45)

682 mg (1.39 mmol) of Compound 44 synthesized in Example 37 was dissolved in 8 ml of ethanol. To this solution, 1.39 ml (1.39 mmol) of a 1N aqueous solution of sodium hydroxide was added, and the mixture was stirred in an atmosphere of argon at 0° C. for 1 hour.

The reaction mixture was then concentrated, dissolved in water and subjected to freeze-drying, whereby sodium (E)-7-[4'-fluoro-5-(2-hydroxyethoxy)-6-methoxy-3-(propan-2-yl)biphenyl-2-yl]-3,5-dihydroxy-6-heptenoate (Compound 45) was obtained in the form of a colorless, amorphous solid in a yield of 664 mg (98.7% ).

$^1$HNMR (300 MHz, CD$_3$OD)

δ1.27 (d, J=6.8 Hz, 6H), 1.26–1.35 (m, 1H), 1.51–1.62 (m, 1H), 2.20 (dd, J=15.4 and 7.9Hz, 1H), 2.32 (dd, J=15.4 and 4.5Hz, 1H), 3.35 (hept, J=6.8Hz, 1H), 3.54 (s, 3H), 3.76–3.84 (m, 1H), 3.92–3.96 (m, 2H), 4.14–4.26 (m, 3H), 5.26 (dd, J=16.1 and 6.6Hz, 1H), 6.34 (dd, J=16.1 and 1.1Hz, 1H), 7.02 (s, 1H), 7.08–7.26 (m, 4H)ppm.

IR (KBr): 3424, 2964, 1582 cm$^{-1}$.

Mass (FAB-neg, m/z, %): 483 ([M-H]$^-$, 16 ), 461 (100 ).

EXAMPLE 39

(E)-3-[ 4'-fluoro-6-methoxy-5-[
2-(2-methoxyethoxy)ethoxy]
-3-(propan-2-yl)biphenyl-2-yl ]-2-propenal:

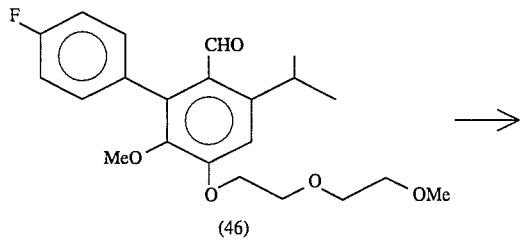
(46)

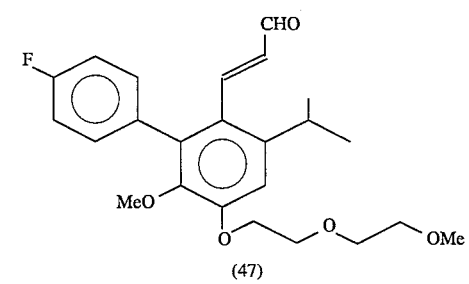
(47)

800 mg (2.05 mmol) of 4'-fluoro-6-methoxy-5-[2-(2-methoxyethoxy)ethoxy]-3-(propan-2-yl)biphenyl-2-carbaldehyde (Compound 46), and 502 mg (5.04 mmol) of N-ethylidenecyclohexylamine were dissolved in 10 ml of anhydrous THF in an atmosphere of argon at 0° C.

To this solution, 242 mg (2.15 mmol) of potassium t-butoxide was added, and this reaction mixture was stirred for 3 hours and 10 minutes.

This reaction mixture, with the addition of 2 ml of a 3N solution of hydrochloric acid thereto, was refluxed for 50 minutes.

The reaction mixture was then added to a saturated aqueous solution of sodium hydrogencarbonate, and this mixture was extracted with ethyl acetate.

The extract layer of the mixture was successively washed with water, a saturated aqueous solution of sodium chloride, dried over magnesium sulfate, and concentrated.

The residue was chromatographed on silica gel and eluted with a mixed solvent of hexane and ethyl acetate (2:1), whereby (E)-3-[4'-fluoro-6-methoxy-5-[2-(2-methoxyethoxy)ethoxy]-3-(propan-2-yl)biphenyl-2-yl]-2 -propenal (Compound 47) was obtained in the form of a yellow oil in a yield of 768 mg (90.1%).

$^1$HNMR (300 MHz, CDCl$_3$)

δ1.26 (d, J=6.8Hz, 6H), 3.27 (hept, J=6.8Hz, 1H), 3.39 (s, 3H), 3.53 (s, 3H), 3.53–3.61 (m, 2H), 3.71–3.78 (m, 2H), 3.90–3.97 (m, 2H), 4.25–4.32 (m, 2H), 5.88 (dd, J=16.2 and 7.8Hz, 1H), 6.97 (s, 1H), 7.02–7.20 (m, 4H), 7.29 (d, J=16.3Hz, 1H), 9.37 (d, J=7.7Hz, 1H)ppm.

IR (liquid film): 2964, 2936, 2876, 1678, 1620 cm$^{-1}$.

Mass (m/z, %): 416 (M$^+$, 10), 373 (100), 271 (28), 103 (13), 59 (20).

EXAMPLE 40

Ethyl (E)-7-[ 4'-fluoro-6-methoxy-5-[
2-(2-methoxyethoxy)ethoxy]-3-(propan-2-
yl)biphenyl-2-yl ]-5-hydroxy-3-oxo-6-heptenoate:

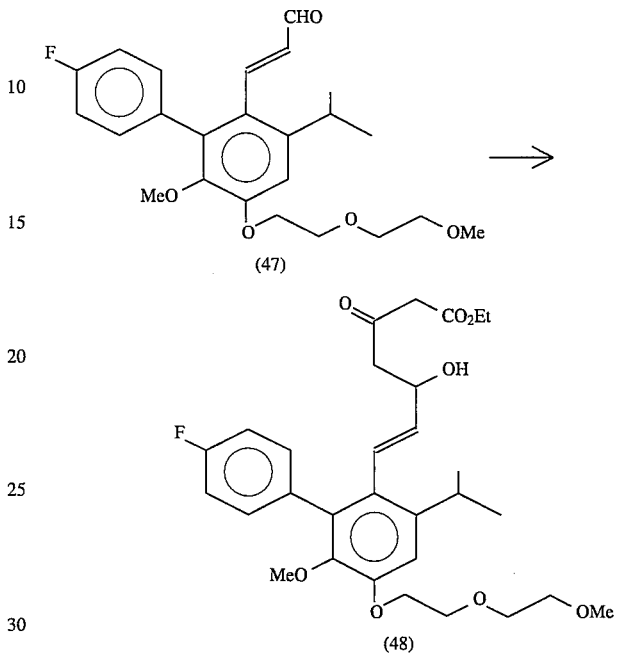

88 mg (2.21 mmol) of sodium hydride (60%) was suspended in 6 ml of anhydrous THF in an atmosphere of argon at 0° C. To this solution, 0.28 ml (2.21 mmol) of ethyl acetoacetate was added. This reaction mixture was stirred for 25 minutes. With the addition of 1.36 ml (2.21 mmol) of a 15% hexane solution of butyllithium thereto, the reaction mixture was further stirred for 25 minutes.

To this reaction mixture, 707 mg (1.70 mmol) of Compound 47 synthesized in Example 39 was added.

This mixture was then stirred at 0° C. for 1 hour and 5 minutes and added to a 1N solution of hydrochloric acid.

This mixture was then extracted with ethyl acetate. The extract layer was successively washed with water, and then with a saturated aqueous solution of sodium chloride, dried over magnesium sulfate, and concentrated.

The residue was chromatographed on silica gel and eluted with a mixed solvent of hexane and ethyl acetate (1:1), whereby ethyl (E)-7-[4'-fluoro-6-methoxy-5-[2 -(2-methoxyethoxy)ethoxy]-3-(propan-2-yl)biphenyl-2-yl]-5 -hydroxy-3-oxo-6-heptenoate (Compound 48) was obtained in the form of a yellow oil in a yield of 725 mg (78.1%).

$^1$HNMR (300 MHz, CDCl$_3$)

δ1.19 (d, J=6.8Hz, 3H), 1.20 (d, J=6.8Hz, 3H), 1.28 (t, J=7.1Hz, 3H), 2.32–2.48 (m, 2H), 3.17 (hept, J=6.8Hz, 1H), 3.39 (s, 3H), 3.40 (s, 2H), 3.49–3.52 (m, 1H), 3.52 (s, 3H), 3.56–3.60 (m, 2H), 3.71–3.76 (m, 2H), 3.91 (t, J=5.1Hz, 2H), 4.20 (q, J=7.1Hz, 2H), 4.24 (t, J=5.1Hz, 2H), 4.44–4.52 (m, 1H), 5.14 (dd, J=16.1 and 6.2Hz, 1H), 6.36 (dd, J=16.1 and 1.2Hz, 1H), 6.88 (s, 1H), 7.02–7.10 (m, 2H), 7.11–7.18 (m, 2H)ppm.

IR (liquid film): 3464, 2964, 2932, 1744 1716, 1602, 1588 cm$^{-1}$.

Mass (m/z, %): 546 (M$^+$, 0.5), 416 (10), 373 (100), 103 (14), 59 (18).

EXAMPLE 41

Ethyl (E)-7-[ 4'-fluoro-6-methoxy-5-[ 2-(2-methoxyethoxy)ethoxy]-3-(propan-2-yl)biphenyl-2-yl ]-3,5-dihydroxy-6-heptenoate:

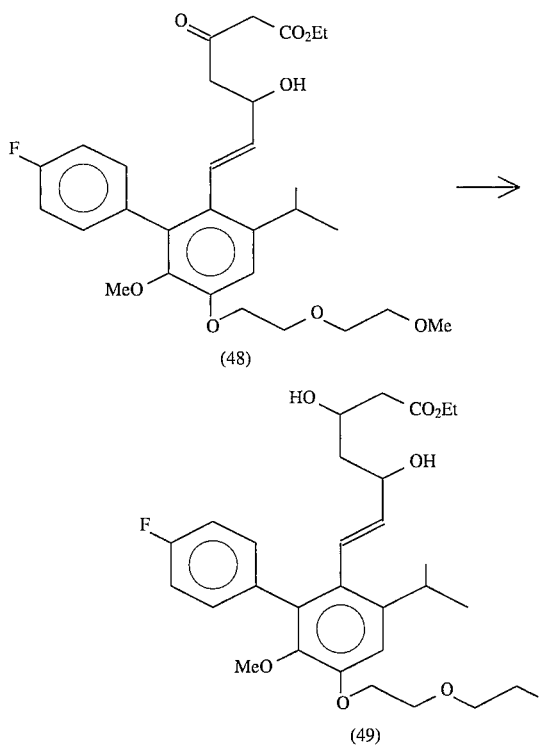

659 mg (1.21 mmol) of Compound 48 synthesized in Example 40 was dissolved, with stirring, in a mixed solvent of 4.5ml of anhydrous THF and 1.5 ml of methanol in an atmosphere of argon at −78° C. by using a cooling bath.

To this solution, 1.45 ml (1.45 mmol) of a 1.0 M THF solution of diethylmethoxyborane was added, and the mixture was stirred at room temperature for 20 minutes, with the removal of the cooling bath at −78° C.

This reaction mixture was again cooled to −78° C., and 69 mg (1.82 mmol) of sodium borohydride was added thereto. The reaction mixture was stirred for 40 minutes.

The reaction mixture was then gradually added, with stirring, to 1.37 ml of a 30% hydrogen peroxide solution at 0° C., and the mixture was stirred at room temperature overnight.

This reaction mixture was then added to a saturated aqueous solution of sodium chloride. This mixture was extracted with ethyl acetate. The extract layer was successively washed with a saturated aqueous solution of sodium chloride, an aqueous solution of sodium thiosulfate, and a saturated aqueous solution of sodium chloride, dried over magnesium sulfate, and concentrated.

The residue was chromatographed on silica gel and eluted with a mixed solvent of hexane and ethyl acetate (1:1), whereby ethyl (E)-7-[4'-fluoro-6-methoxy-5-[2 -(2-methoxyethoxy)ethoxy]-3-(propan-2-yl)biphenyl-2-yl]-3,5-dihydroxy-6-heptenoate (Compound 49) was obtained in the form of a colorless oil in a yield of 583 mg (88.0%).

$^1$HNMR (300 MHz, CDCl$_3$)

δ1.16–1.48 (m, 2H), 1.20 (d, J=6.8Hz, 3H), 1.21 (d, J=6.8Hz, 3H), 1.28 (t, J=7.2Hz, 3H), 2.32–2.50 (m, 2H), 2.78 (broad s, 1H), 3.20 (hept, J=6.8Hz, 1H), 3.39 (s, 3H), 3.52 (s, 3H), 3.52–3.60 (m, 2H), 3.70–3.78 (m, 2H), 3.863.95 (m, 2H), 4.00–4.12 (m, 1H), 4.18 (q, J=7.2Hz, 2H), 4.18–4.33 (m, 3H), 5.16 (dd, J=16.1 and 6.5Hz, 1H), 6.33 (dd, J=16.1 and 1.0Hz, 1H), 6.89 (s, 1H), 6.98–7.09 (m, 2H), 7.09–7.19 (m, 2H)ppm.

IR (liquid film): 3468, 2964, 2936, 1734, 1602, 1588 cm$^{-1}$.

Mass (m/z, %): 548 (M$^+$, 7), 530 (19), 512 (18), 502 (16), 484 (100), 103 (71).

EXAMPLE 42

Sodium (E)-7-[ 4 '-fluoro-6-methoxy-5-[ 2-(2-methoxyethoxy)ethoxy ] -3-(propan-2-yl) biphenyl-2-yl ] -3,5-dihydroxy-6-heptenoate:

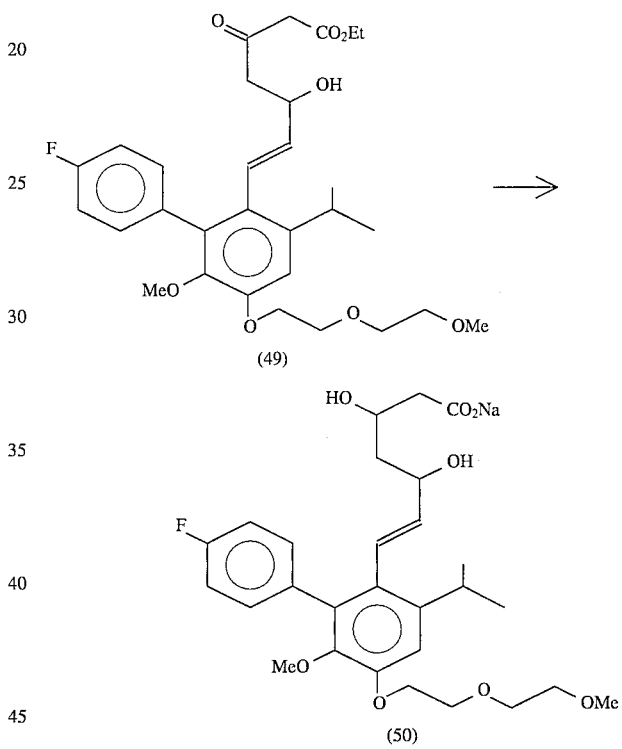

372 mg (0.68 mmol) of Compound 49 synthesized in Example 41 was dissolved in 6 ml of ethanol. To this solution, 0.68 ml (0.68 mmol) of a 1N aqueous solution of sodium hydroxide was added, and the mixture was stirred in an atmosphere of argon at 0° C. for 1 hour.

The reaction mixture was then concentrated, dissolved in water and subjected to freeze-drying, whereby sodium (E)-7-[4'-fluoro-6-methoxy-5-[2-(2-methoxyethoxy)ethoxy]-3-(propan-2-yl)biphenyl-2-yl]-3,5 -dihydroxy-6-heptenoate (Compound 50) was obtained in the form of a colorless, amorphous solid in a yield of 364 mg (98.9%).

$^1$HNMR (300 MHz, CD$_3$OD)

δ1.25–1.38 (m, 1H), 1.27 (d, J=6.8Hz, 6H), 1.56 (ddd, J=13.7, 8.9 and 7.3Hz, 1H), 2.20 (dd, J=15.4 and 7.9Hz, 1H), 2.32 (dd, J=15.4 and 4.4Hz, 1H), 3.36 (hept, J=6.8Hz, 1H), 3.40 (s, 3H), 3.54 (s, 3H), 3.58–3.62 (m, 2H), 3.74–3.78 (m, 2H), 3.74–3.84 (m, 1H), 3.88–3.93 (m, 2H), 4.17–4.30 (m, 1H), 4.25–4.29 (m, 2H), 5.25 (dd, J=16.1 and 6.6Hz, 1H), 6.34 (dd, J=16.1 and 1.1Hz, 1H), 7.02 (s, 1H), 7.10–7.25 (m, 4H)ppm.

IR (KBr): 3404, 2964, 2932, 1580 cm$^{-1}$.

Mass (FAB-neg, m/z, %): 541 ([M-H]$^-$, 11), 519 (100).

EXAMPLE 43

(E)-3-[ 4'-fluoro-6-methoxy-5-methyl-3-(propan-2-yl) biphenyl-2-yl ]-2-propenenitrile:

120 mg (3.0 mmol) of a 60% sodium hydride was suspended in 5 ml of anhydrous THF in an atmosphere of argon at 0° C. To this suspension, 0.51 ml (3.15 mmol) of diethyl cyanomethylphosphonate was added, and this mixture was stirred for 20 minutes.

To this reaction mixture, a solution of 725 mg (2.53 mmol) of 4'-fluoro-6-methoxy-5-methyl-3-(propan-2 -yl)biphenyl-2-carbaldehyde (Compound 51) in 5 ml of THF, was added dropwise, and the mixture was stirred for 20 minutes.

The reaction mixture was then added to a 1N solution of hydrogen chloride. This mixture was extracted with ethyl acetate. The extract layer was washed with a saturated aqueous solution of sodium chloride, dried over magnesium sulfate, and then concentrated.

The residue was then crystallized from a mixed solvent of ethyl acetate and ethanol, whereby (E)-3-[4'-fluoro-6-methoxy-5-methyl-3-(propan-2-yl)biphenyl-2-yl]-2-propenenitrile (Compound 52) was obtained in a yield of 510 mg (65.1%).

The filtrate obtained in the crystallization was concentrated, chromatographed on silica gel and eluted with a mixed solvent of dichloromethane and hexane (2:1), whereby Compound 52 was also obtained in a yield of 212 mg (27.1%).

Melting point: 176.0°–176.5° C. (colorless needles, recrystallized from a mixed solvent of ethyl acetate and ethanol)

$^1$HNMR (300 MHz, CDCl$_3$)

δ1.24 (d, J=6.8Hz, 6H), 2.34 (s, 3H), 3.10 (hept, J=6.8Hz, 1H), 3.27 (s, 3H), 4.98 (d, J=17.0Hz, 1H), 7.07–7.23 (m, 5H), 7.32 (d, J=17.0Hz, 1H)ppm.

IR (KBr): 2968, 2936, 2220, 1624, 1606 cm$^{-1}$.

Mass (m/z, %): 309 (M$^+$, 100), 295 (22), 294 (98), 279 (33), 269 (25).

EXAMPLE 44

(E)-3-[ 4'-fluoro-6-methoxy-5-methyl-3-(propan-2-yl) biphenyl-2-yl ]-2-propenal:

692 mg (2.24 mmol) of Compound 52 synthesized in Example 43 was dissolved in 10 ml of anhydrous toluene. To this solution, 1.34 ml (2.36 mmol) of a 25% hexane solution of diisobutylaluminum hydride was added in an atmosphere of argon at −78° C., and the mixture was then stirred for 20 minutes.

This reaction mixture was then added to a 1N solution of hydrochloric acid. The mixture was then extracted with ethyl acetate.

The extract layer was successively washed with water, and a saturated aqueous solution of sodium chloride, dried over magnesium sulfate, and concentrated.

The residue was chromatographed on silica gel and eluted with a mixed solvent of dichloromethane and hexane (1:1), whereby (E)-3-[4'-fluoro-6-methoxy-5-methyl-3 -(propan-2-yl)biphenyl-2-yl ]-2-propenal (Compound 53 ) was obtained in a yield of 612 mg (87.6%).

Melting point: 117.0°–117.5° C. (colorless needles, recrystallized from a mixed solvent of hexane and dichloromethane)

$^1$HNMR (300 MHz, CDCl$_3$)

δ1.25 (d, J=6.8 Hz, 6H), 2.35 (s, 3H), 3.19 (hept, J=6.8Hz, 1H), 3.29 (s, 3H), 5.94 (dd, J=16.3 and 7.8Hz, 1H), 7.03–7.13 (m, 2H), 7.17–7.25 (m, 2H), 7.21 (s, 1H), 7.33 (d, J=16.3Hz, 1H), 9.41 (d, J=7.8 Hz, 1H)ppm.

IR (KBr): 2968, 2936, 1688, 1626 cm$^{-1}$.

Mass (m/z, %): 312 (M$^+$, 26), 269 (100), 241 (12).

EXAMPLE 45

Ethyl (E)-7-[ 4'-fluoro-6-methoxy-5-methyl-3-(propan-2-yl) biphenyl -2-yl ] -5-hydroxy-3-oxo -6-heptenoate:

90 mg (2.25 mmol) of a 60% sodium hydride was suspended in 5 ml of anhydrous THF in an atmosphere of argon at 0° C. To this solution, 0.30 ml (2.25 mmol) of ethyl acetoacetate was added. This reaction mixture was stirred for 15 minutes. With the addition of 1.4 ml (2.25 mmol) of a 15% hexane solution of butyllithium thereto, the reaction mixture was further stirred for 15 minutes.

To this reaction mixture, 591 mg (1.89 mmol) of Compound 53 synthesized in Example 44 was added.

This mixture was then stirred at 0° C. for 15 minutes and added to a 1N solution of hydrochloric acid.

This mixture was then extracted with ethyl acetate. The extract layer was successively washed with water, and then with a saturated aqueous solution of sodium chloride, dried over magnesium sulfate, and concentrated.

The residue was chromatographed on silica gel and eluted with a mixed solvent of hexane and ethyl acetate (3:1), whereby ethyl (E)-7-[4'-fluoro-6-methoxy-5-methyl-3-(propan-2-yl)biphenyl-2-yl]-5-hydroxy-3-oxo-6 -heptenoate (Compound 54) was obtained in a yield of 717 mg (85.6%).

Melting point: 80.0°–81.0° C. (colorless needles, recrystallized from a mixed solvent of hexane and dichloromethane)

$^1$HNMR (300 MHz, CDCl$_3$)

δ1.20 (d, J=6.8Hz, 3H), 1.21 (d, J=6.8Hz, 3H), 1.28 (t, J=7.2Hz, 3H), 2.32 (s, 3H), 2.32–2.50 (m, 2H), 2.48 (d, J= 3.8Hz, 1H ), 3.14 (hept, J=6.8Hz, 1H ), 3.29 (s, 3H), 3.40 (s, 2H), 4.20 (q, J=7.2Hz, 2H), 4.43–4.53 (m, 1H), 5.16 (dd, J=16.1 and 6.2Hz, 1H), 6.41 (d, J=16.1Hz, 1H), 7.01–7.13 (m, 2H), 7.11 (s, 1H), 7.13–7.22 (m, 2H)ppm.

IR (KBr): 3460, 2968, 1724, 1706 1606 cm$^{-1}$.

Mass (m/z, %): 442 (M$^+$, 5), 424 (12), 312 (25), 270 (21), 269 (100), 253 (10).

EXAMPLE 46

Ethyl (E)-7-[ 4'-fluoro-6-methoxy-5-methyl-3-(propan-2-yl) biphenyl-2-yl ] -3,5-dihydroxy-6-heptenoate:

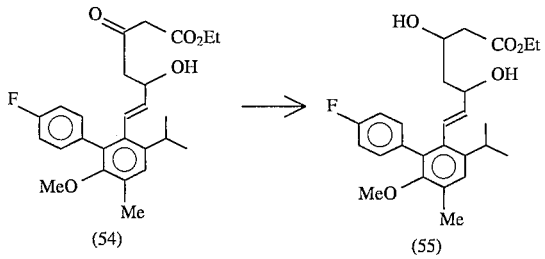

689 mg (1.56 mmol) of Compound 54 synthesized in Example 45 was dissolved, with stirring, in a mixed solvent of 8 ml of anhydrous THF and 2 ml of methanol in an atmosphere of argon at −78° C. by using a cooling bath.

To this solution, 1.80 ml (1.80 mmol) of a 1.0 M THF solution of diethylmethoxyborane was added, and the mixture was stirred at room temperature for 30 minutes, with the removal of the cooling bath at −78° C.

This reaction mixture was again cooled to −78° C., and 63 mg (1.66 mmol) of sodium borohydride was added thereto. The reaction mixture was stirred for 60 minutes.

The reaction mixture was then gradually added, with stirring, to 16 g of a 30% hydrogen peroxide solution at 0° C., and the mixture was stirred at room temperature overnight.

This reaction mixture was then added to a saturated aqueous solution of sodium chloride. This mixture was extracted with ethyl acetate. The extract layer was successively washed with a saturated aqueous solution of sodium chloride, an aqueous solution of sodium thiosulfate, and a saturated aqueous solution of sodium chloride, dried over magnesium sulfate, and concentrated.

The residue was chromatographed on silica gel and eluted with a mixed solvent of hexane and ethyl acetate (2:1), whereby ethyl (E)-7-[4'-fluoro-6-methoxy-5-methyl-3-(propan-2-yl)biphenyl-2-yl]-3,5-dihydroxy-6-heptenoate (Compound 55) was obtained in the form of a colorless oil in a yield of 570 mg (82.4%).

$^1$HNMR (300 MHz, CDCl$_3$ )

δ1.20 (d, J=6.8Hz, 3H), 1.21 (d, J=6.8Hz, 3H), 1.29 (t, J=7.1Hz, 3H), 2.32 (s, 3H), 2.34–2.48 (m, 2H), 2.82 (d, J= 2.1Hz, 1H ), 3.17 (hept, J=6.8Hz, 1H ), 3.29 (s, 3H), 3.58–3.62 (m, 1H), 4.01–4.14 (m, 1H), 4.18 (q, J=7.1Hz, 2H), 4.25–4.35 (m, 1H), 5.18 (dd, J=16.2 and 6.4Hz, 1H), 6.38 (d, J=16.2Hz, 1H), 7.00–7.10 (m, 2H), 7.11 (s, 1H), 7.13–7.23 (m, 2H)ppm.

IR (liquid film): 3416, 2968, 1736, 1604 cm$^{-1}$.

Mass (m/z, % ): 444 (M$^+$, 15), 427 (19 ), 426 (60 ), 409 (29 ), 408 (100), 319 (50), 311 (73), 295 (95).

EXAMPLE 47

Sodium (E)-7-[ 4'-fluoro-6-methoxy-5-methyl-3-(propan-2-yl) biphenyl-2-yl ] -3,5-dihydroxy-6-heptenoate:

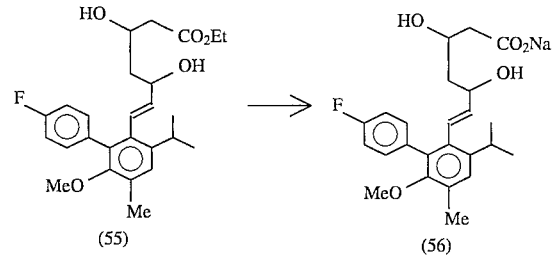

503 mg (1.13 mmol) of Compound 55 synthesized in Example 46 was dissolved in 8 ml of ethanol. To this solution, 1.13 ml (1.13 mmol) of a 1N aqueous solution of sodium hydroxide was added, and the mixture was stirred in an atmosphere of argon at 0° C. for 50 minutes.

The reaction mixture was then concentrated, dissolved in water and subjected to freeze-drying, whereby sodium (E)-7-[4'-fluoro-6-methoxy-5-methyl-3 -(propan-2-yl)biphenyl-2-yl]-3,5-dihydroxy-6-heptenoate (Compound 56) was obtained in the form of a colorless, amorphous solid in a quantitative yield.

$^1$HNMR (300 MHz, CD$_3$OD)

δ1.24 (d, J=6.8Hz, 6H), 1.20–1.38 (m, 1H), 1.57 (ddd, J=13.8, 8.8 and 7.4Hz, 1H), 2.21 (dd, J=15.3 and 7.8Hz, 1H), 2.32 (dd, J=15.3 and 4.5Hz, 1H), 2.33 (s, 3H), 3.30 (s, 3H), 3.25–3.40 (m, 1H), 3.75–3.88 (m, 1H), 4.16–4.28 (m, 1H), 5.27 (dd, J=16.2 and 6.5Hz, 1H), 6.37 (d, J=16.2Hz, 1H), 7.08–7.30 (m, 4H), 7.18 (s, 1H)ppm.

IR (KBr): 3448, 2964, 1574 cm$^{-1}$ .

Mass (FAB-neg, m/z, %): 437 ([M-H]$^-$, 16), 415 (100).

EXAMPLE 48

(E)-3-[ 5-chloro-4'-fluoro-6-methoxy-3-(propan-2-yl) biphenyl-2-yl ] -2-propenenitrile:

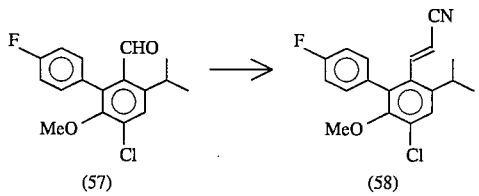

80 mg (2.04 mmol) of a 60% sodium hydride was suspended in 5 ml of anhydrous THF in an atmosphere of argon at 0° C. To this suspension, 0.33 ml (2.04 mmol) of diethyl cyanomethylphosphonate was added, and this mixture was stirred for 20 minutes.

To this reaction mixture, a solution of 519 mg (1.69 mmol) of 5-chloro-4'-fluoro-6-methoxy-3-(propan-2 -yl)biphenyl-2-carbaldehyde (Compound 57) in 5 ml of THF, was added dropwise over a period of 5 minutes, and the mixture was stirred for 20 minutes.

The reaction mixture was then added to a 1N solution of hydrogen chloride. This mixture was extracted with ethyl acetate. The extract layer was successively washed with water, a saturated aqueous solution of sodium chloride, dried over magnesium sulfate, and then concentrated.

The residue was chromatographed on silica gel and eluted with a mixed solvent of hexane and ethyl acetate (8:1), whereby (E)-3-[5-chloro-4'-fluoro-6-methoxy-3 -(propan-2-yl)biphenyl-2-yl]-2-propenenitrile (Compound 58) was obtained in a yield of 511 mg (91.8%).

Melting point: 178.5°–179.0° C. (colorless needles, recrystallized from hexane)

$^1$HNMR (300 MHz, CDCl$_3$)

δ1.25 (d, J=6.8Hz, 6H), 3.09 (hept, J=6.8Hz, 1H), 3.42 (s, 3H), 5.02 (d, J=16.9Hz, 1H), 7.10–7.20 (m, 4H), 7.27 (d, J=16.9Hz, 1H), 7.37 (s, 1H)ppm.

IR (KBr): 2972, 2220, 1624, 1604 cm$^{-1}$.

Mass (m/z, %): 331 (M$^+$, 34), 329 (M$^+$, 100), 316 (24), 314 (70), 301 (6), 299 (19).

EXAMPLE 49

(E)-3-[ 5-chloro-4'-fluoro-6-methoxy-3-(propan-2-yl) biphenyl-2-yl ]-2-propenal:

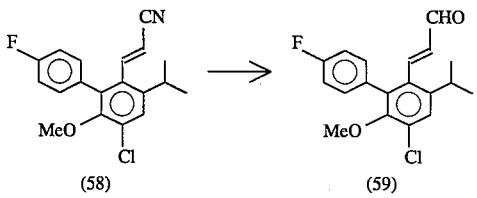

493 mg (1.5 mmol) of Compound 58 synthesized in Example 48 was dissolved in 8 ml of anhydrous toluene. To this solution, 0.94 ml (1.65 mmol) of a 25% hexane solution of diisobutylaluminum hydride was added in an atmosphere of argon at −78° C., and the mixture was then stirred for 60 minutes.

This reaction mixture was then added to a 1N solution of hydrochloric acid. The mixture was then extracted with ethyl acetate.

The extract layer was successively washed with water, and a saturated aqueous solution of sodium chloride, dried over magnesium sulfate, and concentrated.

The residue was crystallized from hexane, whereby (E)-3-[5-chloro-4'-fluoro-6-methoxy-3-(propan-2 -yl)biphenyl-2-yl]-2-propenal (Compound 59) was obtained in a yield of 491 mg (68.9%).

The filtrate obtained in the crystallization was concentrated, chromatographed on silica gel and eluted with a mixed solvent of hexane and ethyl acetate (6:1), whereby Compound 59 was also obtained in a yield of 127 mg (25.5%).

Melting point: 130.0°–131.0° C. (colorless columns, recrystallized from hexane)

$^1$HNMR (300 MHz, CDCl$_3$)

δ1.25 (d, J=6.8 Hz, 6H), 3.18 (hept, J=6.8Hz, 1H), 3.44 (s, 3H), 5.95 (dd, J=16.3 and 7.7Hz, 1H), 7.02–7.15 (m, 2H), 7.16–7.24 (m, 2H), 7.27 (d, J=16.3Hz, 1H), 7.41 (s, 1H), 9.42 (d, J=7.7Hz, 1H)ppm.

IR (KBr): 2972, 2944, 1686, 1628 cm$^{-1}$.

Mass (m/z, %): 334 (M$^+$, 11), 332 (M$^+$, 32), 291 (34), 289 (100), 263 (6), 261 (16).

EXAMPLE 50

Ethyl (E)-7-[ 5.-chloro-4'-fluoro-6-methoxy-3-(propan-2-yl) biphenyl -2-yl ] -5-hydroxy-3-oxo -6-heptenoate:

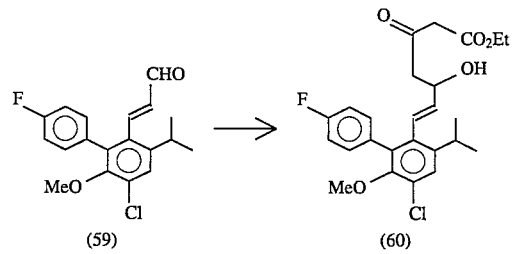

75 mg (1.88 mmol) of a 60% sodium hydride was suspended in 5 ml of anhydrous THF in an atmosphere of argon at 0° C. To this suspension, 0.24 ml (1.88 mmol) of ethyl acetoacetate was added, and this mixture was stirred for 15 minutes. With the addition of 1.17 ml (1.88 mmol) of a 15% hexane solution of butyllithium thereto, the reaction mixture was further stirred for 15 minutes.

To this reaction mixture, 414 mg (1.25 mmol) of Compound 59 synthesized in Example 49 was added.

This mixture was then stirred at 0° C. for 30 minutes and added to a 1N solution of hydrochloric acid.

This mixture was then extracted with ethyl acetate. The extract layer was successively washed with water, and then with a saturated aqueous solution of sodium chloride, dried over magnesium sulfate, and concentrated.

The residue was chromatographed on silica gel and eluted with a mixed solvent of hexane and ethyl acetate (6:1 to 4:1), whereby ethyl (E)-7-[5-chloro-4'-fluoro-6-methoxy-3-(propan-2-yl)biphenyl-2-yl]-5-hydroxy -3-oxo-6-heptenoate (Compound 60) was obtained in a yield of 437 mg (75.9%).

Melting point: 94.0°–94.5° C. (colorless particle-shaped crystals, recrystallized from hexane)

¹HNMR (300 MHz, CDCl₃)

δ1.20 (d, J=6.8Hz, 3H), 1.21 (d, J=6.8Hz, 3H), 1.29 (t, J=7.1Hz, 3H), 2.38–2.56 (m, 2H), 3.14 (hept, J=6.8Hz, 1H), 3.40 (s, 2H), 3.42 (s, 3H), 4.21 (q, J=7.1Hz, 2H), 4.45–4.53 (m, 1H), 5.19 (dd, J=16.1 and 6.0Hz, 1H), 6.38 (d witch fine coupling, J=16.1Hz, 1H), 7.04–7.20 (m, 4H), 7.30 (s, 1H)ppm.

IR (KBr): 3492, 2968, 2940, 1726, 1708, 1604 cm⁻¹.

Mass (m/z, %): 464 (M⁺, 0.1), 462 (M⁺, 0.3), 334 (11), 332 (32), 291 (34), 289 (100).

EXAMPLE 51

Ethyl (E)-7-[5-chloro-4'-fluoro-6-methoxy-3-(propan-2-yl)biphenyl-2-yl]-3,5-dihydroxy-6-heptenoate:

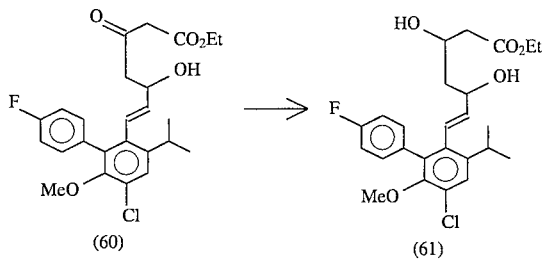

407 mg (0.88 mmol) of Compound 60 synthesized in Example 50 was dissolved, with stirring, in a mixed solvent of 3 ml of anhydrous THF and 1 ml of methanol in an atmosphere of argon at −78° C. by using a cooling bath.

To this solution, 1.0 ml (1.0 mmol) of a 1.0 M THF solution of diethylmethoxyborane was added, and the mixture was stirred at room temperature for 30 minutes, with the removal of the cooling bath at −78° C.

This reaction mixture was again cooled to −78° C., and 38 mg (1.0 mmol) of sodium borohydride was added thereto. The reaction mixture was stirred for 45 minutes.

The reaction mixture was then gradually added, with stirring, to 10 g of a 30% hydrogen peroxide solution at 0° C., and the mixture was stirred at room temperature overnight.

This reaction mixture was then added to a saturated aqueous solution of sodium chloride. This mixture was extracted with ethyl acetate. The extract layer was successively washed with a saturated aqueous solution of sodium chloride, an aqueous solution of sodium thiosulfate, and a saturated aqueous solution of sodium chloride, dried over magnesium sulfate, and concentrated.

The residue was chromatographed on silica gel and eluted with a mixed solvent of hexane and ethyl acetate (3:1), whereby ethyl (E)-7-[5-chloro-4'-fluoro-6-methoxy-3-(propan-2-yl)biphenyl-2-yl]-3,5-dihydroxy-6-heptenoate (Compound 61) was obtained in a yield of 399 mg (97.6%).

Melting point: 87.5°–88.0° C. (colorless, particle-shaped crystals, recrystallized from a mixed solvent of hexane and dichloromethane)

¹HNMR (300 MHz, CDCl₃)

δ1.16–1.30 (m, 1H), 1.20 (d, J=6.8Hz, 3H), 1.21 (d, J=6.8Hz, 3H), 1.29 (t, J=7.1Hz, 3H), 1.31–1.45 (m, 1H), 2.39–2.42 (m, 2H), 3.00 (broad s, 1H), 3.17 (hept, J=6.8Hz, 1H), 3.42 (s, 3H), 3.60 (s with fine coupling, 1H), 4.02–4.13 (m, 1H), 4.19 (q, J=7.1Hz, 2H), 4.25–4.34(m, 1H), 5.20 (dd, J=16.1 and 6.1Hz, 1H ), 6.35 (dd, J=16.1 and 1.1Hz, 1H), 7.01–7.10 (m, 2H), 7.12–7.20 (m, 2H), 7.29 (s, 1H)ppm.

IR (KBr): 3428, 2968, 2930, 1732, 1602 cm⁻¹.

Mass (m/z, % ): 466 (M⁺, 5), 464 (M⁺, 12), 448 (12), 446 (26), 430 (13 ), 428 (28), 420 (20), 418 (53), 317 (43), 315 (85), 291 (52), 289 (100).

EXAMPLE 52

Sodium (E)-7-[5-chloro-4'-fluoro-6-methoxy-3-(propan-2-yl)biphenyl-2-yl]-3,5-dihydroxy-6-heptenoate:

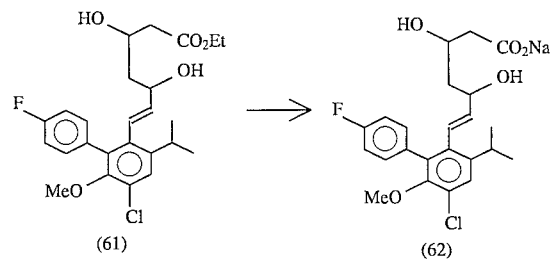

317 mg (0.68 mmol) of Compound 61 synthesized in Example 51 was dissolved in 5 ml of ethanol. To this solution, 0.68 ml (0.68 mmol) of a 1N aqueous solution of sodium hydroxide was added, and the mixture was stirred in an atmosphere of argon at 0° C. for 1 hour.

The reaction mixture was then concentrated, dissolved in water and subjected to freeze-drying, whereby sodium (E)-7-[5-chloro-4'-fluoro-6-methoxy-3 -(propan-2-yl)biphenyl-2-yl]-3,5-dihydroxy-6-heptenoate (Compound 62) was obtained in the form of a colorless, amorphous solid in a quantitative yield.

¹HNMR (300 MHz, CD₃OD)

δ1.25 (d, J=6.8Hz, 6H), 1.29–1.34 (m, 1H), 1.50–1.61 (m, 1H), 2.20 (dd, J=15.3 and 7.9Hz, 1H), 2.31 (dd, J=15.3 and 4.4Hz, 1H), 3.32 (hept, J=6.8Hz, 1H), 3.43 (s, 3H), 3.74–3.85 (m, 1H), 4.18–4.28 (m, 1H), 5.33 (dd, J=16.2 and 6.3Hz, 1H), 6.36 (dd, J=16.2 and 1.1Hz, 1H), 7.12–7.20 (m, 4H), 7.37 (s, 1H)ppm.

IR (KBr): 3416, 2968, 2876, 1602, 1572 cm⁻¹.

Mass (FAB-neg, m/z, %): 459 ([M-H]⁻, 11), 457 ([M-H]⁻, 28), 437 (39), 435 (100).

EXAMPLE 53

(E)-3-[4'-fluoro-5,6-dimethoxy-3-(propan-2-yl)biphenyl-2-yl]-2-propenenitrile:

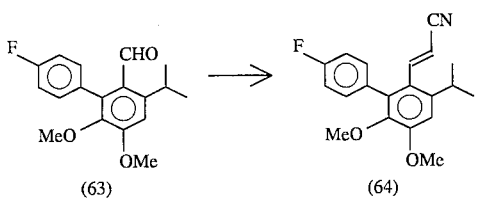

3.12 g (78.1 mmol) of a 60% sodium hydride was suspended in 190 ml of anhydrous THF, and to this suspension, 12.6 ml (78.1 mmol) of diethyl cyanomethylphosphonate was added at 0° C.

To this reaction mixture, a solution of 22.5 g (74.4 mmol) of 4'-fluoro-5,6-dimethoxy-3-(propan-2-yl)biphenyl -2-carbaldehyde (Compound 63) in 110 ml of anhydrous THF, was added dropwise over a period of 10 minutes, and the mixture was stirred in an atmosphere of argon for 30 minutes.

The reaction mixture was then added to a 1N solution of hydrogen chloride. This mixture was extracted with ethyl acetate. The extract layer was successively washed with water and with a saturated aqueous solution of sodium chloride, dried over magnesium sulfate, and then concentrated.

The residue was crystallized from ethyl acetate, whereby (E)-3-[4'-fluoro-5,6-dimethoxy-3-(propan-2 -yl)biphenyl-2-yl]-2-propenenitrile (Compound 64) was obtained in a yield of 19.8 g (81.9%).

The filtrate obtained in the crystallization was concentrated, chromatographed on silica gel and eluted with a mixed solvent of ethyl acetate and hexane (1:4), whereby Compound 64 was also obtained in a yield of 0.88 g (3.6%).

Melting point: 167.0°–168.0° C. (colorless needles, recrystallized from ethyl acetate)

$^1$HNMR (300 MHz, CDCl$_3$)

δ1.27 (d, J=6.8Hz, 6H), 3.19 (hept, J=6.8Hz, 1H), 3.47 (s, 3H), 3.94 (s, 3H), 4.89 (d, J=17.0Hz, 1H), 6.90 (s, 1H), 7.07–7.19 (m, 4H), 7.30 (d, J=17.0Hz, 1H)ppm.

IR (KBr): 2972, 2936, 2212, 1618, 1602, 1582 cm$^{-1}$.

Mass (m/z, %): 325 (M$^+$, 100), 310 (36), 285 (70), 254 (12), 196 (9), 183 (8).

EXAMPLE 54

(E)-3-[4'-fluoro-5,6-dimethoxy-3-(propan-2-yl)biphenyl-2-yl]-2-propenal:

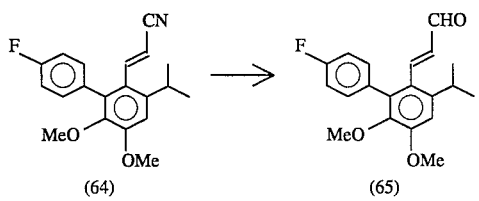

37.7 ml (66.2 mmol) of a 25% hexane solution of diisobutylaluminum hydride was dissolved in 50 ml of anhydrous toluene. This solution was cooled to −78° C.

To this solution was added dropwise a solution of 19.6 g (60.2 mmol) of Compound 64 synthesized in Example 53 in 300 ml of anhydrous THF in an atmosphere of argon over a period of 40 minutes.

This reaction mixture was stirred for 30 minutes, and was further stirred, with the temperature thereof raised to room temperature, overnight. With the addition of a small amount of methanol, this reaction mixture was added to a mixed solvent of a 1N solution of hydrochloric acid and ethyl acetate at 0° C., and the mixture was stirred for 3 hours.

The ethyl acetate layer was successively washed with water and then with a saturated aqueous solution of sodium chloride, dried over magnesium sulfate, and concentrated.

The residue was crystallized from a mixed solvent of ethyl acetate and hexane, whereby (E)-3-[4'-fluoro-5,6-dimethoxy-3-(propan-2-yl)biphenyl-2-yl]-2-propenal (Compound 65) was obtained in a yield of 13.6 g (69.1%).

The filtrate obtained in the crystallization was concentrated, chromatographed on silica gel and eluted with a mixed solvent of dichloromethane and hexane (2:1), and then with dichloromethane, whereby Compound 65 was also obtained in a yield of 3.75 g (19.0%).

Melting point: 138.0°–139.0° C. (yellow, fine particle-shaped crystals, recrystallized from a mixed solvent of ethyl acetate and hexane)

$^1$HNMR (300 MHz, CDCl$_3$)

δ1.28 (d, J=6.8Hz, 6H), 3.29 (hept, J=6.8Hz, 1H), 3.49 (s, 3H), 3.95 (s, 3H), 5.89 (dd, J=16.3 and 7.7Hz, 1H), 6.94 (s, 1H), 7.04–7.13 (m, 2H), 7.13–7.22 (m, 2H), 7.29 (d, J=16.3Hz, 1H), 9.38 (d, J=7.7Hz, 1H)ppm.

IR (KBr): 2968, 2936, 1674, 1622, 1584 cm$^{-1}$.

Mass (m/z, %): 328 (M$^+$, 27), 286 (54), 285 (100), 269 (13), 254 (10).

EXAMPLE 55

Ethyl (E)-7-[4'-fluoro-5,6-dimethoxy-3-(propan-2-yl)biphenyl-2-yl]-5-hydroxy-3-oxo-6-heptenoate:

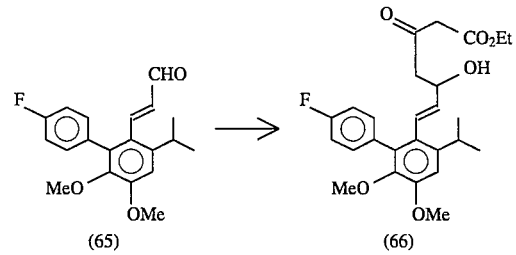

2.70 g (67.6 mmol) of a 60% sodium hydride was suspended in 100 ml of anhydrous THF. To this suspension, 8.62 ml (67.6 mmol) of ethyl acetoacetate was added, and this mixture was stirred in a stream of argon at 0° C. for 30 minutes.

With the addition of 43.3 ml (67.6 mmol) of a 1.66M hexane solution of butyllithium thereto, the reaction mixture was further stirred for 35 minutes, and then cooled to −78° C.

To this reaction mixture, a solution of 17.1 g (52.0 mmol) of Compound 65 synthesized in Example 54 in 120 ml of anhydrous THF was dropwise added over a period of 20 minutes, and the reaction mixture was stirred for 55 minutes.

This reaction mixture was then added to a 1N solution of hydrochloric acid, and the mixture was extracted with ethyl acetate.

The extract layer was successively washed with water, and then with a saturated aqueous solution of sodium chloride, dried over magnesium sulfate, and concentrated.

The residue was chromatographed on silica gel and eluted with a mixed solvent of hexane and ethyl acetate (2:1), whereby ethyl (E)-7-[4'-fluoro-5,6-dimethoxy-3 -(propan-2-yl)biphenyl-2-yl]-5-hydroxy-3-oxo-6-heptenoate (Compound 66) was obtained in a yield of 19.0 g (79.8%).

Melting point: 73.5°–74.0° C. (colorless, fine particle-shaped crystals, recrystallized from a mixed solvent of ethyl acetate and hexane)

¹HNMR (300 MHz, CDCl₃)

δ1.22 (d, J=6.8Hz, 3H), 1.23 (d, J=6.8Hz, 3H), 1.28 (t, J=7.1Hz, 3H), 2.32–2.49 (m, 2H), 3.19 (hept, J=6.8Hz, 1H), 3.40 (s, 2H), 3.48 (s, 3H), 3.91 (s, 3H), 4.20 (q, J=7.1Hz, 2H), 4.42–4.52 (m, 1H), 5.14 (dd, J=16.1 and 6.3Hz, 1H), 6.37 (dd, J=16.1 and 1.2Hz, 1H), 6.86 (s, 1H), 7.01–7.10 (m, 2H), 7.10–7.19 (m, 2H)ppm.

IR (KBr): 3500, 2968, 2940, 1726, 1708 cm⁻¹.

Mass (m/z, %): 458 (M⁺, trace), 440 (8), 328 (11), 285 (100), 1.83 (9), 43 (11).

EXAMPLE 56

Ethyl (E)-7-[4'-fluoro-5,6-dimethoxy-3-(propan-2-yl)biphenyl-2-yl]-3,5-dihydroxy-6-heptenoate:

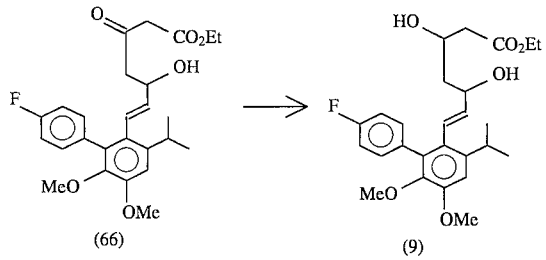

3.37 g (7.36 mmol) of Compound 66 synthesized in Example 55 was dissolved, with stirring, in a mixed solvent of 20 ml of anhydrous THF and 5 ml of methanol in an atmosphere of argon at −78° C. by using a cooling bath.

To this solution, 8.1 ml (8.1 mmol) of a 1.0 M THF solution of diethylmethoxyborane was added, and the mixture was stirred at room temperature for 15 minutes, with the removal of the cooling bath at −78° C.

This reaction mixture was again cooled to −78° C., and 300 mg (7.93 mmol) of sodium borohydride was added thereto. The reaction mixture was stirred for 50 minutes.

The reaction mixture was then gradually added, with stirring, to 25 g of a 30% hydrogen peroxide solution at 0° C., and the mixture was stirred at room temperature for two nights. This reaction mixture was then added to a saturated aqueous solution of sodium chloride. This mixture was extracted with ethyl acetate. The extract layer was successively washed with a saturated aqueous solution of sodium chloride, an aqueous solution of sodium thiosulfate, and a saturated aqueous solution of sodium chloride, dried over magnesium sulfate, and concentrated.

The residue was crystallized from a mixed solvent of ethyl acetate and hexane, whereby ethyl (E)-7-[4'-fluoro-5,6-dimethoxy-3-(propan-2-yl)biphenyl-2-yl]-3,5-dihydroxy-6-heptenoate (Compound 9) was obtained in a yield of 2.73 g (80.3%).

The filtrate obtained in the crystallization was concentrated, chromatographed on silica gel and eluted with a mixed solvent of hexane and ethyl acetate (1:1), whereby Compound 9 was also obtained in a yield of 529 mg (15.6%).

Test 1 Determination of Inhibitory Activity on HMG-CoA Reductase

The inhibitory effect on HMG-CoA Reductase of each of representative examples of the 4-fluorobiphenyl derivatives prepared in the above-discussed examples was determined in accordance with the method described in Journal of Biological Chemistry (J. Biol. Chem.) Vol. 234, page 2835 (1959), and $IC_{50}$ values were obtained. The results are shown in the following Table 1 in comparison with simvastatin.

Test 2 Determination of Inhibition of Sterol Synthesis

Representative compounds (0.3 mg/5ml/kg) suspended in a 5% arabic gum solution were orally given to SD rats weighing 150 to 200 g. One hour later, ¹⁴C-acetic acid (100 μCi/kg) was intraperitoneally injected, and furthermore one hour later, liver was removed to determine the inhibitory activity of each of the compounds on the biosynthesis of sterol in accordance with the method described in European Journal of Biochemistry (Eur. J. Biochem.) Vol.77, page 31 (1977). The results are shown in Table i in comparison with simvastatin.

TABLE 1

| Example | Compound No. | Compound | HMG-CoA Reductase Inhibitory Activity $IC_{50}$ ($10^{-8}$M) | Inhibition of Sterol Synthesis (%) |
|---|---|---|---|---|
| 9 | 11 | Sodium (E)-7-[4'-fluoro-5,6-dimethoxy-3-(propan-2-yl)biphenyl-2-yl]-3,5-dihydroxy-6-heptenoate | 0.543 | 71 |
| 13 | 16 | Sodium (E)-7-[4'-fluoro-5-methoxy-6-(2-methoxyethoxy)-3-(propan-2-yl)biphenyl-2-yl]-3,5-dihydroxy-6-heptenoate | 2.56 | 60 |
| 15 | 19 | Sodium (E)-7-[4'-fluoro-5-methoxy-6-[2-(2-methoxyethoxy)ethoxy]-3-(propan-2-yl)biphenyl-2-yl]-3,5-dihydroxy-6-heptenoate | 0.943 | 69 |
| 32 | 38 | Sodium (E)-7-[4'-fluoro-6-methoxy-5-(2-methoxyethoxy)-3-(propan-2-yl)biphenyl-2-yl]-3,5-dihydroxy-6-heptenoate | 1.61 | 71 |
| 38 | 45 | Sodium (E)-7-[4'-fluoro-5-(2-hydroxyethoxy)-6-methoxy-3-(propan-2-yl)biphenyl-2-yl]-3,5-dihydroxy- | 2.04 | 61 |

TABLE 1-continued

| Example | Compound No. | Compound | HMG-CoA Reductase Inhibitory Activity IC$_{50}$ (10$^{-8}$M) | Inhibition of Sterol Synthesis (%) |
|---|---|---|---|---|
| 42 | 50 | 6-heptenoate Sodium (E)-7-[4'-fluoro-6-methoxy-5-[2-(2-methoxyethoxy)ethoxy]-3-(propan-2-yl)biphenyl-2-yl]-3,5-dihydroxy-6-heptenoate | 2.64 | 62 |
| 47 | 56 | Sodium (E)-7-[4'-fluoro-6-methoxy-5-methyl-3-(propan-2-yl)biphenyl-2-yl]-3,5-dihydroxy-6-heptenoate | 1.66 | 65 |
| 52 | 62 | Sodium (E)-7-[5-chloro-4'-fluoro-6-methoxy-3-(propan-2-yl)biphenyl-2-yl]-3,5-dihydroxy-6-heptenoate | 1.87 | 71 |
| Reference Example | | Simvastatin | 0.695 | 24 |

The 4-fluorobiphenyl derivatives of formula (I), in which A is a ω-oxycarbonyldihydroxybutyl group of formula (II), or a tetrahydropyranyl group of formula (III), have a very strong inhibitory effect on HMG-CoA Reductase, and are useful as a cholesterol lowering agent or a lipid lowering agent.

Furthermore, the 4-fluorobiphenyl derivatives of formula (I), in which A is a ω-oxycarbonyl-3-oxobutyl group of formula (IV), a formyl group, or a cyano group, are useful as intermediates for producing the 4-fluorobiphenyl derivatives of formula (I), in which A is a ω-oxycarbonyldihydroxybutyl group of formula (II), or a tetrahydropyranyl group of formula (III).

Conventionally, compounds with a biphenyl structure are known as compounds having an inhibitory effect on HMG-CoA Reductase. However, 4-fluorobiphenyl derivatives of formula (I), having a substituted represented by R$^1$ at 5-position and an alkoxyl group represented by R$^2$O at 6-position, which have never been produced so far exhibit an inhibitory activity on HMG-CoA Reductase as well as a strong inhibition of cholesterol synthesis in the animals as shown in the results in the above tests.

Therefore, such 4-fluorobiphenyl derivatives are capable of highly lowering the concentration of cholesterol in the blood, and therefore can be employed as a cholesterol lowering agent or a lipid lowering agent, and as an effective drug for curing arteriosclerosis.

Drugs comprising a 4-fluorobiphenyl derivative of formula (I), which can be used as a cholesterol lowering agent or a lipid lowering agent, can be administered not only orally, but also through vena, by hypodermic injection, and by intramuscular injection. Therefore, these drugs can be used in the forms of a tablet, a capsule, a liquid, and a suppository.

What is claimed is:

1. A 4-fluorobiphenyl derivative of the formula (I):

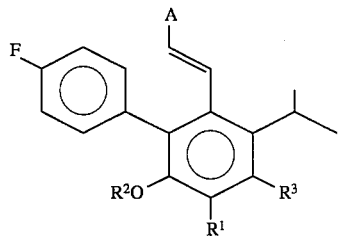

wherein A is a ω-oxycarbonyldihydroxybutyl group of the formula (II):

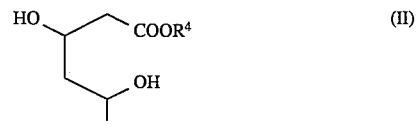

wherein R$^4$ is a hydrogen atom, an alkyl group having 1 to 6 carbon atoms, which is unsubstituted or substituted, an alkaline metal or an alkaline earth metal; a tetrahydropyranyl group of the formula (III):

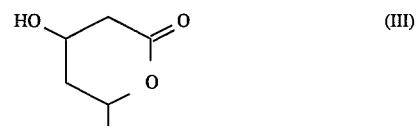

a ω-oxycarbonyl-3-oxybutyl group of the formula (IV):

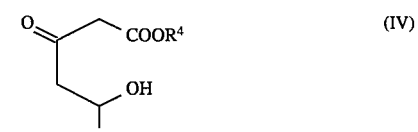

wherein R$^6$ is an alkyl group having 1 to 6 carbon atoms, which is unsubstituted or substituted; a formyl group; or cyano group;

R$^1$ is a halogen atom, methyl group or a group represented by R$^5$O—, wherein R$^5$ is a hydrogen atom, or an alkyl group having 1 to 6 carbon atoms, which is unsubstituted or substituted;

R$^2$ is a hydrogen atom, an alkyl group having 1 to 6 carbon atoms, which is unsubstituted or substituted;

R$^3$ is a hydrogen atom or an alkyl group having 1 to 6 carbon atoms, which is unsubstituted or substituted;

or R$^5$ and R$^2$ together form a 5-membered ring or a 6-membered ring in combination with the oxygen atoms to which R$^5$ and R$^2$ are, respectively bonded;

or R$^5$ and R$^3$ together form a 5-membered ring or a 6-membered ring in combination with the oxygen atom to which R$^5$ is bonded.

2. The 4-fluorobiphenyl derivative as claimed in claim 1, wherein A is a ω-oxycarbonyldihydroxybutyl group of formula (II):

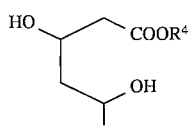

(II)

wherein $R^4$ is a hydrogen atom, an alkyl group having 1 to 6 carbon atoms, which may have a substituted, an alkaline metal or an alkaline earth metal.

3. The 4-fluorobiphenyl derivative as claimed in claim 1, wherein $R^1$ is a group represented by $R^5O$—, wherein $R^5$ is a hydrogen atom, or an alkyl group having 1 to 6 carbon atoms, which is unsubstituted or substituted.

4. The 4-fluorobiphenyl derivative as claimed in claim 1, wherein $R^1$ is a halogen atom.

5. The 4-fluorobiphenyl derivative as claimed in claim 1, wherein $R^1$ is a methyl group.

6. The 4-fluorobiphenyl derivative as claimed in claim 1, wherein $R^2$ is a hydrogen atom.

7. The 4-fluorobiphenyl derivative as claimed in claim 1, wherein $R^2$ is an alkyl group having 1 to 6 carbon atoms, which may have a substituted.

8. The 4-fluorobiphenyl derivative as claimed in claim 1, wherein $R^1$ is a group represented by $R^5O$—, in which $R^5$ is an alkyl group having 1 to 6 carbon atoms, which may have a substituted, and $R^5$ and $R^2$ form a five-membered ring or a six-membered ring in combination with the oxygen atoms to which $R^5$ and $R^2$ are respectively bonded.

9. The 4-fluorobiphenyl derivative as claimed in claim 1, wherein $R^1$ is a group represented by $R^5O$—, wherein $R^5$ is an alkyl group having 1 to 6 carbon atoms, which is unsubstituted or substituted, or $R^5$ and $R^3$ together form a 5-membered ring or a 6-membered ring in combination with the oxygen atom to which $R^5$ is bonded.

10. The 4-fluorobiphenyl derivative as claimed in claim 1, wherein $R^3$ is a hydrogen atom.

11. The 4-fluorobiphenyl derivative as claimed in claim 2, wherein $R^4$ is an alkaline metal.

12. The 4-fluorobiphenyl derivative as claimed in claim 3, wherein $R^5$ is an alkyl group having 1 to 6 carbon atoms, which is unsubstituted or substituted.

13. The 4-fluorobiphenyl derivative as claimed in claim 2, wherein $R^1$ is a group represented by $R^5O$—, wherein $R^5$ is a hydrogen atom, or an alkyl group having 1 to 6 carbon atoms, which is unsubstituted or substituted; $R^2$ is alkyl group having 1 to 6 carbon atoms, which is unsubstituted or substituted, and $R^4$ is an alkaline metal.

14. The 4-fluorobiphenyl derivative as claimed in claim 13, wherein $R^5$ is an alkyl group having 1 to 6 carbon atoms, which is unsubstituted or substituted.

15. The 4-fluorobiphenyl derivative as claimed in claim 13, wherein $R^3$ is a hydrogen atom.

16. A 4-fluorobiphenyl derivative of the formula (Ia):

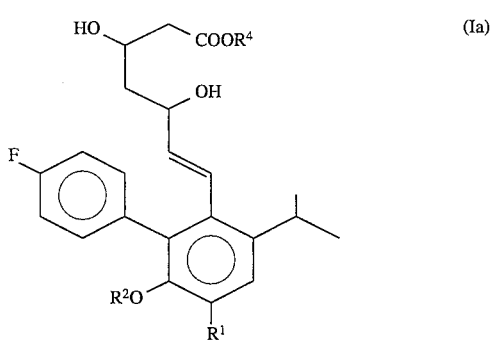

(Ia)

in which $R^1$ is a halogen atom, or a methyl group or a group represented by $R^5O$—, wherein $R^5$ is an alkyl group having 1 to 6 carbon atoms, which is unsubstituted or substituted; $R^2$ is an alkyl group having 1 to 6 carbon atoms, which is unsubstituted or substituted;

or $R^5$ and $R^2$ form a 5-membered ring or a 6-membered ring in combination with the oxygen atoms to which $R^5$ and $R^2$ are, respectively, bonded; and $R^4$ is an alkyl group having 1 to 4 carbon atoms, which is unsubstituted or substituted, or an alkaline metal.

17. The 4-fluorobiphenyl derivative as claimed in claim 16, wherein $R^1$ is a group represented by $R^5O$—, wherein $R^5$ is an alkyl group having 1 to 6 carbon atoms, which is unsubstituted or substituted; and $R^4$ is an alkaline metal.

18. A cholesterol or lipid lowering agent comprising a 4-fluorobiphenyl derivative of the formula (Id) as an effective component:

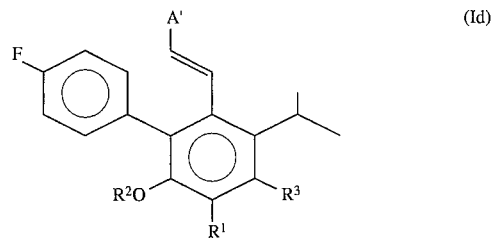

(Id)

wherein A' is a ω-oxycarbonyl dihydroxybutyl group of the formula (II):

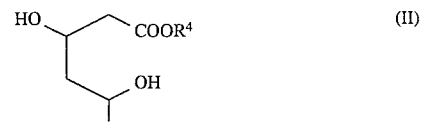

(II)

wherein $R^4$ is a hydrogen atom, an alkyl group having 1 to 6 carbon atoms, which is unsubstituted or substituted, an alkaline metal or an alkaline earth metal; or a tetrahydropyranyl group of the formula (III):

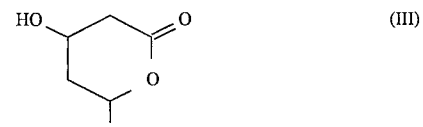

(III)

wherein $R^1$ is a halogen atom, or a methyl group, or a group represented by $R^5O$—, wherein $R^5$ is a hydrogen atom, or an alkyl group having 1 to 6 carbon atoms, which is unsubstituted or substituted; $R^2$ is a hydrogen atom, an alkyl group having 1 to 6 carbon atoms, which is unsubstituted or substituted;

$R^3$ is a hydrogen atom, or an alkyl group having 1 to 6 carbon atoms, which is unsubstituted or substituted;

or $R^5$ and $R^2$ form a 5-membered ring or a 6-membered ring in combination with the oxygen atoms to which $R^5$ and $R^6$ are, respectively, bonded, or $R^5$ and $R^3$ form a 5-membered ring or a 6-membered ring in combination with the oxygen atom to which $R^5$ is bonded.

19. The cholesterol or lipid lowering agent as claimed in claim 18, wherein A' is a ω-oxycarbonyldihydroxybutyl group of formula (II).

20. The cholesterol or lipid lowering agent as claimed in claim 18, wherein $R^1$ is a group represented by $R^5O$—, wherein $R^5$ is a hydrogen atom, or an alkyl group having 1 to 6 carbon atoms, which is unsubstituted or substituted.

21. The cholesterol or lipid lowering agent as claimed in claim 18, wherein $R^1$ is a halogen atom.

22. The cholesterol or lipid lowering agent as claimed in claim 18, wherein $R^1$ is a methyl group.

23. The cholesterol or lipid lowering agent as claimed in claim 18, wherein $R^2$ is a hydrogen atom.

24. The cholesterol or lipid lowering agent as claimed in claim 18, wherein $R^2$ is an alkyl group having 1 to 6 carbon atoms, which is unsubstituted or substituted.

25. The cholesterol or lipid lowering agent as claimed in claim 18, wherein $R^1$ is a group represented by $R^5O$—, in which $R^5$ is an alkyl group having 1 to 6 carbon atoms, which is unsubstituted or substituted, and $R^5$ and $R^2$ form a five-membered ring or a six-membered ring in combination with the oxygen atoms to which $R^5$ and $R^2$ are respectively bonded.

26. The cholesterol or lipid lowering agent as claimed in claim 18, wherein $R^1$ is a group represented by $R^5O$—, wherein $R^5$ is an alkyl group having 1 to 6 carbon atoms, which is unsubstituted or substituted, and $R^5$ and $R^3$ may form a five-membered ring or a six-membered ring in combination with the oxygen atom to which $R^5$ is bonded.

27. The cholesterol or lipid lowering agent as claimed in claim 18, wherein $R^3$ is a hydrogen atom.

28. The cholesterol or lipid lowering agent as claimed in claim 18, wherein $R^4$ is an alkaline metal.

29. The cholesterol or lipid lowering agent as claimed in claim 18, wherein $R^5$ is an alkyl group having 1 to 6 carbon atoms, which is unsubstituted or substituted.

30. The cholesterol or lipid lowering agent as claimed in claim 18, wherein $R^1$ is a group represented by $R^5O$—, wherein $R^5$ is a hydrogen atom, or an alkyl group having 1 to 6 carbon atoms, which is unsubstituted or substituted; $R^2$ is an alkyl group having 1 to 6 carbon atoms, which is unsubstituted or substituted, and $R^4$ is an alkaline metal.

31. The cholesterol or lipid lowering agent as claimed in claim 18, wherein $R^5$ is an alkyl group having 1 to 6 carbon atoms, which is unsubstituted or substituted.

32. The cholesterol or lipid lowering agent as claimed in claim 18, wherein $R^3$ is a hydrogen atom.

33. A cholesterol or lipid lowering agent comprising a 4-fluorobiphenyl derivative of the formula (Ia) as an effective component:

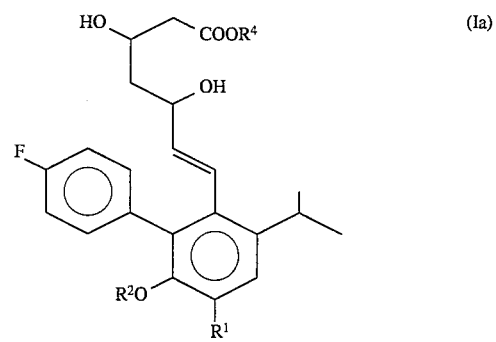

in which $R^1$ is a halogen atom, or a methyl group, or a group represented by $R^5O$—, wherein $R^5$ is an alkyl group having 1–6 carbon atoms, which is unsubstituted or substituted; $R^2$ is an alkyl group having 1 to 6 carbon atoms, which is unsubstituted or substituted; or $R^5$ and $R^2$ form a 5-membered ring or a 6-membered ring in combination with the oxygen atoms to which $R^5$ and $R^2$ are respectively bonded; and $R^4$ is an alkyl group having 1 to 6 carbon atoms, which is unsubstituted or substituted, or an alkaline metal.

34. The cholesterol or lipid lowering agent as claimed in claim 33, wherein $R^1$ is a group represented by $R^5O$—, wherein $R^5$ is an alkyl group having 1 to 6 carbon atoms, which is unsubstituted or substituted; and $R^4$ is an alkaline metal.

35. The 4-fluorobiphenyl derivative as claimed in claim 1, wherein $R^1$ is halogen atom or a group of the formula $R^5O$—, wherein $R^5$ is hydrogen atom or an alkyl group of 1 to 6 carbon atoms, which is unsubstituted or substituted.

36. The cholesterol or lipid lowering agent as claimed in claim 18, wherein $R^1$ is halogen atom or a group of the formula $R^5O$—, wherein $R^5$ is hydrogen atom or an alkyl group of 1–6 carbon atoms, which is unsubstituted or substituted.

* * * * *